US007667094B2

(12) United States Patent
Yoshioka

(10) Patent No.: US 7,667,094 B2
(45) Date of Patent: Feb. 23, 2010

(54) GERM-RESPONSIVE PROMOTER

(75) Inventor: Hirofumi Yoshioka, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 947 days.

(21) Appl. No.: 10/537,094

(22) PCT Filed: Dec. 1, 2003

(86) PCT No.: PCT/JP03/15310

§ 371 (c)(1),
(2), (4) Date: Jun. 2, 2005

(87) PCT Pub. No.: WO2004/050874

PCT Pub. Date: Jun. 17, 2004

(65) Prior Publication Data

US 2006/0053509 A1 Mar. 9, 2006

(30) Foreign Application Priority Data

Dec. 3, 2002 (JP) ............................. 2002-351701
Aug. 18, 2003 (JP) ............................. 2003-294409

(51) Int. Cl.
*C12N 15/09* (2006.01)
*C12N 15/82* (2006.01)
*A01H 5/00* (2006.01)
(52) U.S. Cl. ..................... 800/279; 800/278; 800/298; 800/317; 536/24.1; 435/320.1; 435/468; 435/419
(58) Field of Classification Search ....................... None
See application file for complete search history.

(56) References Cited

U.S. PATENT DOCUMENTS 5,723,760 A * 3/1998 Strittmatter et al. ......... 800/301

FOREIGN PATENT DOCUMENTS

| EP | 1078985 | 2/2001 |
| WO | WO-91/15585 | 10/1991 |

OTHER PUBLICATIONS

F. Xiao, et al.; "Expression of 35S::Pto Globally Activates Defense-Related Genes in Tomato Plants;" *Plant Physiol.*; vol. 126; No. 4; pp. 1637-1645; 2001.

T. Nishiuchi, et al.; "Roles of Plastid ω-3 Fatty Acid Desaturases in Defense Response of Higher Plants;" *J. Plant Res.*; vol. 111; No. 1104; pp. 481-486; 1998.
L. Jorda, et al.; "Local and Syntemic Induction of Two Defense-Related Subtilisin-Like Protease Promoters in Transgenic Arabidopssis Plants;" *Plant Physiol.*; vol. 124; No. 3; pp. 1049-1057; 2000.
Back et al; "Identifying functional domains within terpene cyclases using a domain-swapping strategy." Proc. Natl. Acad. Sci. vol. 93 (Jun. 1996) 6841-6845.
Yoshioka et al; "Expression of Genes for Phenylalanine Ammonia-Lyase and 3-Hydroxy-3-Methylglutaryl CoA Reductase in Aged Potato Tubers Infected with Phytophthora infestans;" Plant Cell physiol. 37(1) (1996) 81-90.
Yoshioka et al; "CDNA Cloning of Sesquiterpene Cyclase and Squalene Synthase, and Expression of the Genes in Potato Tuber Infected with Phytophthora infestans;" Plant Cell Physiol. 40(9) (1999) 993-998.
Zook et al; "Induction of sesquiterpene cyclase and suppression of squalene synthetase activity in elicitor-treated or fungal-infected potato tuber tissue;" Physiological and Molecular Plant Pathology 38 (1991) 377-390.
Hirofumi Yoshioka et al., "cDNA Cloning of Sesquiterpene Cyclase and Squalene Synthase, and Expression of the Genes in Potato Tuber Infected with *Phytophthora infestans*," Plant Cell Physiology, vol. 40, No. 9, Sep. 1999, p. 993-998.
Yoshioka H. et al., "Solanum tuberosum PVS3 mRNA for vetispiradiene synthase, complete cds," Database EMBL [Online], XP-002444030 retrived from EBI accession No. Embl: AB022720, 2 pages.
MHAI Joosten et al., "The Tomato—*Cladosporium fulvum* Interaction: A Versatile Experimental System to Study Plant-Pathogen Interactions," Annual Review of Phytopathol, 1999, pp. 335-367.
Japanese Journal of phytopathology, vol. 68 No. 2, 2002, p. 166.
K.-Y. Yang et al., "Activation of a mitogen-activated protein kinase pathway is involved in disease resistance in tabacco," PNAS, vol. 98 No. 2, 2001 pp. 741-746.
Notification of Reasons for Refusal mailed Jul. 21, 2009, issued on the corresponding Japanese application No. 2003-294409 and the English translation thereof.
Japanese Journal of Phytopathology, vol. 68 No. 2, 2002, p. 166 and the partial translation thereof (2 pages).

* cited by examiner

*Primary Examiner*—Medina A Ibrahim
(74) *Attorney, Agent, or Firm*—Edwards Angell Palmer & Dodge LLP

(57) ABSTRACT

The present invention relates to isolated promoter sequences responsive to germ infection and functioning in plants; vectors and DNA comprising the promoter sequences are also disclosed. The invention further relates to methods of transforming plants with a DNA construct comprising a germ responsive promoter operably linked to a pathogen resistant gene.

20 Claims, 32 Drawing Sheets

Fig. 6

```
-2648 ctcttctgttgatgtgctatagtcttttatatagcgctctattcatgttgtaatttggcc -2589
-2588 tctactttaatttttttcaacctaaaccaacgtacaataatgtgtaatgatactaatttg -2529
-2528 actcacataatagcatggtgctagaagagtcacttgaaagagtatactgaagagtattaa -2469
-2468 aaatataattctaaagaatttcgaagattcaattataattgatcaagaaggtgataagag -2409
-2408 ccttcnacaacaacgtaaagtttgggtagcctctatanatgactatgaaaatagccaaaa -2349
-2348 aaaaattcaaattcgaattcttgtaatccttatttaggattattgcgaccatcacttgtg -2289
-2288 ggtgccttacttgactaaatatttgattaaacattaattttttggtcagtggatatacatg -2229
-2228 ccactcaattttaaataaattagtgatcccttacgatcttaaaaaaattgtattttgtg -2169
-2168 tgtaatgtcaactttggttcaaatgtctaatataataagtattaattccaacagtattag -2109
-2108 aattttatttctaagatcactcttacggtcttaccactgaaagattaaaattctaaccaa -2049
-2048 gaatttgaactttaaatagtacttatgaattttacttgccgtttgaattttatgtacatg -1989
-1988 cttagaataattaggtcctcatgtagtcaactttaagaaaattacaatgttacgttctaa -1929
-1928 caagaacaaatttgactctagattttttaatttttttttttaaaaaaaaactaaatactc -1869
-1868 atccgattcaatttgtttgaaactatgttccaattattaatccgtttcaaaaacaatgtt -1809
-1808 acattcagatatttaaaatcaattaacttaaatttctcatcatcagtaagaagttttaat -1749
-1748 aatcacatgaaggaaagcctgtttggagaaagttatgcgtaaaatattgcatatatctct -1689
-1688 tccattgaattagttacatctggatttgcataaaatcaacatttagtaaaatacgatggc -1629
-1628 ttagatgattgaactttgaacaggaaaaataagcgtgcaaataagccatcaatcttgaac -1569
-1568 tttagaaatatatatatataattcaataagttactttattggaatagctatagtgacggc -1509
-1508 ggatttagaattttcattaaagggactctaaaaaaatatagtgcctaagatttgaacttg -1449
-1448 aaactcaagatgccactaaacaacctctaatcttacattcagaaggttcaaaatcaatat -1389
-1388 atatagacataattttttaaattttttttaacctccctcgactacctctaggtccgccct -1329
-1328 tactattcccatccgatctcttgggaagcggggggagaaaatttttataatagtgcactcat -1269
-1268 gctataattacatactaagattttatgtaatgctatatttttttcaagttgaagacggaaa -1209
-1208 caatagcattggatcaagacagacgccattgaaggaagaaaaaacctaaaaaaataaaca -1149
-1148 aaaggagagacactttcttggtccctcgaggccatatatcccattaataataaaaatata -1089
-1088 aaacaaaaaaaaagacagacggtcgcccaaggaaagaaggcggacgtcactaacggctaa -1029
-1028 ccctaactacaaataatgtaattttccaaaaacggaactataaggaataaaaaacatgaa -969
-968 gattattgagtattattaattttaaaagacagacgccactcgaggaaataaggaatcac -909
-908 aaggagtaaagaaagaaattaaaggcacgttacagtatcatataaatataaatttaagttt -849
-848 ggttgcattgaagttatatagttttaaaaaaaaataaaattgtccaacaatacttgtcc -789
-788 aatttagaaaatctaaaagataatttattatttttgtgtttgttttacctcaacatctaat -729
-728 acatttctcaaattattaaatttaatatattcaaaaggtaatatagtaatattactctta -669
-668 ttatttatttattgtttcttaagatttgtgcaggtcaataataataactatcgttgaat -609
-608 taagggagtaccatcaaagaaattgatttataacacgatgcgggtggagggagctagaaa -549
-548 gttagtacaaatttggttgcactaagtacttcatccgtctcaatttatgagattttgttt -489
-488 gattcgagacgaaatttaataaagatgattttttaaagttgtaatctaaaacaagtcat -429
-428 aaatatttgcatcactataataatctcattaaatgtaaatgaatatttttagctaaatta -369
-368 ttactactccctccatgtccatattagttgatcatcttactatatattaactgtccacct -309
-308 tactcaattaataaaatattaattaaagttttttctatactagatataaaaatgttattat -249
-248 tattttttgataaagactagaaagagtatactatttgtatatctaagtgggacgaccagt -189
-188 taagtatattgtagtcaaagtaaggcaaccggatggactgcatgcagcacaaaggctctc -129
-128 accactataaatactcaatattccttctctttcatttccatcaacaccttcaccaactaa -69
-68 caaattaaaagaaagaaaaaaaaatctctcagtttcctcacaagctaattagacccgttt -9
-8 ccgaagaaATGGCCCTAGCTATCCCCTTTAACAATGAAGAGGAGATTGTTCGCCCTGTTG 52
1                M  A  L  A  I  P  F  N  N  E  E  E  I  V  R  P  V          17

53 CCAATTTCTCTCCAAGTCTTTGGGGTGATCGTTTTCCATTCATTCTCTCTCGACAATCAGg 112
18   A  N  F  S  P  S  L  W  G  D  R  F  H  S  F  S  L  D  N  Q       37

113 taattacttaattaattactaattaaatccttctctatcgcttatatttggttaattact 172
173 actaatcccaatcatgaacatttttacagGTTGCTGAAAAGTATGCTCAAGAGATTGAAAC 232
38                                V  A  E  K  Y  A  Q  E  I  E  T       48

233 TTTGAAGGAACAAACAAGGAGTTTGTTGTCTGCTGCTGCTTGTGGAATAACATTGGCTGA 292
49   L  K  E  Q  T  R  S  L  L  S  A  A  A  C  G  I  T  L  A  E       68

293 GAAATTGAATCTGATAGACATTGTTGAGCGCCTTGGCTTAGCTTATCATTTTGAGAAACA 352
69   K  L  N  L  I  D  I  V  E  R  L  G  L  A  Y  H  F  E  K  Q       88

353 AATAGATGATATGTTGGATCAAATTTACAAAGCAGATCCCAACTTTGACGCTCATGATTT 412
89   I  D  D  M  L  D  Q  I  Y  K  A  D  P  N  F  D  A  H  D  L      108

413 AAACACTTTATCCCTTCAATTTCGAATATTAAGACAACATGGTTACAATATCTCCCAAAg 472
109  N  T  L  S  L  Q  F  R  I  L  R  Q  H  G  Y  N  I  S  Q         127

473 taggtccatcatttaaaacaattcaccaaaataatacgttttttctgcatgaaaactaa 532
533 ttatcttttgcttttattcgatcatgatccagAATTTTTCAGCAGATTCCAAGATGCGAA 592
128                                  K  F  F  S  R  F  Q  D  A  N      137

593 TGGCAAGTTCAAGGAATGTCTTAGCAACGACATCAGGGGTCTATTGAACTTATACGAAGC 652
138  G  K  F  K  E  C  L  S  N  D  I  R  G  L  L  N  L  Y  E  A      157

653 TTCACATGTAAGGACTCATGGAGAAGATATTTTAGAAGAGGCACTTGTTTTCTCCACTGC 712
158  S  H  V  R  T  H  G  E  D  I  L  E  E  A  L  V  F  S  T  A      177

713 TCATCTTGAGTCTGCAGCTCCACATTTGGAGTCACCTCTGAGTAAGCAAGTGACTCATGC 772
178  H  L  E  S  A  A  P  H  L  E  S  P  L  S  K  Q  V  T  H  A      197
```

Fig. 7

```
 773 CCTTGAGCAGTCTCTCCATAAGAGCATTCCAAGAGTCGAGACGCGCTACTTCATCTCCAT  832
 198   L  E  Q  S  L  H  K  S  I  P  R  V  E  T  R  Y  F  I  S  I   217

833 CTACGAAGAGGAGGAATTTAAGAATGATGTGTTGCTTCGATTTGCCAAATTGGATTACAA  892
 218   Y  E  E  E  F  K  N  D  V  L  L  R  F  A  K  L  D  Y       237

893 CTTACTCCAGATGTTGCACAAACACGAACTTAGTGAAGTATCAAGgtatacagatgtgtt  952
 238   L  L  Q  M  L  H  K  H  E  L  S  E  V  S  R                252

953 aagttgaattaaaaatactagtataaattatttgttgatagtaatttctaagattggtac 1012
1013 ttattttgtagGTGGTGGAAAGATTTGGATTTTGTGACAACGCTTCCATATGCTAGGGAT 1072
 253             W  W  K  D  L  D  F  V  T  T  L  P  Y  A  R  D   268

1073 AGAGCAGTGGAATGTTACTTTTGGACGATGGAGTGTATGCTGAACCTCAATACTCTCAG  1132
 269   R  A  V  E  C  Y  F  W  T  M  G  V  Y  A  E  P  Q  Y  S  Q  288

1133 GCTCGTGTCATCCTTGCAAAGACTATAGCAATGATTTCGATAGTAGATGACACATTCGAT 1192
 289   A  R  V  I  L  A  K  T  I  A  M  I  S  I  V  D  D  T  F  D  308

1193 GCTTATGGAATAGTAAAAGAACTTGAGGTCTACACCGATGCCATACAAAGgtatggactt 1252
 309   A  Y  G  I  V  K  E  L  E  V  Y  T  D  A  I  Q  R          325

1253 gcctctccaacagttcatggatttattagacgggaaacttactaaatctctttctgtttt 1312
1313 attagGTGGGATATTAGTCAAATTGATCGACTCCCAGAATACATGAAAGTTAGTTTTAAG 1372
 326        W  D  I  S  Q  I  D  R  L  P  E  Y  M  K  V  S  F  K   343

1373 GCTCTTTTGGATCTCTATGAAGATTATGAAAAGGAGTTGTCAAAGGATGGCAGATCCGAT 1432
 344   A  L  L  D  L  Y  E  D  Y  E  K  E  L  S  K  D  G  R  S  D  363

1433 GTTGTCCACTACGCAAAAGAAAGAgtaggactcactgatttctatttaaaaacacttgta 1492
 364   V  V  H  Y  A  K  E  R                                      371

1493 tttaccttatactatttctttattatacaattagatctgttatgggagtattgatggttg 1552
1553 aatgtcttgtggtttctgttaaacagATGAAGGAGATTGTGAGAAACTATTTTGTAGAAG 1612
 372                             M  K  E  I  V  R  N  Y  F  V  E   382

1613 CAAAGTGGTTCATTGAGGGATATATGCCGCCTGTTTCTGAGTATCTTAGCAATGCATTAG 1672
 383   A  K  W  F  I  E  G  Y  M  P  P  V  S  E  Y  L  S  N  A  L  402

1673 CTACCAGCACATATTACTTGCTAACTACAACATCCTATTTGGGAGTGAAGTCAGCAACAA 1732
 403   A  T  S  T  Y  Y  L  L  T  T  T  S  Y  L  G  V  K  S  A  T  422

1733 AGGAAGATTTTGAATGGTTGGCTACGAACCCTAAAATTCTTGAAGCCAATGTGACATTAT 1792
 423   K  E  D  F  E  W  L  A  T  N  P  K  I  L  E  A  N  V  T  L  442

1793 GCCGAGTTGTTGATGACATAGCAACGTATGAGgtaattagcatcgcattacactacataa 1852
 443   C  R  V  V  D  D  I  A  T  Y  E                             453

1853 atcatcttataatttagagttacagtaatttaatacaaattgatttcacatacttataaa 1912
1913 tgaattataattgccattccagGTTGAGAAGGGTAGGGGCCAAATCGCAACAGGAATTGA 1972
 454                         V  E  K  G  R  G  Q  I  A  T  G  I  E 466

1973 GTGTTATATGAGGGATTATGACGTATCAACAGAAGTAGCAATGGAAAAATTCCAAGAGAT 2032
 467   C  Y  M  R  D  Y  D  V  S  T  E  V  A  M  E  K  F  Q  E  M  486

2033 GGCTGAGATAGCATGGAAGGATGTAAATGAAGGAATTCTTCGACCAACACCTGTCTCTAC 2092
 487   A  E  I  A  W  K  D  V  N  E  G  I  L  R  P  T  P  V  S  T  506

2093 AGAAATTCTTACTCGCATTCTCAATCTTGCTCGTATTATAGATGTCACTTACAAGCACAA 2152
 507   E  I  L  T  R  I  L  N  L  A  R  I  I  D  V  T  Y  K  H  N  526

2153 TCAAGATGGATACACTCATCCCGAAAAAGTTCTAAAACCTCACATCATTGCTTTACTGGT 2212
 527   Q  D  G  Y  T  H  P  E  K  V  L  K  P  H  I  I  A  L  L  V  546

2213 GGACTCCATTGAGATCtaaaaatttagtaaattttaattttttaaaatgttacgtaaaaaa 2272
 547   D  S  I  E  I  *                                           551

2273 taataaaccgtaaaaataatgaagattaaggcgaacgaaccacgtgaggcggaaacgttg 2332
2333 agaatggatgatggaaaatagatgaatatattgttatgcatgaagggtgtttcacactct 2392
2393 tttgatttgggaatgcatggacatccgcatgttgtcgactacacctcgaccaatgttgc  2452
2453 gcaagccacggccgatgcgggcaggccacggatgaccgttgtgtgcagtccaagggcgat 2512
2513 gcggccaggccacggccgatgtcgactgaccgttgtgtgcagtccaagggcgatgcgggc 2572
2573 aggccacgtccgacgt                                              2588
```

Fig. 10
(A)
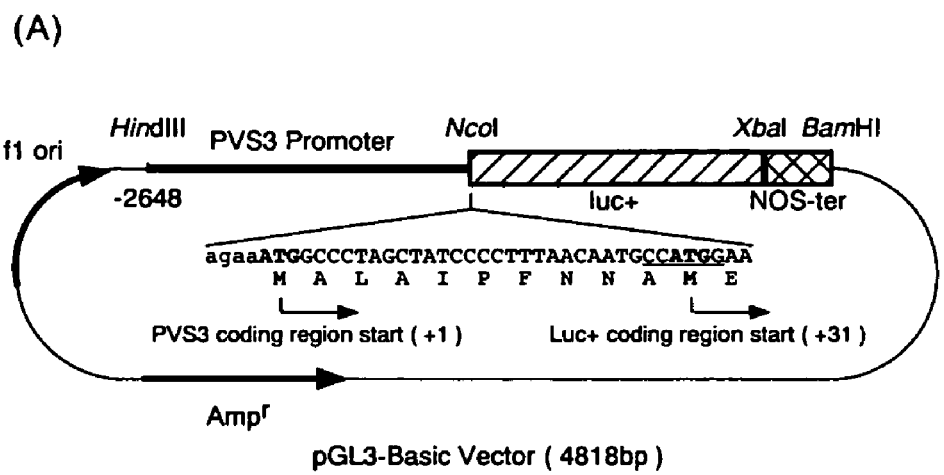
(B)
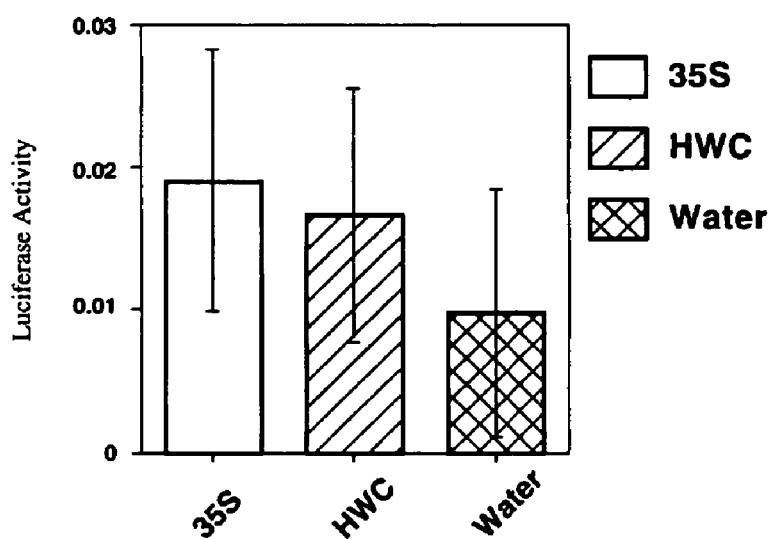

Fig. 16
Hours after treatment with $H_2O_2$
6         12         24         48
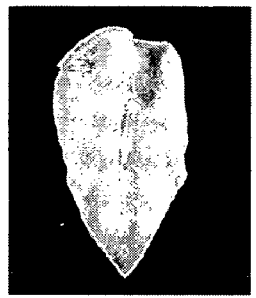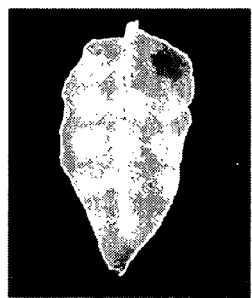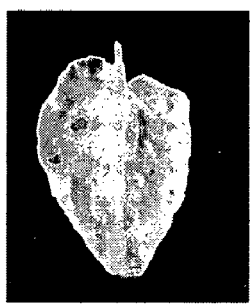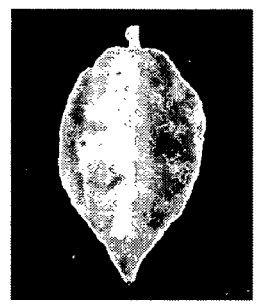

Fig. 17
Hours after treatment with glucose and glucose-oxidase
6          12          24          48
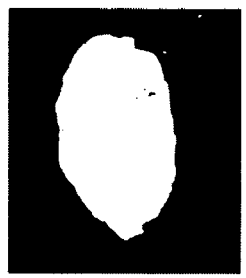  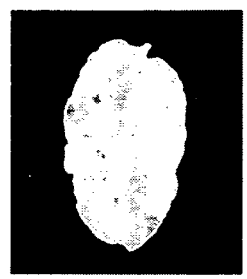 

Fig. 18
Hours after treatment with SA
6        12        24        48
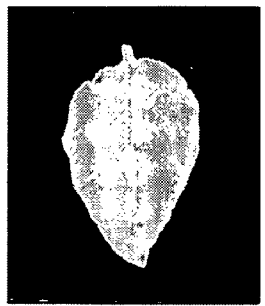 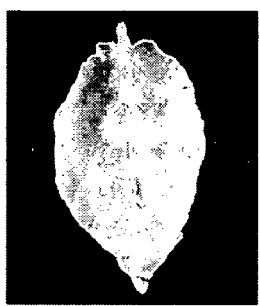 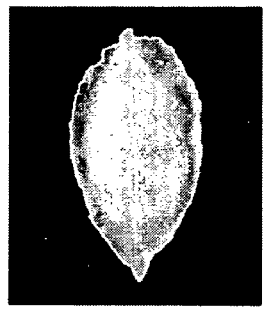 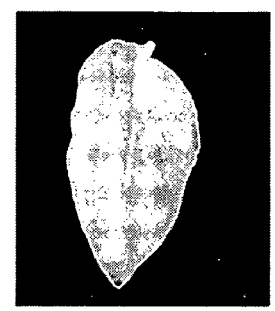

Fig. 21

ATGCGACCTCTTCAACCACCCCCACCAGCTGCCAACTCCACCTCCTCCGCCGCCGCATCATC
CATGCCTCCTCCCTCTTCCGCCGGACAACGCAGTCGTCCCCGGCGTCGTACTGATTTGACCC
TTCCTCTTCCTCAACGTGACGTTGCTCTTGCTGTTCCTCTCCCCCTTCCTCCAACCTCCGCTC
CTTCCTCTTCCTCATCCTCATCTTCCTCCCCGCTTCCTACCCCTTTACATTTCTCTGAGCTCG
AGAGGGTTAATCGCATCGGTAGTGGCACCGGAGGTACTGTTTACAAGGTTCTACATCGTCCC
ACTGGCAGACTCTATGCTTTGAAAGTTATCTATGGTAACCATGAGGATTCTGTCCGTCTCCAG
ATGTGCCGTGAGATCGAGATTCTCCGAGATGTAGACAACCCTAACGTCGTTAGGTGTCACGA
TATGTTCGATCACAACGGCGAAATCCAAGTTCTTCTTGAGTTCATGGATAAAGGCTCTCTCG
AAGGGATCCATATCCCTCTCGAACAACCTCTCTCCGATCTAACTCGACAGGTTCTCTCCGGC
CTCTACTACCTCCACAGGCGTAAGATTGTTCACAGAGATATCAAACCTTCTAACCTCTTAATC
AACTCCAGGCGTGAGGTCAAGATTGCAGATTTTGGGGTCTCCAGAGTTCTCGCACAAACTAT
GGATCCTTGCAATTCCTCCGTGGGTACCATCGCTTACATGAGTCCCGAGAGAATCAACACAG
ATCTGAATCACGGACAGTACGACGGATATGCTGGGGACATATGGAGTCTTGGGGTGAGCATC
TTAGAGTTCTACTTGGGAAGGTTCCCCTTCTCTGTGGGGAGACAAGGAGACTGGGCCAGCC
TTATGTGCGCCATTTGTATGTCGCAGCCTCCTGAGGCACCACCCACTGCTTCCAGGGAGTTT
AGGGAGTTCATTGCCTGCTGTTTGCAGAGGGATCCTGCTAGGCGGTGGACGGCCGCGCAGC
TCTTGCGCCATCCCTTCATCACCCAGAATAGCCCAGGCACCCACACCGGTCCTGCTACTACC
TCATTGAGTAATCAGGCACATCAATTGTTACCTCCACCTCCTCATTTTTCTTCTTCTTCTTCTT
CTTGA

MRPLQPPPPAANSTSSAAASSMPPPSSAGQRSRPRRRTDLTLPLPQRDVALAVPLPLPPTSAPS
SSSSSSSSPLPTPLHFSELERVNRIGSGTGGTVYKVLHRPTGRLYALKVTYGNHEDSVRLQMCR
EIEILRDVDNPNVVRCHDMFDHNGEIQVLLEFMDKGSLEGIHIPLEQPLSDLTRQVLSGLYYL
HRRKIVHRDIKPSNLLINSRREVKIADFGVSRVLAQTMDPCNSSVGTIAYMSPERINTDLNHG
QYDGYAGDIWSLGVSILEFYLGRFPFSVGRQGDWASLMCAICMSQPPEAPPTASREFREFIAC
CLQRDPARRWTAAQLLRHPFITQNSPGTHTGPATTSLSNQAHQLLPPPPHFSSSSSS

Fig. 22

ATGCGACCTCTTCAACCACCCCCACCAGCTGCCAACTCCACCTCCTCCGCCGCCGCATCATC
CATGCCTCCTCCCTCTTCCGCCGGACAACGCAGTCGTCCCCGGCGTCGTACTGATTTGACCC
TTCCTCTTCCTCAACGTGACGTTGCTCTTGCTGTTCCTCTCCCCCTTCCTCCAACCTCCGCTC
CTTCCTCTTCCTCATCCTCATCTTCCTCCCCGCTTCCTACCCCTTTACATTTCTCTGAGCTCG
AGAGGGTTAATCGCATCGGTAGTGGCACCGGAGGTACTGTTTACAAGGTTCTACATCGTCCC
ACTGGCAGACTCTATGCTTTGAAAGTTATCTATGGTAACCATGAGGATTCTGTCCGTCTCCAG
ATGTGCCGTGAGATCGAGATTCTCCGAGATGTAGACAACCCTAACGTCGTTAGGTGTCACGA
TATGTTCGATCACAACGGCGAAATCCAAGTTCTTCTTGAGTTCATGGATAAAGGCTCTCTCG
AAGGGATCCATATCCCTCTCGAACAACCTCTCTCCGATCTAACTCGACAGGTTCTCTCCGGC
CTCTACTACCTCCACAGGCGTAAGATTGTTCACAGAGATATCAAACCTTCTAACCTCTTAATC
AACTCCAGGCGTGAGGTCAAGATTGCAGATTTTGGGGTCTCCAGAGTTCTCGCACAAGATAT
GGATCCTTGCAATGACTCCGTGGGTACCATCGCTTACATGAGTCCCGAGAGAATCAACACAG
ATCTGAATCACGGACAGTACGACGGATATGCTGGGGACATATGGAGTCTTGGGGTGAGCATC
TTAGAGTTCTACTTGGGAAGGTTCCCCTTCTCTGTGGGGAGACAAGGAGACTGGGCCAGCC
TTATGTGCGCCATTTGTATGTCGCAGCCTCCTGAGGCACCACCCACTGCTTCCAGGGAGTTT
AGGGAGTTCATTGCCTGCTGTTTGCAGAGGGATCCTGCTAGGCGGTGGACGGCCGCGCAGC
TCTTGCGCCATCCCTTCATCACCCAGAATAGCCCAGGCACCCACACCGGTCCTGCTACTACC
TCATTGAGTAATCAGGCACATCAATTGTTACCTCCACCTCCTCATTTTTCTTCTTCTTCTTCTT
CTTGA

MRPLQPPPPAANSTSSAAASSMPPPSSAGQRSRPRRRTDLTLPLPQRDVALAVPLPLPPTSAPS
SSSSSSSSPLPTPLHFSELERVNRIGSGTGGTVYKVLHRPTGRLYALKVIYGNHEDSVRLQMCR
EIEILRDVDNPNVVRCHDMFDHNGEIQVLLEFMDKGSLEGIHIPLEQPLSDLTRQVLSGLYYL
HRRKIVHRDIKPSNLLINSRREVKIADFGVSRVLAQDMDPCNDSVGTIAYMSPERINTDLNHG
QYDGYAGDIWSLGVSILEFYLGRFPFSVGRQGDWASLMCAICMSQPPEAPPTASREFREFIAC
CLQRDPARRWTAAQLLRHPFITQNSPGTHTGPATTSLSNQAHQLLPPPPHFSSSSSS

Fig. 24

| Name | Primer sequence | |
|---|---|---|
| PVS3-1 (-2334) : F | 5'-CGGAATTCTTGTAATCCTTATTTAGGATTA-3' | SEQ ID NO:25 |
| PVS3-2 (-1337) : F | 5'-CGGAATTCGTCCGCCCTTACTATTCCCATC-3' | SEQ ID NO:26 |
| PVS3-3 (-1287) : F | 5'-CGGAATTCTTTATAATAGTGCACTCATGCT-3' | SEQ ID NO:27 |
| PVS3-4 (-1237) : F | 5'-CGGAATTCGCTATATTTTTTCAAGTTGAAG-3' | SEQ ID NO:28 |
| PVS3-5 (-1187) : F | 5'-CGGAATTCGACGCCATTGAAGGAAGAAAAA-3' | SEQ ID NO:29 |
| PVS3-6 (-1137) : F | 5'-CGGAATTCACTTTCTTGGTCCCTTCGAGGC-3' | SEQ ID NO:30 |
| PVS3-7 (-1087) : F | 5'-CGGAATTCAACAAAAAAAAAGACAGACGGT-3' | SEQ ID NO:31 |
| PVS3-8 (-836) : F | 5'-CGGAATTCGTTATATAGTTTTTAAAAAAAA-3' | SEQ ID NO:32 |
| PVS3-9 (-584) : F | 5'-CGGAATTCGATTTATAACACGATGCGGGTG-3' | SEQ ID NO:33 |
| PVS3-10 (-332) : F | 5'-CGGAATTCTTACTATATATTAACTGTCCAC-3' | SEQ ID NO:34 |
| PVS3 : R | 5'-CCATCGATTCCTCTTCATTGTTAAAGGGGA-3' | SEQ ID NO:35 |

Fig. 29

```
-2648 ctcttctgttgatgtgctatagtcttttatatagcgctctattcatgttgtaatttggcc -2589
-2588 tctactttaattttttcaacctaaaccaacgtacaataatgtgtaatgatactaatttg   -2529
-2528 actcacataatagcatggtgctagaagagtcacttgaaagagtatactgaagagtattaa -2469
-2468 aaatataattctaaagaatttcgaagattcaattataattgatcaagaaggtgataagag -2409
-2408 ccttcnacaacaacgtaaagtttgggtagcctctatanatgactatgaaaatagccaaaa -2349
                         ──► pPVS3-1
-2348 aaaaattcaaattcgaattcttgtaatccttatttaggattattgcgaccatcacttgtg -2289
-2288 ggtgccttacttgactaaatatttgattaaacattaatttttggtcagtggatatacatg -2229
-2228 ccactcaattttaaataaattagtgatcccttacgatcttaaaaaaattgtattttgtg  -2169
-2168 tgtaatgtcaactttggttcaaatgtctaatataataagtattaattccaacagtattag -2109
-2108 aatttatttctaagatcactcttacggtcttaccactgaaagattaaaattctaaccaa  -2049
-2048 gaatttgaactttaaatagtacttatgaatttttacttgccgtttgaattttatgtacatg -1989
-1988 cttagaataattaggtcctcatgtagtcaactttaagaaaattacaatgttacgttctaa -1929
-1928 caagaacaaatttgactctagattttttaattttttttttttaaaaaaaaactaaatactc -1869
-1868 atccgattcaatttgtttgaaactatgttccaattattaatccgtttcaaaaacaatgtt -1809
-1808 acattcagatatttaaaatcaattaacttaaatttctcatcatcagtaagaagttttaat -1749
-1748 aatcacatgaaggaaagcctgtttggagaaagttatgcgtaaaatattgcatatatctct -1689
-1688 tccattgaattagttacatctggatttgcataaaatcaacatttagtaaaatacgatggc -1629
-1628 ttagatgattgaactttgaacaggaaaaataagcgtgcaaataagccatcaatcttgaac -1569
-1568 tttagaaatatatatatataattcaataagttactttattggaatagctatagtgacggc -1509
-1508 ggatttagaattttcattaaagggactctaaaaaaatatagtgcctaagatttgaacttg -1449
-1448 aaactcaagatgccactaaacaacctctaatcttacattcagaaggttcaaaatcaatat -1389
                                                    ──► pPVS3-2
-1388 atatagacataatttttttaaatttttttttaacctccctcgactacctctaggtccgccct -1329
                                       ──► pPVS3-3
-1328 tactattcccatccgatctcttgggaagcggggagaaattttataatagtgcactcat  -1269
                                    ──► pPVS3-4
-1268 gctataattacatactaagatttatgtaatgctatattttttcaagttgaagacggaaa  -1209
                         ──► pPVS3-5
-1208 caatagcattggatcaagacagacgccattgaaggaagaaaaaacctaaaaaaataaaca -1149
                     ──► pPVS3-6
-1148 aaaggagagacactttcttggtcccttcgaggccatatatcccattaatataaaaatata -1089
         ──► pPVS3-7
-1088 aaacaaaaaaaagacagacggtcgcccaaggaaagaaggcggacgtcactaacggctaa  -1029
-1028 ccctaactacaaataatgtaattttccaaaaacggaactataaggaataaaaaacatgaa  -969
 -968 gattattgagtattattaattttttaaaagacagacgccactcgaggaaataaggaatcac -909
 -908 aaggagtaaagaaagaaattaaaggcacgttacagtatcatataatataaatttaagttt  -849
                      ──► pPVS3-8
 -848 ggttgcattgaagttatatagttttaaaaaaaaataaaattgtccaacaatacttgtcc   -789
 -788 aatttagaaaatctaaaagataatttattattttgtgtttgttttacctcaacatctaat  -729
 -728 acatttctcaaattattaaatttaatatattcaaaaggtaatatagtaatattactctta  -669
 -668 ttatttatttattgtttcttaagatttgtgcaggtcaataataaaataactatcgttgaat -609
                              ──► pPVS3-9
 -608 taagggagtaccatcaaagaaattgatttataacacgatgcgggtggagggagctagaaa  -549
 -548 gttagtacaaatttggttgcactaagtacttcatccgtctcaatttatgagattttgttt  -489
 -488 gattcgagacgaaatttaataaagatgattttttaaagttgtaatctaaaacaagtcat   -429
 -428 aaatatttgcatcactataataatctcattaaatgtaaatgaatattttagctaaatta   -369
                                           ──► pPVS3-10
 -368 ttactactccctccatgtccatattagttgatcatcttactatatattaactgtccacct  -309
       CAAT box
 -308 tact[caat]aataaaatattaattaaagttttctatactagatataaaaatgttattat    -249
 -248 tatttttgataaagactagaaagagtatactatttgtatatctacagtgggacgaccagt  -189
 -188 taagtatattgtagtcaaagtaaggcaaccggatggactgcatgcagcacaaaggctctc  -129
       TATA box
 -128 accac[tataaata]tcaatattccttctctttcatttccatcaacaccttcaccaactaa    -69
  -68 caaattaaaagaaagaaaaaaaatctctcagtttcctcacaagctaattagacccgttt    -9
                 +1
   -8 ccgaagaaATGGCCCTAGCTATCCCCTTTAACAATGAAGAGGAGATTGTTCGCCCTGTTG   52
    1           M  A  L  A  I  P  F  N  N  E  E  E  I  V  R  P  V   17
```

Fig. 32
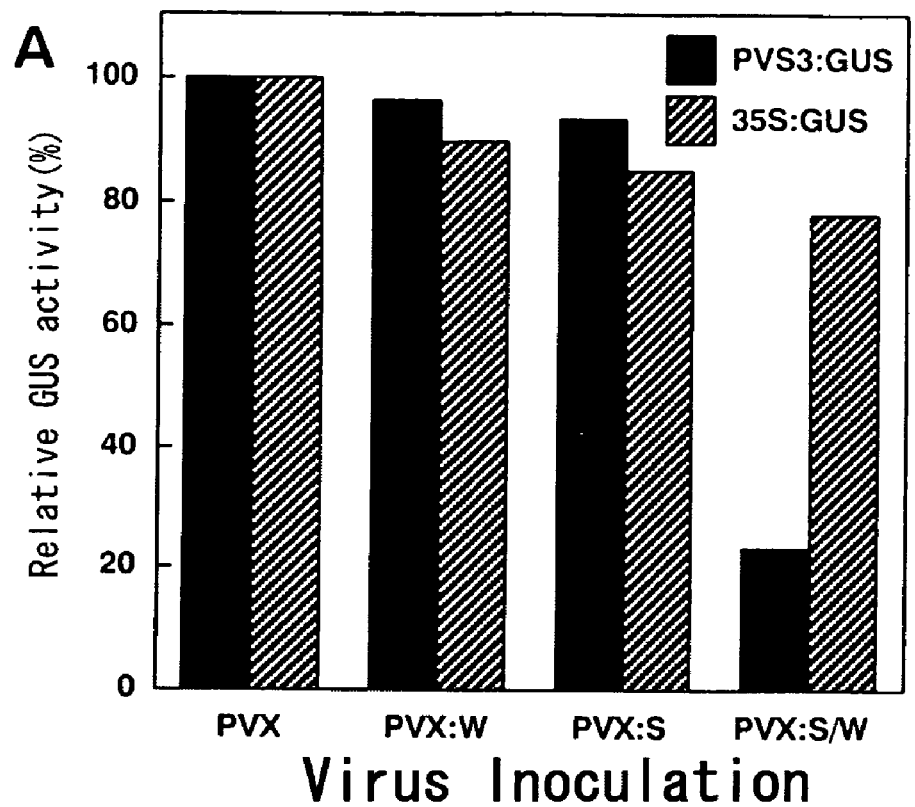
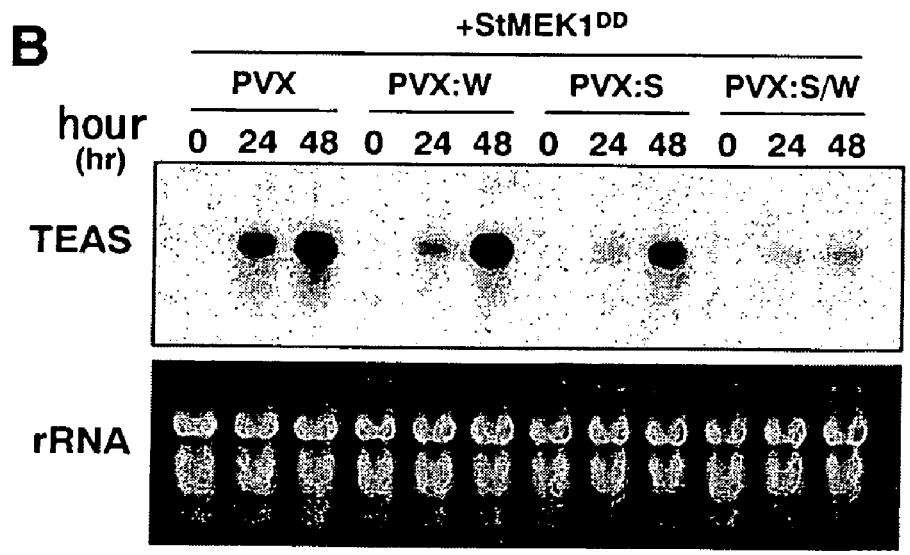

SEQUENCE LISTING

```
<160> NUMBER OF SEQ ID NOS: 47

<210> SEQ ID NO 1
<211> LENGTH: 2648
<212> TYPE: DNA
<213> ORGANISM: Solanum tuberosum
<220> FEATURE:
<221> NAME/KEY: modified_base
<222> LOCATION: (246)
<223> OTHER INFORMATION: a, c, g, t, unknown or other
<220> FEATURE:
<221> NAME/KEY: modified_base
<222> LOCATION: (278)
<223> OTHER INFORMATION: a, c, g, t, unknown or other

<400> SEQUENCE: 1
ctcttctgtt gatgtgctat agtcttttat atagcgctct attcatgttg taatttggcc      60
tctactttaa ttttttcaa cctaaaccaa cgtacaataa tgtgtaatga tactaatttg     120
actcacataa tagcatggtg ctagaagagt cacttgaaag agtatactga agagtattaa     180
aaatataatt ctaaagaatt tcgaagattc aattataatt gatcaagaag gtgataagag     240
ccttcnacaa caacgtaaag tttgggtagc ctctatanat gactatgaaa atagccaaaa     300
aaaaattcaa attcgaattc ttgtaatcct tatttaggat tattgcgacc atcacttgtg     360
ggtgccttac ttgactaaat atttgattaa acattaattt ttggtcagtg gatatacatg     420
ccactcaatt ttaaataaat tagtgatccc ttacgatctt aaaaaaattg tattttttgtg    480 tgtaatgtca actttggttc aaatgtctaa tataataagt attaattcca acagtattag     540
aattttattt ctaagatcac tcttacggtc ttaccactga aagattaaaa ttctaaccaa     600
gaatttgaac tttaaatagt acttatgaat tttacttgcc gtttgaattt tatgtacatg     660
```

```
cttagaataa ttaggtcctc atgtagtcaa ctttaagaaa attacaatgt tacgttctaa      720
caagaacaaa tttgactcta gatttttaat tttttttttt taaaaaaaaa ctaaatactc      780
atccgattca atttgtttga aactatgttc caattattaa tccgtttcaa aaacaatgtt      840
acattcagat atttaaaatc aattaactta aatttctcat catcagtaag aagttttaat      900
aatcacatga aggaaagcct gtttggagaa agttatgcgt aaaatattgc atatatctct      960
tccattgaat tagttacatc tggatttgca taaaatcaac atttagtaaa atacgatggc     1020
ttagatgatt gaactttgaa caggaaaaat aagcgtgcaa ataagccatc aatcttgaac     1080
tttagaaata tatatatata attcaataag ttactttatt ggaatagcta tagtgacggc     1140
ggatttagaa ttttcattaa agggactcta aaaaaatata gtgcctaaga tttgaacttg     1200
aaactcaaga tgccactaaa caacctctaa tcttacattc agaaggttca aaatcaatat     1260
atatagacat aattttttaa attttttttta acctccctcg actacctcta ggtccgccct     1320
tactattccc atccgatctc tgggaagcg ggggagaaaa ttttataata gtgcactcat      1380
gctataatta catactaaga ttttatgtaa tgctatattt tttcaagttg aagacggaaa     1440
caatagcatt ggatcaagac agacgccatt gaaggaagaa aaaacctaaa aaataaaaca     1500
aaaggagaga cactttcttg gtcccttcga ggccatatat cccattaata taaaaatata     1560
aaacaaaaaa aaagacagac ggtcgcccaa ggaaagaagg cggacgtcac taacggctaa     1620
ccctaactac aaataatgta attttccaaa aacggaacta taaggaataa aaaacatgaa     1680
gattattgag tattattaat ttttaaaaga cagacgccac tcgaggaaat aaggaatcac     1740
aaggagtaaa gaaagaaatt aaaggcacgt tacagtatca tataatataa atttaagttt     1800
ggttgcattg aagttatata gttttttaaaa aaaaataaaa ttgtccaaca atacttgtcc     1860
aatttagaaa atctaaaaga taatttatta ttttgtgttt gttttacctc aacatctaat     1920
acatttctca aattattaaa tttaatatat tcaaaaggta atatagtaat attactctta     1980
ttatttattt attgtttctt aagatttgtg caggtcaata ataaataact atcgttgaat     2040
taagggagta ccatcaaaga aattgattta taacacgatg cgggtggagg gagctagaaa     2100
gttagtacaa atttggttgc actaagtact tcatccgtct caatttatga gattttgttt     2160
gattcgagac gaaatttaat aaagatgatt ttttaaagt tgtaatctaa aacaagtcat      2220
aaatatttgc atcactataa taatctcatt aaatgtaaat gaatattttt agctaaatta     2280
ttactactcc ctccatgtcc atattagttg atcatcttac tatatattaa ctgtccacct     2340
tactcaatta ataaaatatt aattaaagtt tttctatact agatataaaa atgttattat     2400 tattttttgat aaagactaga aagagtatac tatttgtata tctacagtgg gacgaccagt     2460
taagtatatt gtagtcaaag taaggcaacc ggatggactg catgcagcac aaaggctctc     2520
accactataa atactcaata ttccttctct ttcatttcca tcaacacctt caccaactaa     2580
caaattaaaa gaaagaaaaa aaatctctc agtttcctca caagctaatt agacccgttt     2640
ccgaagaa                                                             2648
```

<210> SEQ ID NO 2
<211> LENGTH: 2000
<212> TYPE: DNA
<213> ORGANISM: Solanum tuberosum

<400> SEQUENCE: 2

```
tttatgtaca tgcttagaat aattaggtcc tcatgtagtc aactttaaga aaattacaat       60
gttacgttct aacaagaaca aatttgactc tagatttttta attttttttt tttaaaaaaa      120
```

```
aactaaatac tcatccgatt caatttgttt gaaactatgt tccaattatt aatccgtttc      180
aaaaacaatg ttacattcag atatttaaaa tcaattaact taaatttctc atcatcagta      240
agaagtttta ataatcacat gaaggaaagc ctgtttggag aaagttatgc gtaaaatatt      300
gcatatatct cttccattga attagttaca tctggatttg cataaaatca acatttagta      360
aaatacgatg gcttagatga ttgaactttg aacaggaaaa ataagcgtgc aaataagcca      420
tcaatcttga actttagaaa tatatatata taattcaata agttacttta ttggaatagc      480
tatagtgacg gcggatttag aattttcatt aaagggactc taaaaaaata tagtgcctaa      540
gatttgaact tgaaactcaa gatgccacta acaacctct aatcttacat tcagaaggtt       600
caaaatcaat atatatagac ataattttt aatttttt taacctccct cgactacctc         660
taggtccgcc cttactattc ccatccgatc tcttgggaag cggggagaa aattttataa       720 tagtgcactc atgctataat tacatactaa gatttatgt aatgctatat tttttcaagt       780
tgaagacgga acaatagca ttggatcaag acagacgcca ttgaaggaag aaaaaaccta       840
aaaaaataaa caaaggaga gacactttct tggtcccttc gaggccatat atcccattaa       900
tataaaaata taaaacaaaa aaaaagacag acggtcgccc aaggaaagaa ggcggacgtc      960
actaacggct aaccctaact acaaataatg taattttcca aaaacggaac tataaggaat     1020
aaaaaacatg aagattattg agtattatta attttttaaaa gacagacgcc actcgaggaa   1080
ataaggaatc acaaggagta aagaaagaaa ttaaaggcac gttacagtat catataaatat    1140 aaatttaagt ttggttgcat tgaagttata tagtttttaa aaaaaaataa aattgtccaa     1200
caatacttgt ccaatttaga aaatctaaaa gataatttat tattttgtgt ttgttttacc     1260
tcaacatcta atacatttct caaattatta aatttaatat attcaaaagg taatatagta    1320
atattactct tattatttat ttattgtttc ttaagatttg tgcaggtcaa taataaataa     1380
ctatcgttga attaagggag taccatcaaa gaaattgatt tataacacga tgcgggtgga    1440
gggagctaga aagttagtac aaatttggtt gcactaagta cttcatccgt ctcaatttat    1500
gagattttgt ttgattcgag acgaaattta ataaagatga ttttttttaaa gttgtaatct    1560 aaaacaagtc ataaatattt gcatcactat aataatctca ttaaatgtaa atgaatattt    1620
ttagctaaat tattactact ccctccatgt ccatatagt tgatcatctt actatatatt     1680
aactgtccac cttactcaat taataaaata ttaattaaag ttttctata ctagatataa     1740 aaatgttatt attattttg ataaagacta gaaagagtat actatttgta tatctacagt     1800
gggacgacca gttaagtata ttgtagtcaa agtaaggcaa ccggatggac tgcatgcagc    1860 acaaggctc tcaccactat aaatactcaa tattccttct ctttcatttc catcaacacc    1920
ttcaccaact aacaaattaa aagaaagaaa aaaaaatctc tcagtttcct cacaagctaa     1980
ttagacccgt ttccgaagaa                                                 2000
```

<210> SEQ ID NO 3
<211> LENGTH: 1500
<212> TYPE: DNA
<213> ORGANISM: Solanum tuberosum

<400> SEQUENCE: 3

```
aattttcatt aaagggactc taaaaaaata tagtgcctaa gatttgaact tgaaactcaa       60
gatgccacta acaacctct aatcttacat tcagaaggtt caaaatcaat atatatagac       120 ataattttt aatttttt taacctccct cgactacctc taggtccgcc cttactattc         180
```

-continued

```
ccatccgatc tcttgggaag cggggggagaa aattttataa tagtgcactc atgctataat      240
tacatactaa gattttatgt aatgctatat tttttcaagt tgaagacgga aacaatagca      300
ttggatcaag acagacgcca ttgaaggaag aaaaaaccta aaaaaataaa caaaggaga       360 gacactttct tggtcccttc gaggccatat atcccattaa tataaaaata taaacaaaa       420 aaaaagacag acggtcgccc aaggaaagaa ggcggacgtc actaacggct aaccctaact     480
acaaataatg taattttcca aaaacggaac tataaggaat aaaaaacatg aagattattg     540
agtattatta attttttaaaa gacagacgcc actcgaggaa ataaggaatc acaaggagta    600
aagaaagaaa ttaaaggcac gttacagtat catataaatat aaatttaagt ttggttgcat    660
tgaagttata tagtttttaa aaaaaaataa aattgtccaa caatacttgt ccaatttaga     720
aaatctaaaa gataatttat tattttgtgt ttgttttacc tcaacatcta atacatttct     780
caaattatta aatttaatat attcaaaagg taatatagta atattactct tattatttat    840
ttattgtttc ttaagatttg tgcaggtcaa taataaataa ctatcgttga attaagggag    900
taccatcaaa gaaattgatt tataacacga tgcgggtgga gggagctaga aagttagtac   960
aaatttggtt gcactaagta cttcatccgt ctcaatttat gagattttgt ttgattcgag  1020
acgaaattta ataaagatga ttttttttaaa gttgtaatct aaaacaagtc ataaatattt 1080
gcatcactat aataatctca ttaaatgtaa atgaatattt ttagctaaat tattactact  1140
ccctccatgt ccatattagt tgatcatctt actatatatt aactgtccac cttactcaat  1200
taataaaata ttaattaaag ttttttctata ctagatataa aaatgttatt attattttg    1260 ataaagacta gaaagagtat actatttgta tatctacagt gggacgacca gttaagtata 1320
ttgtagtcaa agtaaggcaa ccggatggac tgcatgcagc acaaaggctc tcaccactat 1380
aaatactcaa tattccttct ctttcatttc catcaacacc ttcaccaact aacaaattaa  1440
aagaaagaaa aaaaaatctc tcagtttcct cacaagctaa ttagacccgt ttccgaagaa 1500
```

<210> SEQ ID NO 4
<211> LENGTH: 1000
<212> TYPE: DNA
<213> ORGANISM: Solanum tuberosum

<400> SEQUENCE: 4

```
aaaacggaac tataaggaat aaaaaacatg aagattattg agtattatta attttttaaaa     60 gacagacgcc actcgaggaa ataaggaatc acaaggagta aagaaagaaa ttaaaggcac    120
gttacagtat catataaatat aaatttaagt ttggttgcat tgaagttata tagtttttaa   180
aaaaaaataa aattgtccaa caatacttgt ccaatttaga aaatctaaaa gataatttat   240
tattttgtgt ttgttttacc tcaacatcta atacatttct caaattatta aatttaatat   300
attcaaaagg taatatagta atattactct tattatttat ttattgtttc ttaagatttg   360
tgcaggtcaa taataaataa ctatcgttga attaagggag taccatcaaa gaaattgatt   420
tataacacga tgcgggtgga gggagctaga aagttagtac aaatttggtt gcactaagta   480
cttcatccgt ctcaatttat gagattttgt ttgattcgag acgaaattta ataaagatga   540 ttttttttaaa gttgtaatct aaaacaagtc ataaatattt gcatcactat aataatctca  600
ttaaatgtaa atgaatattt ttagctaaat tattactact ccctccatgt ccatattagt   660
tgatcatctt actatatatt aactgtccac cttactcaat taataaaata ttaattaaag   720 ttttttctata ctagatataa aaatgttatt attattttg ataaagacta gaaagagtat    780
actatttgta tatctacagt gggacgacca gttaagtata ttgtagtcaa agtaaggcaa   840
```

```
ccggatggac tgcatgcagc acaaaggctc tcaccactat aaatactcaa tattccttct    900
ctttcatttc catcaacacc ttcaccaact aacaaattaa agaaagaaa aaaaaatctc      960 tcagtttcct cacaagctaa ttagacccgt ttccgaagaa                          1000
```

<210> SEQ ID NO 5
<211> LENGTH: 1125
<212> TYPE: DNA
<213> ORGANISM: Solanum tuberosum

<400> SEQUENCE: 5

```
atgcgacctc ttcaaccacc cccaccagct gccaactcca cctcctccgc cgccgcatca     60
tccatgcctc ctcccctctt cgccggacaa cgcagtcgtc cccggcgtcg tactgatttg    120
acccttcctc ttcctcaacg tgacgttgct cttgctgttc ctctcccct tcctccaacc     180 tccgctcctt cctcttcctc atcctcatct tcctccccgc ttcctacccc tttacatttc    240
tctgagctcg agagggttaa tcgcatcggt agtggcaccg gaggtactgt ttacaaggtt    300
ctacatcgtc ccactggcag actctatgct ttgaaagtta tctatggtaa ccatgaggat    360
tctgtccgtc tccagatgtg ccgtgagatc gagattctcc gagatgtaga caaccctaac    420
gtcgttaggt gtcacgatat gttcgatcac aacggcgaaa tccaagttct tcttgagttc    480
atggataaag gctctctcga agggatccat atccctctcg aacaacctct ctccgatcta    540
actcgacagg ttctctccgg cctctactac ctccacaggc gtaagattgt tcacagagat    600
atcaaacctt ctaacctctt aatcaactcc aggcgtgagg tcaagattgc agattttggg    660
gtctccagag ttctcgcaca aactatggat ccttgcaatt cctccgtggg taccatcgct    720
tacatgagtc ccgagagaat caacacagat ctgaatcacg acagtacga cggatatgct    780 ggggacatat ggagtcttgg ggtgagcatc ttagagttct acttgggaag gttcccctc     840 tctgtgggga gacaaggaga ctgggccagc cttatgtgcg ccatttgtat gtcgcagcct    900
cctgaggcac cacccactgc ttccagggag tttagggagt tcattgcctg ctgtttgcag    960
agggatcctg ctaggcggtg gacggccgcg cagctcttgc gccatccctt catcacccag   1020
aatagcccag gcacccacac cggtcctgct actacctcat tgagtaatca ggcacatcaa   1080
ttgttacctc cacctcctca tttttcttct tcttcttctt cttga                   1125
```

<210> SEQ ID NO 6
<211> LENGTH: 374
<212> TYPE: PRT
<213> ORGANISM: Solanum tuberosum

<400> SEQUENCE: 6

```
Met Arg Pro Leu Gln Pro Pro Pro Ala Ala Asn Ser Thr Ser Ser
 1               5                  10                  15

Ala Ala Ala Ser Ser Met Pro Pro Ser Ser Ala Gly Gln Arg Ser
            20                  25                  30

Arg Pro Arg Arg Thr Asp Leu Thr Leu Pro Leu Pro Gln Arg Asp
        35                  40                  45

Val Ala Leu Ala Val Pro Leu Pro Leu Pro Thr Ser Ala Pro Ser
    50                  55                  60

Ser Ser Ser Ser Ser Ser Ser Pro Leu Thr Pro Leu His Phe
65                  70                  75                  80

Ser Glu Leu Glu Arg Val Asn Arg Ile Gly Ser Gly Thr Gly Gly Thr
                85                  90                  95
```

```
Val Tyr Lys Val Leu His Arg Pro Thr Gly Arg Leu Tyr Ala Leu Lys
                100                 105                 110

Val Ile Tyr Gly Asn His Glu Asp Ser Val Arg Leu Gln Met Cys Arg
            115                 120                 125

Glu Ile Glu Ile Leu Arg Asp Val Asp Asn Pro Asn Val Val Arg Cys
        130                 135                 140

His Asp Met Phe Asp His Asn Gly Glu Ile Gln Val Leu Leu Glu Phe
145                 150                 155                 160

Met Asp Lys Gly Ser Leu Glu Gly Ile His Ile Pro Leu Glu Gln Pro
                165                 170                 175

Leu Ser Asp Leu Thr Arg Gln Val Leu Ser Gly Leu Tyr Tyr Leu His
            180                 185                 190

Arg Arg Lys Ile Val His Arg Asp Ile Lys Pro Ser Asn Leu Leu Ile
        195                 200                 205

Asn Ser Arg Arg Glu Val Lys Ile Ala Asp Phe Gly Val Ser Arg Val
    210                 215                 220

Leu Ala Gln Thr Met Asp Pro Cys Asn Ser Ser Val Gly Thr Ile Ala
225                 230                 235                 240

Tyr Met Ser Pro Glu Arg Ile Asn Thr Asp Leu Asn His Gly Gln Tyr
                245                 250                 255

Asp Gly Tyr Ala Gly Asp Ile Trp Ser Leu Gly Val Ser Ile Leu Glu
            260                 265                 270

Phe Tyr Leu Gly Arg Phe Pro Phe Ser Val Gly Arg Gln Gly Asp Trp
        275                 280                 285

Ala Ser Leu Met Cys Ala Ile Cys Met Ser Gln Pro Pro Glu Ala Pro
    290                 295                 300

Pro Thr Ala Ser Arg Glu Phe Arg Glu Phe Ile Ala Cys Cys Leu Gln
305                 310                 315                 320

Arg Asp Pro Ala Arg Arg Trp Thr Ala Ala Gln Leu Leu Arg His Pro
                325                 330                 335

Phe Ile Thr Gln Asn Ser Pro Gly Thr His Thr Gly Pro Ala Thr Thr
            340                 345                 350

Ser Leu Ser Asn Gln Ala His Gln Leu Leu Pro Pro Pro His Phe
        355                 360                 365

Ser Ser Ser Ser Ser Ser
    370

<210> SEQ ID NO 7
<211> LENGTH: 1125
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
atgcgacctc ttcaaccacc cccaccagct gccaactcca cctcctccgc cgccgcatca     60
tccatgcctc ctccctcttc cgccggacaa cgcagtcgtc cccggcgtcg tactgatttg    120
acccttcctc ttcctcaacg tgacgttgct cttgctgttc ctctccccct tcctccaacc    180
tccgctcctt cctcttcctc atcctcatct tcctccccgc ttcctacccc tttacatttc    240
tctgagctcg agagggttaa tcgcatcggt agtggcaccg gaggtactgt ttacaaggtt    300
ctacatcgtc ccactggcag actctatgct ttgaaagtta tctatggtaa ccatgaggat    360
tctgtccgtc tccagatgtg ccgtgagatc gagattctcc gagatgtaga caaccctaac    420
```

```
gtcgttaggt gtcacgatat gttcgatcac aacggcgaaa tccaagttct tcttgagttc    480
atggataaag gctctctcga agggatccat atccctctcg aacaacctct ctccgatcta    540
actcgacagg ttctctccgg cctctactac ctccacaggc gtaagattgt tcacagagat    600
atcaaacctt ctaacctctt aatcaactcc aggcgtgagg tcaagattgc agattttggg    660
gtctccagag ttctcgcaca agatatggat ccttgcaatg actccgtggg taccatcgct    720
tacatgagtc ccgagagaat caacacagat ctgaatcacg acagtacga cggatatgct    780 ggggacatat ggagtcttgg ggtgagcatc ttagagttct acttgggaag gttccccttc    840
tctgtgggga gacaaggaga ctgggccagc cttatgtgcg ccatttgtat gtcgcagcct    900
cctgaggcac acccactgc ttccagggag tttagggagt tcattgcctg ctgtttgcag    960
agggatcctg ctaggcggtg gacggccgcg cagctcttgc gccatccctt catcacccag   1020
aatagcccag gcacccacac cggtcctgct actacctcat tgagtaatca ggcacatcaa   1080
ttgttacctc cacctcctca ttttttcttct tcttcttctt cttga                  1125
```

<210> SEQ ID NO 8
<211> LENGTH: 374
<212> TYPE: PRT
<213> ORGANISM: Artificial Sequence
<220> FEATURE:
<223> OTHER INFORMATION: Description of Artificial Sequence: Synthetic construct

<400> SEQUENCE: 8

```
Met Arg Pro Leu Gln Pro Pro Pro Ala Ala Asn Ser Thr Ser Ser
 1               5                  10                  15

Ala Ala Ala Ser Ser Met Pro Pro Ser Ser Ala Gly Gln Arg Ser
                20                  25                  30

Arg Pro Arg Arg Arg Thr Asp Leu Thr Leu Pro Leu Pro Gln Arg Asp
            35                  40                  45

Val Ala Leu Ala Val Pro Leu Pro Pro Thr Ser Ala Pro Ser
         50                  55                  60

Ser Ser Ser Ser Ser Ser Ser Pro Leu Pro Thr Pro Leu His Phe
 65                  70                  75                  80

Ser Glu Leu Glu Arg Val Asn Arg Ile Gly Ser Gly Thr Gly Thr
                 85                  90                  95

Val Tyr Lys Val Leu His Arg Pro Thr Gly Arg Leu Tyr Ala Leu Lys
                100                 105                 110

Val Ile Tyr Gly Asn His Glu Asp Ser Val Arg Leu Gln Met Cys Arg
            115                 120                 125

Glu Ile Glu Ile Leu Arg Asp Val Asp Asn Pro Asn Val Val Arg Cys
130                 135                 140

His Asp Met Phe Asp His Asn Gly Glu Ile Gln Val Leu Leu Glu Phe
145                 150                 155                 160

Met Asp Lys Gly Ser Leu Glu Gly Ile His Ile Pro Leu Glu Gln Pro
                165                 170                 175

Leu Ser Asp Leu Thr Arg Gln Val Leu Ser Gly Leu Tyr Tyr Leu His
            180                 185                 190

Arg Arg Lys Ile Val His Arg Asp Ile Lys Pro Ser Asn Leu Leu Ile
        195                 200                 205

Asn Ser Arg Arg Glu Val Lys Ile Ala Asp Phe Gly Val Ser Arg Val
    210                 215                 220

Leu Ala Gln Asp Met Asp Pro Cys Asn Asp Ser Val Gly Thr Ile Ala
225                 230                 235                 240
```

-continued

```
Tyr Met Ser Pro Glu Arg Ile Asn Thr Asp Leu Asn His Gly Gln Tyr
                245                 250                 255

Asp Gly Tyr Ala Gly Asp Ile Trp Ser Leu Gly Val Ser Ile Leu Glu
            260                 265                 270

Phe Tyr Leu Gly Arg Phe Pro Phe Ser Val Gly Arg Gln Gly Asp Trp
        275                 280                 285

Ala Ser Leu Met Cys Ala Ile Cys Met Ser Gln Pro Pro Glu Ala Pro
    290                 295                 300

Pro Thr Ala Ser Arg Glu Phe Arg Glu Phe Ile Ala Cys Cys Leu Gln
305                 310                 315                 320

Arg Asp Pro Ala Arg Arg Trp Thr Ala Ala Gln Leu Leu Arg His Pro
                325                 330                 335

Phe Ile Thr Gln Asn Ser Pro Gly Thr His Thr Gly Pro Ala Thr Thr
            340                 345                 350

Ser Leu Ser Asn Gln Ala His Gln Leu Leu Pro Pro Pro Pro His Phe
        355                 360                 365

Ser Ser Ser Ser Ser Ser
    370
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggagattgt tcgccccata                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctccatgag tccttacatg                                                   20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catcgattgt tttgtacatc tg                                                22

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aataatgata caaaaaaaaa ttaagg                                            26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tatcaattca ccaaggaaca ct                                          22

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gaagtaatta aatttaaata ttatcaa                                     27

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ttgtctgctg ctgcttgtgg                                             20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tctccatgag tccttacatg                                             20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aggacattgt tcgacctgtt                                             20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tctccatgag tccttacatg                                             20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcccttaa aattataagt attc                                              24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aataatgata caaaataaat taagg                                             25

<210> SEQ ID NO 21
<211> LENGTH: 2231
<212> TYPE: DNA
<213> ORGANISM: Solanum tuberosum

<400> SEQUENCE: 21
atggccctag ctatcccctt taacaatgaa gaggagattg ttcgccctgt tgccaatttc       60
tctccaagtc tttggggtga tcgtttccat tcattctctc tcgacaatca ggtaattact      120
taattaatta ctaattaaat ccttctctat cgcttatatt tggttaatta ctactaatcc      180
caatcatgaa cattttacag gttgctgaaa agtatgctca agagattgaa actttgaagg      240
aacaaacaag gagtttgttg tctgctgctg cttgtggaat aacattggct gagaaattga      300
atctgataga cattgttgag cgccttggct tagcttatca ttttgagaaa caaatagatg      360
atatgttgga tcaaatttac aaagcagatc ccaactttga cgctcatgat ttaaacactt      420
tatcccttca atttcgaata ttaagacaac atggttacaa tatctcccaa agtaggtcca      480
tcatttaaaa caattcacca aaataatacg ttttttttctg catgaaaact aattatcttt      540
tgcttttatt cgatcatgat ccagaatttt tcagcagatt ccaagatgcg aatggcaagt      600
tcaaggaatg tcttagcaac gacatcaggg gtctattgaa cttatacgaa gcttcacatg      660
taaggactca tggagaagat attttagaag aggcacttgt tttctccact gctcatcttg      720
agtctgcagc tccacatttg gagtcacctc tgagtaagca agtgactcat gcccttgagc      780
agtctctcca aagagcatt ccaagagtcg agacgcgcta cttcatctcc atctacgaag       840
aggaggaatt taagaatgat gtgttgcttc gatttgccaa attggattac aacttactcc      900
agatgttgca caaacacgaa cttagtgaag tatcaaggta tacagatgtg ttaagttgaa      960
ttaaaaatac tagtataaat tatttgttga tagtaattttc taagattggt acttattttg     1020
taggtggtgg aaagatttgg attttgtgac aacgcttcca tatgctaggg atagagcagt     1080
ggaatgttac ttttggacga tgggagtgta tgctgaacct caatactctc aggctcgtgt     1140
catccttgca aagactatag caatgatttc gatagtagat gacacattcg atgcttatgg     1200
aatagtaaaa gaacttgagg tctacaccga tgccatacaa aggtatggac ttgcctctcc     1260
aacagttcat ggatttatta gacgggaaac ttactaaatc tctttctgtt ttattaggtg     1320
ggatattagt caaattgatc gactcccaga atacatgaaa gttagtttta aggctctttt     1380

```
ggatctctat gaagattatg aaaaggagtt gtcaaaggat ggcagatccg atgttgtcca    1440
ctacgcaaaa gaaagagtag gactcactga tttctattta aaaacacttg tatttacctt    1500
atactatttc tttattatac aattagatct gttatgggag tattgatggt tgaatgtctt    1560
gtggtttctg ttaaacagat gaaggagatt gtgagaaact attttgtaga agcaaagtgg    1620
ttcattgagg gatatatgcc gcctgttcct gagtatctta gcaatgcatt agctaccagc    1680
acatattact tgctaactac aacatcctat tgggagtgaa gtcagcaac aaaggaagat    1740 tttgaatggt tggctacgaa ccctaaaatt cttgaagcca atgtgacatt atgccgagtt    1800
gttgatgaca tagcaacgta tgaggtaatt agcatcgcat tacactacat aaatcatctt    1860
ataatttaga gttacagtaa tttaatacaa attgatttca catacttata aatgaattat    1920
aattgccatt ccaggttgag aagggtaggg gccaaatcgc aacaggaatt gagtgttata    1980
tgagggatta tgacgtatca acagaagtag caatggaaaa attccaagag atggctgaga    2040
tagcatggaa ggatgtaaat gaaggaattc ttcgaccaac acctgtctct acagaaattc    2100
ttactcgcat tctcaatctt gctcgtatta tagatgtcac ttacaagcac aatcaagatg    2160
gatacactca tcccgaaaaa gttctaaaac ctcacatcat tgctttactg gtggactcca    2220
ttgagatcta a                                                        2231

<210> SEQ ID NO 22
<211> LENGTH: 1337
<212> TYPE: DNA
<213> ORGANISM: Solanum tuberosum

<400> SEQUENCE: 22
gtccgccctt actattccca tccgatctct tgggaagcgg gggagaaaat tttataatag    60
tgcactcatg ctataattac atactaagat tttatgtaat gctatatttt ttcaagttga    120
agacggaaac aatagcattg gatcaagaca acgccattg aaggaagaaa aaacctaaaa    180
aaataaacaa aaggagagac actttcttgg tcccttcgag gccatatatc ccattaatat    240
aaaaatataa aacaaaaaaa aagacagacg gtcgcccaag gaaagaaggc ggacgtcact    300
aacggctaac cctaactaca aataatgtaa ttttccaaaa acggaactat aaggaataaa    360
aaacatgaag attattgagt attattaatt tttaaaagac agacgccact cgaggaaata    420
aggaatcaca aggagtaaag aaagaaatta aaggcacgtt acagtatcat ataatataaa    480
tttaagtttg gttgcattga agttatatag tttttaaaaa aaataaaat tgtccaacaa    540 tacttgtcca atttagaaaa tctaaagat aatttattat tttgtgtttg ttttacctca    600
acatctaata catttctcaa attattaaat ttaatatatt caaaaggtaa tatagtaata    660
ttactcttat tatttattta ttgtttctta agatttgtgc aggtcaataa taaataacta    720
tcgttgaatt aagggagtac catcaaagaa attgatttat aacacgatgc gggtggaggg    780
agctagaaag ttagtacaaa tttggttgca ctaagtactt catccgtctc aatttatgag    840
attttgtttg attcgagacg aaatttaata aagatgattt ttttaaagtt gtaatctaaa    900
acaagtcata aatatttgca tcactataat aatctcatta aatgtaaatg aatatttta    960 gctaaattat tactactccc tccatgtcca tattagttga tcatcttact atatattaac    1020
tgtccacctt actcaattaa taaaatatta attaaagttt tctatacta gatataaaaa    1080 tgttattatt atttttgata aagactagaa agagtatact attttgtatat ctacagtggg    1140 acgaccagtt aagtatattg tagtcaaagt aaggcaaccg gatggactgc atgcagcaca    1200
```

```
aaggctctca ccactataaa tactcaatat tccttctctt tcatttccat caacaccttc    1260
accaactaac aaattaaaag aaagaaaaaa aaatctctca gtttcctcac aagctaatta    1320
gacccgtttc cgaagaa                                                  1337
```

<210> SEQ ID NO 23
<211> LENGTH: 50
<212> TYPE: DNA
<213> ORGANISM: Solanum tuberosum

<400> SEQUENCE: 23

```
gtccgccctt actattccca tccgatctct tgggaagcgg gggagaaaat               50
```

<210> SEQ ID NO 24
<211> LENGTH: 1288
<212> TYPE: DNA
<213> ORGANISM: Solanum tuberosum

<400> SEQUENCE: 24

```
ttttataata gtgcactcat gctataatta catactaaga ttttatgtaa tgctatatt    60 tttcaagttg aagacggaaa caatagcatt ggatcaagac agacgccatt gaaggaagaa   120
aaaacctaaa aaaataaaca aaaggagaga cactttcttg gtcccttcga ggccatatat   180
cccattaata taaaaatata aaacaaaaaa aaagacagac ggtcgcccaa ggaaagaagg   240
cggacgtcac taacggctaa ccctaactac aaataatgta attttccaaa aacggaacta   300
taaggaataa aaaacatgaa gattattgag tattattaat ttttaaaaga cagacgccac   360
tcgaggaaat aaggaatcac aaggagtaaa gaaagaaatt aaaggcacgt tacagtatca   420
tataatataa atttaagttt ggttgcattg aagttatata gtttttaaaa aaaaataaaa   480
ttgtccaaca atacttgtcc aatttagaaa atctaaaaga taattatta ttttgtgttt   540 gttttacctc aacatctaat acatttctca aattattaaa tttaatatat tcaaaaggta   600
atatagtaat attactctta ttatttattt attgtttctt aagatttgtg caggtcaata   660
ataaataact atcgttgaat taagggagta ccatcaaaga aattgattta taacacgatg   720
cgggtggagg gagctagaaa gttagtacaa atttggttgc actaagtact tcatccgtct   780
caatttatga gattttgttt gattcgagac gaaatttaat aaagatgatt ttttttaaagt   840 tgtaatctaa aacaagtcat aaatatttgc atcactataa taatctcatt aaatgtaaat   900
gaatattttt agctaaatta ttactactcc ctccatgtcc atattagttg atcatcttac   960
tatatattaa ctgtccacct tactcaatta ataaatatatt aattaaagtt tttctatact  1020
agatataaaa atgttattat tatttttgat aaagactaga aagagtatac tatttgtata  1080
tctacagtgg gacgaccagt taagtatatt gtagtcaaag taaggcaacc ggatggactg  1140
catgcagcac aaaggctctc accactataa atactcaata ttccttctct ttcatttcca  1200
tcaacacctt caccaactaa caaattaaaa gaaagaaaaa aaaatctctc agtttcctca  1260
caagctaatt agacccgttt ccgaagaa                                     1288
```

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
cggaattctt gtaatcctta tttaggatta         30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cggaattcgt ccgcccttac tattcccatc         30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cggaattctt tataatagtg cactcatgct         30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cggaattcgc tatattttt caagttgaag         30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cggaattcga cgccattgaa ggaagaaaaa         30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cggaattcac tttcttggtc ccttcgaggc         30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
cggaattcaa caaaaaaaaa gacagacggt         30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cggaattcgt tatatagttt ttaaaaaaaa      30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cggaattcga tttataacac gatgcgggtg      30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cggaattctt actatatatt aactgtccac      30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ccatcgattc ctcttcattg ttaaagggga      30

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ttgggcccat gcgacctctt caaccacc      28

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gactagtaca aaagagtgtg gaattac      27

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcgacgaca cagccacgta cgaggt                                          26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atcgatagac tttctccgga tgagtg                                          26

<210> SEQ ID NO 40
<211> LENGTH: 5236
<212> TYPE: DNA
<213> ORGANISM: Solanum tuberosum
<220> FEATURE:
<221> NAME/KEY: CDS
<222> LOCATION: (2649)..(2759)
<220> FEATURE:
<221> NAME/KEY: CDS
<222> LOCATION: (2849)..(3119)
<220> FEATURE:
<221> NAME/KEY: CDS
<222> LOCATION: (3213)..(3585)
<220> FEATURE:
<221> NAME/KEY: CDS
<222> LOCATION: (3672)..(3890)
<220> FEATURE:
<221> NAME/KEY: CDS
<222> LOCATION: (3966)..(4104)
<220> FEATURE:
<221> NAME/KEY: CDS
<222> LOCATION: (4227)..(4472)
<220> FEATURE:
<221> NAME/KEY: CDS
<222> LOCATION: (4583)..(4876)
<220> FEATURE:
<221> NAME/KEY: modified_base
<222> LOCATION: (246)
<223> OTHER INFORMATION: a, c, g, t, unknown or other
<220> FEATURE:
<221> NAME/KEY: modified_base
<222> LOCATION: (278)
<223> OTHER INFORMATION: a, c, g, t, unknown or other

<400> SEQUENCE: 40
ctcttctgtt gatgtgctat agtcttttat atagcgctct attcatgttg taatttggcc     60
tctactttaa tttttttcaa cctaaaccaa cgtacaataa tgtgtaatga tactaatttg    120
actcacataa tagcatggtg ctagaagagt cacttgaaag agtatactga agagtattaa    180
aaatataatt ctaaagaatt tcgaagattc aattataatt gatcaagaag gtgataagag    240
ccttcnacaa caacgtaaag tttgggtagc ctctatanat gactatgaaa atagccaaaa    300
aaaaattcaa attcgaattc ttgtaatcct tatttaggat tattgcgacc atcacttgtg    360
ggtgccttac ttgactaaat atttgattaa acattaattt ttggtcagtg gatatacatg    420
ccactcaatt ttaaataaat tagtgatccc ttacgatctt aaaaaaattg tattttgtg     480

```
tgtaatgtca actttggttc aaatgtctaa tataataagt attaattcca acagtattag    540
aattttattt ctaagatcac tcttacggtc ttaccactga aagattaaaa ttctaaccaa    600
gaatttgaac tttaaatagt acttatgaat tttacttgcc gtttgaattt tatgtacatg    660
cttagaataa ttaggtcctc atgtagtcaa ctttaagaaa attacaatgt tacgttctaa    720
caagaacaaa tttgactcta gatttttaat tttttttttt taaaaaaaaa ctaaatactc    780
atccgattca atttgtttga aactatgttc caattattaa tccgtttcaa aaacaatgtt    840
acattcagat atttaaaatc aattaactta aatttctcat catcagtaag aagttttaat    900
aatcacatga aggaaagcct gtttggagaa agttatgcgt aaaatattgc atatatctct    960
tccattgaat tagttacatc tggatttgca taaaatcaac atttagtaaa atacgatggc   1020
ttagatgatt gaactttgaa caggaaaaat aagcgtgcaa ataagccatc aatcttgaac   1080
tttagaaata tatatatata attcaataag ttactttatt ggaatagcta tagtgacggc   1140
ggatttagaa ttttcattaa agggactcta aaaaaatata gtgcctaaga tttgaacttg   1200
aaactcaaga tgccactaaa caacctctaa tcttacattc agaaggttca aaatcaatat   1260
atatagacat aattttttaa atttttttta acctccctcg actacctcta ggtccgccct   1320
tactattccc atccgatctc ttgggaagcg ggggagaaaa ttttataata gtgcactcat   1380
gctataatta catactaaga ttttatgtaa tgctatattt tttcaagttg aagacggaaa   1440
caatagcatt ggatcaagac agacgccatt gaaggaagaa aaaacctaaa aaaataaaca   1500
aaaggagaga cactttcttg gtcccttcga ggccatatat cccattaata taaaaatata   1560
aaacaaaaaa aaagacagac ggtcgcccaa ggaaagaagg cggacgtcac taacggctaa   1620
ccctaactac aaataatgta attttccaaa aacggaacta aaggaataaa aaacatgaa    1680 gattattgag tattattaat ttttaaaaga cagacgccac tcgaggaaat aaggaatcac   1740
aaggagtaaa gaaagaaatt aaaggcacgt tacagtatca tataatataa atttaagttt   1800
ggttgcattg aagttatata gttttttaaaa aaaaataaaa ttgtccaaca atacttgtcc   1860
aatttagaaa atctaaaaga taatttatta ttttgtgttt gttttacctc aacatctaat   1920
acatttctca aattattaaa tttaatatat tcaaaggta atatagtaat attactctta   1980
ttatttattt attgtttctt aagatttgtg caggtcaata ataaataact atcgttgaat   2040
taagggagta ccatcaaaga aattgattta taacacgatg cgggtggagg gagctagaaa   2100
gttagtacaa atttggttgc actaagtact tcatccgtct caatttatga gattttgttt   2160
gattcgagac gaaatttaat aaagatgatt ttttaaagt tgtaatctaa aacaagtcat    2220
aaatatttgc atcactataa taatctcatt aaatgtaaat gaatattttt agctaaatta   2280
ttactactcc ctccatgtcc atattagttg atcatcttac tatatattaa ctgtccacct   2340
tactcaatta ataaaatatt aattaaagtt tttctatact agatataaaa atgttattat   2400
tatttttgat aaagactaga aagagtatac tatttgtata tctacagtgg gacgaccagt   2460
taagtatatt gtagtcaaag taaggcaacc ggatggactg catgcagcac aaaggctctc   2520
accactataa atactcaata ttccttctct ttcatttcca tcaacaccct caccaactaa   2580
caaattaaaa gaaagaaaaa aaatctctc agtttcctca aagctaatt agacccgttt    2640 ccgaagaa atg gcc cta gct atc ccc ttt aac aat gaa gag gag att gtt    2690
         Met Ala Leu Ala Ile Pro Phe Asn Asn Glu Glu Glu Ile Val
          1               5                  10 cgc cct gtt gcc aat ttc tct cca agt ctt tgg ggt gat cgt ttc cat     2738
Arg Pro Val Ala Asn Phe Ser Pro Ser Leu Trp Gly Asp Arg Phe His
 15                  20                  25                  30
```

-continued

```
tca ttc tct ctc gac aat cag gtaattactt aattaattac taattaaatc          2789
Ser Phe Ser Leu Asp Asn Gln
                35 cttctctatc gcttatattt ggttaattac tactaatccc aatcatgaac attttacag      2848 gtt gct gaa aag tat gct caa gag att gaa act ttg aag gaa caa aca       2896
Val Ala Glu Lys Tyr Ala Gln Glu Ile Glu Thr Leu Lys Glu Gln Thr
        40                  45                  50 agg agt ttg ttg tct gct gct gct tgt gga ata aca ttg gct gag aaa       2944
Arg Ser Leu Leu Ser Ala Ala Ala Cys Gly Ile Thr Leu Ala Glu Lys
    55                  60                  65 ttg aat ctg ata gac att gtt gag cgc ctt ggc tta gct tat cat ttt       2992
Leu Asn Leu Ile Asp Ile Val Glu Arg Leu Gly Leu Ala Tyr His Phe
70                  75                  80                  85 gag aaa caa ata gat gat atg ttg gat caa att tac aaa gca gat ccc       3040
Glu Lys Gln Ile Asp Asp Met Leu Asp Gln Ile Tyr Lys Ala Asp Pro
                90                  95                 100 aac ttt gac gct cat gat tta aac act tta tcc ctt caa ttt cga ata       3088
Asn Phe Asp Ala His Asp Leu Asn Thr Leu Ser Leu Gln Phe Arg Ile
            105                 110                 115 tta aga caa cat ggt tac aat atc tcc caa a gtaggtccat catttaaaac       3139
Leu Arg Gln His Gly Tyr Asn Ile Ser Gln
        120                 125 aattcaccaa aataatacgt ttttttctgc atgaaaacta attatctttt gcttttattc     3199
gatcatgatc cag aa ttt ttc agc aga ttc caa gat gcg aat ggc aag ttc    3250
                Lys Phe Phe Ser Arg Phe Gln Asp Ala Asn Gly Lys Phe
                    130                 135                 140 aag gaa tgt ctt agc aac gac atc agg ggt cta ttg aac tta tac gaa       3298
Lys Glu Cys Leu Ser Asn Asp Ile Arg Gly Leu Leu Asn Leu Tyr Glu
                145                 150                 155 gct tca cat gta agg act cat gga gaa gat att tta gaa gag gca ctt       3346
Ala Ser His Val Arg Thr His Gly Glu Asp Ile Leu Glu Glu Ala Leu
            160                 165                 170 gtt ttc tcc act gct cat ctt gag tct gca gct cca cat ttg gag tca       3394
Val Phe Ser Thr Ala His Leu Glu Ser Ala Ala Pro His Leu Glu Ser
        175                 180                 185 cct ctg agt aag caa gtg act cat gcc ctt gag cag tct ctc cat aag       3442
Pro Leu Ser Lys Gln Val Thr His Ala Leu Glu Gln Ser Leu His Lys
    190                 195                 200 agc att cca aga gtc gag acg cgc tac ttc atc tcc atc tac gaa gag       3490
Ser Ile Pro Arg Val Glu Thr Arg Tyr Phe Ile Ser Ile Tyr Glu Glu
205                 210                 215                 220 gag gaa ttt aag aat gat gtg ttg ctt cga ttt gcc aaa ttg gat tac       3538
Glu Glu Phe Lys Asn Asp Val Leu Leu Arg Phe Ala Lys Leu Asp Tyr
                225                 230                 235 aac tta ctc cag atg ttg cac aaa cac gaa ctt agt gaa gta tca ag        3585
Asn Leu Leu Gln Met Leu His Lys His Glu Leu Ser Glu Val Ser Arg
            240                 245                 250 gtatacagat gtgttaagtt gaattaaaaa tactagtata aattatttgt tgatagtaat    3645
ttctaagatt ggtacttatt ttgtag g tgg tgg aaa gat ttg gat ttt gtg       3696
                              Trp Trp Lys Asp Leu Asp Phe Val
                                          255                 260 aca acg ctt cca tat gct agg gat aga gca gtg aat gt tac ttt tgg       3744
Thr Thr Leu Pro Tyr Ala Arg Asp Arg Ala Val Glu Cys Tyr Phe Trp
                265                 270                 275 acg atg gga gtg tat gct gaa cct caa tac tct cag gct cgt gtc atc      3792
Thr Met Gly Val Tyr Ala Glu Pro Gln Tyr Ser Gln Ala Arg Val Ile
            280                 285                 290
```

```
ctt gca aag act ata gca atg att tcg ata gta gat gac aca ttc gat      3840
Leu Ala Lys Thr Ile Ala Met Ile Ser Ile Val Asp Asp Thr Phe Asp
        295                 300                 305 gct tat gga ata gta aaa gaa ctt gag gtc tac acc gat gcc ata caa      3888
Ala Tyr Gly Ile Val Lys Glu Leu Glu Val Tyr Thr Asp Ala Ile Gln
        310                 315                 320 ag gtatggactt gcctctccaa cagttcatgg atttattaga cgggaaactt            3940
Arg
325 actaaatctc tttctgtttt attag g tgg gat att agt caa att gat cga ctc    3993
                            Trp Asp Ile Ser Gln Ile Asp Arg Leu
                                            330 cca gaa tac atg aaa gtt agt ttt aag gct ctt ttg gat ctc tat gaa      4041
Pro Glu Tyr Met Lys Val Ser Phe Lys Ala Leu Leu Asp Leu Tyr Glu
335                 340                 345                 350 gat tat gaa aag gag ttg tca aag gat ggc aga tcc gat gtt gtc cac      4089
Asp Tyr Glu Lys Glu Leu Ser Lys Asp Gly Arg Ser Asp Val Val His
                355                 360                 365 tac gca aaa gaa aga gtaggactca ctgatttcta tttaaaaaca cttgtattta      4144
Tyr Ala Lys Glu Arg
            370 ccttatacta tttctttatt atacaattag atctgttatg ggagtattga tggttgaatg    4204 tcttgtggtt tctgttaaac ag atg aag gag att gtg aga aac tat ttt gta     4256
                         Met Lys Glu Ile Val Arg Asn Tyr Phe Val
                                     375                 380 gaa gca aag tgg ttc att gag gga tat atg ccg cct gtt tct gag tat      4304
Glu Ala Lys Trp Phe Ile Glu Gly Tyr Met Pro Pro Val Ser Glu Tyr
        385                 390                 395 ctt agc aat gca tta gct acc agc aca tat tac ttg cta act aca aca      4352
Leu Ser Asn Ala Leu Ala Thr Ser Thr Tyr Tyr Leu Leu Thr Thr Thr
        400                 405                 410 tcc tat ttg gga gtg aag tca gca aca aag gaa gat ttt gaa tgg ttg      4400
Ser Tyr Leu Gly Val Lys Ser Ala Thr Lys Glu Asp Phe Glu Trp Leu
        415                 420                 425 gct acg aac cct aaa att ctt gaa gcc aat gtg aca tta tgc cga gtt      4448
Ala Thr Asn Pro Lys Ile Leu Glu Ala Asn Val Thr Leu Cys Arg Val
430                 435                 440                 445 gtt gat gac ata gca acg tat gag gtaattagca tcgcattaca ctacataaat     4502
Val Asp Asp Ile Ala Thr Tyr Glu
                450 catcttataa tttagagtta cagtaattta atacaaattg atttcacata cttataaatg    4562 aattataatt gccattccag gtt gag aag ggt agg ggc caa atc gca aca gga    4615
                      Val Glu Lys Gly Arg Gly Gln Ile Ala Thr Gly
                                      455                 460 att gag tgt tat atg agg gat tat gac gta tca aca gaa gta gca atg      4663
Ile Glu Cys Tyr Met Arg Asp Tyr Asp Val Ser Thr Glu Val Ala Met
465                 470                 475                 480 gaa aaa ttc caa gag atg gct gag ata gca tgg aag gat gta aat gaa      4711
Glu Lys Phe Gln Glu Met Ala Glu Ile Ala Trp Lys Asp Val Asn Glu
                485                 490                 495 gga att ctt cga cca aca cct gtc tct aca gaa att ctt act cgc att      4759
Gly Ile Leu Arg Pro Thr Pro Val Ser Thr Glu Ile Leu Thr Arg Ile
            500                 505                 510 ctc aat ctt gct cgt att ata gat gtc act tac aag cac aat caa gat      4807
Leu Asn Leu Ala Arg Ile Ile Asp Val Thr Tyr Lys His Asn Gln Asp
        515                 520                 525 gga tac act cat ccc gaa aaa gtt cta aaa cct cac atc att gct tta      4855
Gly Tyr Thr His Pro Glu Lys Val Leu Lys Pro His Ile Ile Ala Leu
        530                 535                 540
```

```
ctg gtg gac tcc att gag atc taaaaattta gtaaatttta attttaaaa      4906
Leu Val Asp Ser Ile Glu Ile
545                 550 tgttacgtaa aaataataa accgtaaaaa taatgaagat taaggcgaac gaaccacgtg   4966
aggcggaaac gttgagaatg gatgatggaa aatagatgaa tatattgtta tgcatgaagg   5026
gtgtttcaca ctcttttgat tttgggaatg catggacatc cgcatgttgt cgactacacc   5086
tcgaccaatg ttgcgcaagc cacggccgat gcgggcaggc cacggatgac cgttgtgtgc   5146
agtccaaggg cgatgcggcc aggccacggc cgatgtcgac tgaccgttgt gtgcagtcca   5206
agggcgatgc gggcaggcca cgtccgacgt                                    5236

<210> SEQ ID NO 41
<211> LENGTH: 551
<212> TYPE: PRT
<213> ORGANISM: Solanum tuberosum

<400> SEQUENCE: 41

Met Ala Leu Ala Ile Pro Phe Asn Asn Glu Glu Glu Ile Val Arg Pro
1               5                   10                  15

Val Ala Asn Phe Ser Pro Ser Leu Trp Gly Asp Arg Phe His Ser Phe
                20                  25                  30

Ser Leu Asp Asn Gln Val Ala Glu Lys Tyr Ala Gln Glu Ile Glu Thr
            35                  40                  45

Leu Lys Glu Gln Thr Arg Ser Leu Leu Ser Ala Ala Cys Gly Ile
        50                  55                  60

Thr Leu Ala Glu Lys Leu Asn Leu Ile Asp Ile Val Glu Arg Leu Gly
65                  70                  75                  80

Leu Ala Tyr His Phe Glu Lys Gln Ile Asp Asp Met Leu Asp Gln Ile
                85                  90                  95

Tyr Lys Ala Asp Pro Asn Phe Asp Ala His Asp Leu Asn Thr Leu Ser
            100                 105                 110

Leu Gln Phe Arg Ile Leu Arg Gln His Gly Tyr Asn Ile Ser Gln Lys
        115                 120                 125

Phe Phe Ser Arg Phe Gln Asp Ala Asn Gly Lys Phe Lys Glu Cys Leu
    130                 135                 140

Ser Asn Asp Ile Arg Gly Leu Leu Asn Leu Tyr Glu Ala Ser His Val
145                 150                 155                 160

Arg Thr His Gly Glu Asp Ile Leu Glu Glu Ala Leu Val Phe Ser Thr
                165                 170                 175

Ala His Leu Glu Ser Ala Ala Pro His Leu Glu Ser Pro Leu Ser Lys
            180                 185                 190

Gln Val Thr His Ala Leu Glu Gln Ser Leu His Lys Ser Ile Pro Arg
        195                 200                 205

Val Glu Thr Arg Tyr Phe Ile Ser Ile Tyr Glu Glu Glu Phe Lys
    210                 215                 220

Asn Asp Val Leu Leu Arg Phe Ala Lys Leu Asp Tyr Asn Leu Leu Gln
225                 230                 235                 240

Met Leu His Lys His Glu Leu Ser Glu Val Ser Arg Trp Trp Lys Asp
                245                 250                 255

Leu Asp Phe Val Thr Thr Leu Pro Tyr Ala Arg Asp Arg Ala Val Glu
            260                 265                 270

Cys Tyr Phe Trp Thr Met Gly Val Tyr Ala Glu Pro Gln Tyr Ser Gln
        275                 280                 285
```

```
Ala Arg Val Ile Leu Ala Lys Thr Ile Ala Met Ile Ser Ile Val Asp
    290                 295                 300

Asp Thr Phe Asp Ala Tyr Gly Ile Val Lys Glu Leu Glu Val Tyr Thr
305                 310                 315                 320

Asp Ala Ile Gln Arg Trp Asp Ile Ser Gln Ile Asp Arg Leu Pro Glu
                325                 330                 335

Tyr Met Lys Val Ser Phe Lys Ala Leu Leu Asp Leu Tyr Glu Asp Tyr
            340                 345                 350

Glu Lys Glu Leu Ser Lys Asp Gly Arg Ser Asp Val Val His Tyr Ala
        355                 360                 365

Lys Glu Arg Met Lys Glu Ile Val Arg Asn Tyr Phe Val Glu Ala Lys
    370                 375                 380

Trp Phe Ile Glu Gly Tyr Met Pro Pro Val Ser Glu Tyr Leu Ser Asn
385                 390                 395                 400

Ala Leu Ala Thr Ser Thr Tyr Tyr Leu Leu Thr Thr Thr Ser Tyr Leu
                405                 410                 415

Gly Val Lys Ser Ala Thr Lys Glu Asp Phe Glu Trp Leu Ala Thr Asn
            420                 425                 430

Pro Lys Ile Leu Glu Ala Asn Val Thr Leu Cys Arg Val Val Asp Asp
        435                 440                 445

Ile Ala Thr Tyr Glu Val Glu Lys Gly Arg Gly Gln Ile Ala Thr Gly
    450                 455                 460

Ile Glu Cys Tyr Met Arg Asp Tyr Asp Val Ser Thr Glu Val Ala Met
465                 470                 475                 480

Glu Lys Phe Gln Glu Met Ala Glu Ile Ala Trp Lys Asp Val Asn Glu
                485                 490                 495

Gly Ile Leu Arg Pro Thr Pro Val Ser Thr Glu Ile Leu Thr Arg Ile
            500                 505                 510

Leu Asn Leu Ala Arg Ile Ile Asp Val Thr Tyr Lys His Asn Gln Asp
        515                 520                 525

Gly Tyr Thr His Pro Glu Lys Val Leu Lys Pro His Ile Ile Ala Leu
    530                 535                 540

Leu Val Asp Ser Ile Glu Ile
545                 550

<210> SEQ ID NO 42
<211> LENGTH: 40
<212> TYPE: DNA
<213> ORGANISM: Solanum tuberosum
<220> FEATURE:
<221> NAME/KEY: CDS
<222> LOCATION: (5)..(40)

<400> SEQUENCE: 42 agaa atg gcc cta gct atc ccc ttt aac aat gcc atg gaa           40
     Met Ala Leu Ala Ile Pro Phe Asn Asn Ala Met Glu
     1               5                   10

<210> SEQ ID NO 43
<211> LENGTH: 12
<212> TYPE: PRT
<213> ORGANISM: Solanum tuberosum

<400> SEQUENCE: 43

Met Ala Leu Ala Ile Pro Phe Asn Asn Ala Met Glu
1               5                   10

<210> SEQ ID NO 44
```

-continued

```
<211> LENGTH: 61
<212> TYPE: DNA
<213> ORGANISM: Solanum tuberosum
<220> FEATURE:
<221> NAME/KEY: CDS
<222> LOCATION: (5)..(61)

<400> SEQUENCE: 44 agaa atg gcc cta gct atc ccc ttt aac aat gaa gga tcc ccg ggt ggt      49
     Met Ala Leu Ala Ile Pro Phe Asn Asn Glu Gly Ser Pro Gly Gly
      1               5                  10                  15 cag tcc ctt atg                                                       61
Gln Ser Leu Met <210> SEQ ID NO 45
<211> LENGTH: 19
<212> TYPE: PRT
<213> ORGANISM: Solanum tuberosum

<400> SEQUENCE: 45

Met Ala Leu Ala Ile Pro Phe Asn Asn Glu Gly Ser Pro Gly Gly Gln
 1               5                  10                  15

Ser Leu Met

<210> SEQ ID NO 46
<211> LENGTH: 64
<212> TYPE: DNA
<213> ORGANISM: Solanum tuberosum
<220> FEATURE:
<221> NAME/KEY: CDS
<222> LOCATION: (5)..(64)

<400> SEQUENCE: 46 agaa atg gcc cta gct atc ccc ttt aac aat gaa gag gaa tcg atg ggt      49
     Met Ala Leu Ala Ile Pro Phe Asn Asn Glu Glu Glu Ser Met Gly
      1               5                  10                  15 cag tcc ctt atg tta                                                   64
Gln Ser Leu Met Leu
                20

<210> SEQ ID NO 47
<211> LENGTH: 20
<212> TYPE: PRT
<213> ORGANISM: Solanum tuberosum

<400> SEQUENCE: 47

Met Ala Leu Ala Ile Pro Phe Asn Asn Glu Glu Glu Ser Met Gly Gln
 1               5                  10                  15

Ser Leu Met Leu
            20
```

GERM-RESPONSIVE PROMOTER

TECHNICAL FIELD

The present invention relates to a promoter that is responsive to pathogen, and also to pathogen-resistant plants utilizing the promoter.

BACKGROUND ART

There lies an apparent race-specific parasitogenesis between potato *Phytophthora* infestants and potato plants. Such a specific relationship between a host and a pathogen is typically determined by the combination of avirulent genes contained in the pathogen and true resistant genes contained in the host. Dynamic resistance response is induced in the host when it is experiencing infection with an incompatible race. Specifically, production of reactive oxygen species, death of hypersensitive cell, production of phytoalexins (for potatoes, rishitin), expression of PR (Pathogenesis-Related) protein, formation of papilla, lignification and other resistance responses are triggered in the infected tissue, thereby arresting further development of the pathogen (See references 15, 32, 44, 45, and 47). In contrast, these resistance responses fail in the process of infection with a compatible race, allowing pathogen penetration and resulting in lethal, systemic infectious disease of potato.

One of the most important and local resistance responses among the dynamic resistance responses referred to above is thought to be accumulation of phytoalexin. Phytoalexins are small molecule compounds with microbiocidal action induced to accumulate upon pathogen infection, and has been indicated to be a crucial element in successful infection (See references 12, 13, 21, 28, and 46). Phytoalexins for potato are sesquiterpenoid compounds that are synthesized in isoprenoid metabolic system (FIG. 1).

It is known that isoprenoid synthesis in potato is rapidly converted from that for sterol/glycoalkaloid synthesis to that for sesquiterpenoid phytoalexin synthesis upon treatment with elicitor or inoculation of any incompatible race. This phenomenon is thought to be regulated by squalene synthase and sesquiterpene cyclase that act coordinately in the rate-limiting step of isoprenoid synthesis system to diverge the pathway into sterol glycoalkaroid synthesis and isoprenoid phytoalexin synthesis, respectively (See reference 8). Sesquiterpene cyclase for potato is vetispiradiene synthase and designated as potato vetispiradiene synthase (PVS) (See Reference 53). It has been reported that the PVS activity in potato tuber is significantly increased by inoculating pathogen or treating with HWC, which is derived from potato pathogen (See Reference 54). In addition, it is known that such an elicitor treatment leads to activation of sesquiterpenoid synthesis pathway also in tobacco plants, resulting in production of capsidiol, a type of phytoalexin (See References 42 and 48). Recently, these phenomena have been elucidated at the level of gene expression. As a result of Northern analysis of RNA extract from potato tuber using cDNA of PVS and squalene synthase isolated from potato as probes, it was found that PVS mRNA was temporarily induced to accumulate in the area where compatible and incompatible races had been inoculated. On the other hand, it has been shown that accumulation of mRNA for squalene synthase induced in the area of wound is suppressed by inoculation with compatible and incompatible races (See Reference 53). However, this report is not consistent with the observation that only the inoculation with incompatible race leads to biosynthesis of phytoalexin to arrest development of pathogen (See Reference 40).

It is generally known that most of plant genes constitute multigene families, with each isogene having discrete organ specificity and metabolic action in response to stimuli. It has been reported that PVS genes in potato plants also constitute multigene families having PVS 1 through 4 members (See Reference 53). Details of their behavior in expression are yet to be known.

REFERENCES (Reference 1)
Altschul, S. F., Gish, W., Miller, W., Myers, E. W. and Lipman, D. J. (1990) Basic local alignment search tool. J. Mol. Biol. 215, 403-410.

(Reference 2)
Arumuganathan, K. and Earle, E. D. (1991) Nuclear DNA content of some important plant species. Plant Mol. Biol. Reporter 9, 208-218.

(Reference 3)
Back, K. and Chappel, J. (1995) Cloning and bacterial expression of a sesquiterpene cyclase from *Hyoscyamus muticus* and its molecular comparison to rerated terpene cyclases. J. Biol. Chem. 270, 7375-7381.

(Reference 4)
Back, K. and Chappel, J. (1996) Identifying functional domains within terpene cyclase using domain-swapping strategy. Proc. Natl. Acad. Sci. USA 93, 6841-6845.

(Reference 5)
Back, K. and Chappel, J. (1998) Cloning and bacterial expression of a sesquiterpene cyclase, a key branch point enzyme for the synthesis of sesquiterpenoid phytoalexin capsidiol in UV-changed leaves of Capsium annum. Plant Cell Physiol. 39, 899-904.

(Reference 6)
Bradford, M. M. (1976) A rapid and sensitive method for the quantitation of microgram quantities of protein utilizing the principle of protein-dye binding. Anal. Biochem. 72, 248-254.

(Reference 7)
Chang, J. H., Tai, Y.-S., Bernal, A. J., Lavelle, D. T., Staskawicz, B. J. and Michelmore, R. W. (2002) Functional analyses of the Pto resistance gene family in tomato and the identification of a minor resistance determinant in a susceptible haplotype. Mol. Plant-Microbe Interact. 15, 281-291.

(Reference 8)
Chappell, J. (1995) The biochemistry and molecular biology of isoprenoid metabolism. Plant Physiol. 107, 1-6.

(Reference 9)
Choi, D., Ward, B. L. and Bostock, R. M. (1992) Differential induction and suppression of potato 3-hydroxy-3-methylglutaryl coenzyme A reductase genes in elicitor arachidonic acid. Plant Cell 4, 1333-1344.

(Reference 10)
Chomczynski, P. and Sacchi, N. (1987) Single-step method of RNA isolation by acid guanidium hiocyanate-phenol-chloroform extraction. Anal. Biochem. 162, 156-159.

(Reference 11)
Cruickshark, I. A. M. and Perrin, D. R. (1960) The isolation and particular characterization of monilicolin A, a polypeptide with phaseollin-inducing activity from *Monilinia fructicola*. Life Sci. 7, 449-458.

(Reference 12)
Darvill, A. G. and Albersheim, P. (1984) Phytoalexins and their elicitors—a defense against microbial infection in plants. Annu. Rev. Plant Physiol. 35, 243-275.
(Reference 13)
Dixon, R. A. and Harrison, M. J. (1990) Activation, structure and organization of genes involved in microbial defense in plants. Adv. Genet. 28, 165-234.
(Reference 14)
Doke, N. and Tomiyama, K. (1980) Effect of hypal wall components from *Phythophthora infestans* on protoplasts of potato tuber tissue. Physiol. Plant Pathol. 16, 169-176.
(Reference 15)
Doke, N. (1983) Involvement of superoxide anion generation in the hypersensitive response of potato tuber tissues to infection with an incompatible race of *Phythophthora infestans* and to the hyphal wall components. Physiol. Plant Pathol. 23, 345-357.
(Reference 16)
Facchini, P. J. and Chappel, J. (1992) Gene family for an elicitor-induced sesquiterpene cyclase in tobacco. Proc. Natl. Acad. Sci. USA 89, 11088-11092.
(Reference 17)
Feinberg, A. P. and Vogelstein, B. (1983) A technique for radiolabelling DNA reaction endoncrease fragments to high specific activity. Anal. Biochem. 136, 6-13.
(Reference 18)
Hashimoto, T., Yamada, T., Tada, A., Kawamata, S., Tanaka, Y., Sriprasertsak, P., Ichinose, Y, Kato, H., Izutsu, S., Shiraishi, T., Oku, H. and Ohtsuki, Y. (1992) Transient expression of a phenylalanine ammonia-lyase promoter. Plant Cell Reports, 11, 183-187.
(Reference 19)
Jefferson, R. A. (1987) Assaying chimeric genes in plants: The GUS gene fusion system. Plant Mol. Biol. Rep. 5, 387-405.
(Reference 20)
Katou, S., Senda, K., Yoshioka, H., Doke, N. and Kawakita, K. (1999) A 51 kDa protein kinase of potato activated with hyphal wall components from *Phytophthora infestans*. Plant Cell Physiol. 40, 825-831.
(Reference 21)
Kuc, J. and Rush, R. J. (1985) Phytoalexins. Arch. Biochem. Biophys. 236, 455-472.
(Reference 22)
Laemmli, U. K. (1970) Cleavage of structural proteins during the assembly of the head of bacteriophage T4. Nature 277, 680-685.
(Reference 23)
Leader, P., Tiemerier, D. and Enguist, L. (1977) EK2 derivatives of bacterio-phage lambda useful in the cloning of DNA from higher organisms. Science 196, 175-177.
(Reference 24)
Maniaitis, T., Fritsch, E, F. and Sambrock, J. (1982) Molecular Cloning: A Laboratory Manual. (Cold Spring Harbor, N.Y.: Cold Spring Laboratory)
(Reference 25)
McNeil, J. B. (1988) Functional Characterization of a Pyrimidine-Rich Element in the 5'-Noncoding Region of the Yeast Iso-1-Cytochrome c Gene. Mol. Cel. Biol. 8, 1045-1054.
(Reference 26)
Metlitsky, L. V., Ozeretskovskaya, O. L., Vasyukova, N. J., Davydova, M. A., Dorozhkin, N. A., Remneva, Z. J. and Ivanyuk, V. G. (1970) Potato resistance to *Phytophthora infestans* as related to leaf phytoalexin activity. Prikl. Biokhim. Mikrobiol. 5, 568-573.
(Reference 27)
Takashi Miyata (1984) Evolution of DNA, =Eucaryotic genes under dynamic evolution=, Basic molecular evolution theory, Ed. Motoo Kimura, Baifukan, Tokyo, pp. 56-90.
(Reference 28)
Moesta, P. and Grisebach, H. (1982) L-O-Aminooxy-3-phenylpropionic acid inhibits phytoalexin accumulation in soybean with concomitant loss of resistance against *Phythophthora megasperma* f. sp. glycinea. Physiol. Plant Pathol. 21, 65-70.
(Reference 29)
Murai, A., Sato, S., Osada, A., Katsui, N. and Masamune, T. (1982) Biosynthesis from solavetivone of the phytoalxin risitin in potato. J. Chem. Soc. Chem. Commun., 32
(Reference 30)
Murray. M. G. and Thompsin, W. F. (1980) Rapid isolation of high-molecular-weight plant DNA. Nucleic Acids. Res. 8, 4321-4325
(Reference 31)
Narita, J. O. and Gruissem, W. (1989) Tomato hydroxy-methylglutaryl-CoA reductase is required early in fruit development but not during ripening. Plant Cell 1, 181-190.
(Reference 32)
Oba, K., Kondo, K., Doke, N. and Uritani, I. (1985) Induction of 3-hydroxy-3-methylglutaryl CoA reductase in potato tubers after slicing, fungal infection or chemical treatment, and some properties of the enzyme. Plant Cell Physiol. 26, 873-880.
(Reference 33)
Ren, D., Yang, H. and Zhang, S. (2002) Cell death mediated by MAPK is associated with hydrogen peroxide production in *Arabidopsis*. J. Biol. Chem. 277, 559-565.
(Reference 34)
Rohwer, F., Fritzemeier, K. H., Scheel, D., and Hahlbrock, K. (1987) Biochemical reactions of different tissues of potato (*Solanum tuberosum*) to zoospores or elicitors from *Phytophthora infestans*. Planta 170, 556-561.
(Reference 35)
Romeis, T., Piedras, P., Zhang, S., Klessig, D. F., Hirt, H. and Jones, J. D. G. (1999) Rapid Avr9- and Cf-9-dependent activation of MAP kinases in tobacco cell cultures and leaves: convergence of resistance gene, elicitor, wound, and salicylate responses. Plant Cell 11, 237-287.
(Reference 36)
Reed, K. C. and Mann, D. A. (1985) Rapid transfer of DNA from agarose gel to nylon membranes. Nucleic Acids Res. 13, 7207-7221.
(Reference 37)
Sambrook, J., Fritsch, E. F. and Maniatis, T. (1989) Molecular Cloning: A Laboratory Manual, 2nd ed. Cold Spring Harbor, N.Y.: Cold Spring Harbor Laboratory.
(Reference 38)
Sanger, F., Nicklen, S. and Coulson, A. R. (1977) DNA sequencing chain-terminating inhibitors. Proc. Natl. Acad. Sci. USA 74, 5463-5467.
(Reference 39)
Starks, C. M., Back, K., Chappel, J. and Noel, J. P. (1997) Structure basis for cyclic terpene biosynthesis by tabacco 5-epi aristolochene synthase. Science 277, 1815-1820.
(Reference 40)
Stermer, B. A. and Bostock, R. M. (1987) Involvement of 3-hydroxy-3-methylglutaryl coenzyme A reductase in regulation of sesquiterpenoid phytoalexin synthesis in potato. Plant Physiol. 84, 404-408.
(Reference 41)
Thomas, C. M., Tang, S., Hammond-Kosack, K. E. and Jones, J. D. G. (2000) Comparison of the hypersensitive response induced by the tomato Cf-4 and Cf-9 genes in *Nicotiana* spp. Mol. Plant-Microbe Interact. 13, 465-469.
(Reference 42)
Threfall, D. R. and Whitehead, I. M. (1988) Co-ordinated inhibition of squalene synthetase and induction of enzymes of sesquiterpenoid phytoalexin biosynthesis in cultures of *Nicotiana tabacum*. Phytochemistry 27, 2567-2580.
(Reference 43)
Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Res. 22, 4673-4680.
(Reference 44)
Tomiyama, K. (1968) Further observation on the time requirement for hypersensitive cell death of potatoes infected by *Phytophthora infestans* and its reaction to metabolic activity. Phytopathology 58, 367-378.
(Reference 45)
Vance, C. P. and Sherwood, R. T. (1977) Lignified papilla formation as a mechanism for protection in reed canarygrass. Physiol. Plant Pathol. 10, 247-256.
(Reference 46)
VanEtten, H. D., Matthews, D. E. and Matthews, P. S. (1989) Phytoalexin detoxyfication: Importance for pathogenicity and practical implications. Annu. Rev. Phytopathol. 27, 143-164
(Reference 47)
Van Loon, L. C. and Van Kammen, A. (1970) Polyacrylamide disc electrophoresis of the soluble leaf proteins from *Nicotiana tabacum* var. 'Samsun' and 'Samsun NN'. Virology 40, 199-211.
(Reference 48)
Vögeli, U. and Chappel, J. (1988) Induction of sesquiterpene cyclase and suppression of squalene synthase activities in plant cell cultures treated with fungal elicitor. Plant Physiol. 88, 1291-1296.
(Reference 49)
Wilson, U. E. and Coffey, M. D. (1980) Cytological evaluation of general resistance to *Phytophthora infestans* in potato foliage. Ann. Bot. 45, 81-90.
(Reference 50)
Yang, K.-Y., Liu, Y. and Zhang, S. (2001) Activation of a mitogen-activated protein kinase pathway is involved in disease resistance in tobacco. Proc. Natl. Acad. Sci. USA 98, 741-746.
(Reference 51)
Yin, S., Mei, L., Newman, J., Back, K., and Chappell, J. (1997) Regulation of sesquiterpene cyclase gene expression: characterization of an elicitor- and pathogen-inducible promoter. Plant Physiol. 115, 437-451.
(Reference 52)
Yoshioka, H., Miyabe, M., Hayakawa, Y. and Doke, N. (1996) Expression of genes for phenylalanine ammonia-lyase and 3-hydroxy-3-methylglutaryl CoA reductase in aged potato tubers infected with *Phytophthora infestans*. Plant Cell Physiol. 37, 81-90.
(Reference 53)
Yoshioka, H., Yamada, N. and Doke, N. (1999) cDNA cloning of sesquiterpene cyclase and squalene synthase, and expression of the genes in potato tuber infected with *Phytophthora infestans*. Plant Cell Physiol. 40, 993-998.
(Reference 54)
Zook, M. N. and Kuc, J. A. (1991) Induction of sesquiterpene cyclase and supression of squalene synthetase activity in elicitor treated or fungal infected potato tuber tissue. Physiol. Mol. Plant Pathol. 39, 377-390.
(Reference 55)
Towbin, H., Staehelin, T. and Gordon, J. (1979) Electrophoretic transfer of proteins from polyacrylamide gels to nitrocellulose sheets: procedure and some applications. Proc. Natl. Acad. Sci. USA 76, 4350-4354.
(Reference 56)
Bhattacharyya, M. K., Paiva, N. L., Dixon, R. A., Korth, K. L. and Stermer, B. A. (1995) Features of the hmg1 subfamily of genes encoding HMG-CoA reductase in potato. Plant Mol. Biol. 28, 1-15.
(Reference 57)
Asai, T., Tena, G., Plotnikova, J., Willmann, M. R. Chiu, W.-L., Gomez-Gomez, L., Boller, T., Ausubel, F. M., and Sheen, J. (2002) MAP kinase signalling cascade in *Arabidopsis* innate immunity. Nature 415, 977-983.
(Reference 58)
Cardinale, F., Jonak, C., Ligterink, W., Niehausi, K., Boller, T. and Hirt, H. (2000) Differential activation of four specific MAPK pathways by distinct elicitors. J. Biol. Chem. 275, 36734-36740.
(Reference 59)
Baulcombe, D. C. (1999) Fast forward genetics based on virus-induced gene silencing. Curr. Opin. Plant Biol. 2: 109-113.
(Reference 60)
Gallagher, S. R. (1992) GUS Protocols: Using the GUS Gene as a Reporter of Gene Expression. 3. Quantitation of GUS activity by fluorometry. Gallagher, ed. San Diego, Calif., Academic Press. pp. 47-59.
(Reference 61)
Hellens, R. P., Edwards, A. E., Leyland, N. R., Bean, S., and Mullineaux, P. M. (2000) pGreen: A versatile and flexible binary Ti vector for *Agrobacterium*-mediated plant transformation. Plant Mol. Biol. 42: 819-832.
(Reference 62)
Kamoun, S., van West, P. V., Jung, A. J., Vleeshouwers, V. G. A. A., Groot, K. E. and Govers, F. (1997) A gene encoding a protein elicitor *Phytophthora infestans* is down-regulated during infection of tomato. Mol. Plant-Microbe Interact 10: 13-20.
(Reference 63)
Kamoun, S., West, P. V., Vleeshouwers, V. G. A. A., Groot, K. E. and Govers, F. (1998) Resistance of *Nicotiana benthamiana* to *Phytophthora infestans* is mediated by the recognition of the elicitor protein INF1. Plant Cell 10: 1413-1425.
(Reference 64)
Katou, S., Yamamoto, A., Yoshioka, H., Kawakita., K. and Doke, N. (2003) Functional analysis of potato mitogen-activated protein kinase kinase, StMPK1. J. Gen. Plant Pathol. 69: 161-168.
(Reference 65)
MAPK group (2002) Mitogen-activated protein kinase cascades in plants: a new nomenclature. Trends Plant Sci. 7: 301-308.
(Reference 66)
Mitchell, P. J. and Tjian, R. (1989) Transcriptional regulation in mammalian cells by sequence-specific DNA binding proteins. Science 245: 371-378.
(Reference 67)
Ratcliff, F., Martin-Hernandez, A. M. and Baulcomb, D. C. (2001) Tobacco rattle virus as a vector for analysis of gene function by silencing. Plant J. 25: 237-245.
(Reference 68)
Reed, K. C. and Mann, D. A. (1985) Rapid transfer of DNA from agarose gel to nylon membranes. Nucleic Acids Res. 13: 7207-7221.

(Reference 69)
Samuel, M. A. and Ellis, B., E. (2002) Double jeopardy: both overexpression and supression of a redox-activated plant mitogen-activated protein kinase render tobacco plants ozone sensitive. Plant Cell 14: 2059-2069.
(Reference 70)
Voinnet, O. (2001) RNA silencing as a plant immune system against viruses. Trends genet. 17: 449-459.
(Reference 71)
Yoshioka, H., Numata, N., Nakajima, K., Katou, S., Kawakita, K., Rowland, O., Jones, J. D. G. and Doke, N. (2003) *Nicotiana benthamiana* gp91$^{phox}$ homologs NbrbohA and NbrbohB participate in $H_2O_2$ accumulation and resistance to *Phytophthora infestans*. Plant Cell 15: 706-718.
(Reference 72)
Zhang, S., Du, H. and Klessig, D. F. (1998) Activation of the tobacco SIP kinase by both a cell wall-derived carbohydrate elicitor and purified proteinaceous elicitors from *Phytophthora* spp. Plant Cell 10: 435-449.
(Reference 73)
Zhang, S. and Liu, Y. (2001) Activation of salicylic acid-induced protein kinase, a mitogen-activated protein kinase, induces multiple defense responses in tobacco. Plant Cell 13: 1877-1889.
(Reference 74)
Zuo, J., Niu, Q.-W. and Chua, N.-H. (2000) An estrogen receptor-based transactivator XVE mediates highly inducible gene expression in transgenic plants. Plant J. 24: 265-273.

DISCLOSURE OF INVENTION

Attempts have been made to enhance disease resistance of plants by utilizing their resistance response. One of such efforts seeks to use pathogen responsive promoter to trigger production of resistance inducer specifically at the time of disease infliction. In this method, an effective protection is provided by resistance inducer specifically and promptly produced in response to disease infliction.

Several pathogen responsive promoters have been discovered in the past, most of which are inducible not only on the occasion of pathogen infection but also of wound or at sites under normal course of growth. Accordingly, if such a promoter is used to introduce a transgene, wich is involved in production of resistance inducer, into a plant, the resultant modified plant will have the transgene expressed not only at the time and location of infection, but harmfully elsewhere as well. The present invention is made, based on the above understanding, in order to provide a promoter that is responsive specifically to pathogen infection (pathogen responsive promoter) and method for producing pathogen resistant plants utilizing the same.

In view of the objectives described above, the present inventor first sought to obtain a promoter that is responsive specifically to the notorious late blight pathogen, *Phytophthora infestans*, a devastating disease of potato plants. Potato vetispiradiene (PVS) is a one of those genes involved in production of phytoalexin. The inventor first investigated the expression trend of each of the PVS members (PVS1 to PVS4) in leaf tissue which is a primary infection site of *P. infeatans*, and found that only PVS3 was significantly induced after inoculation with either compatible and incompatible race. Thus, it was demonstrated that the promoter for PVS3 is responsive also to infection with compatible race.

Genomic library of potato was then constructed to sequence PVS3. After several rounds of screening, genomic DNA sequence of PVS3 was successfully determined, and PVS3 promoter region and its function predicted, thus confirming the responsiveness to *P. infeatans*. In order to further explore the function of the deduced promoter region, potato transformant was constructed which had the deduced promoter region inserted upstream of GUS gene, and a panel of study conducted using the transformant. It was found that leaf resection (wound) did not evoke GUS staining, whereas inoculation with compatible race of *P. infeatans* did. In conclusion, the promoter region was determined to be *Phytophthora*-specific, i.e. to have pathogen-specific responsiveness.

As described above, the present inventor has successfully obtained a promoter that is responsive specifically to pathogen (pathogen-responsive promoter). The present promoter will allow creation of a plant that expresses a gene of interest only when infected with pathogen. Specifically, in such a transformant having the present promoter along with a transgene, the introduced promoter will induced specifically to express the transgene. If the transgene is the one that activates protective response, the resultant plant will have its protective response activated specifically in response to pathogen infection. Accordingly, the plant will be highly resistant to pathogen infection.

Gene transcription, in general, begins with binding of a protein called transactivator to a particular sequence consisting of several to ten and several bases called cis-sequence within promoter regions (Reference 66). Identification of cis-sequences is therefore a first step of elucidation of transcription mechanism. Based on such an understanding, the present inventor designed a panel of identified PVS3 promoter sequences with varied portions deleted, combined them with GUS gene to produce chimeric PVS3:GUS, and temporarily introduced them into leaf tissue to examine PVS3 promoter activity. As a result, it was successfully found a region consisting of 50 bp (SEQ ID NO: 23), and identified it as a region essential for PVS3 promoter activity. Besides, any known regulation motif was not found in the region at this time point.

Although the pathogen-responsive promoter (PVS3 promoter) which the present inventor successfully identified had been derived from potato plant, the promoter may be applicable to plants other than potatoes. First, while PVS3 is an enzyme that catalyzes synthesis of phytoalexin in potato plants, phytoalexin of eggplant, Solanaceae, is similarly terpene compound, and has a common synthesis pathway. In addition, the present gene is SIPK and WIPK dependent inducible, as will be described later in detail. It is generally known that these two enzymes are involved in protective response of a number of plants, including Solanaceae. In view of these similarities, the present promoter (PVS3 promoter) is expected to be applicable as pathogen-responsive promoter not only to Solanacease but also Brassicaceae (See Reference 57), Leguminosae (See Reference 58) and other wide variety of plants having reported relevance of SIPK and WIPK orthologs.

The present invention is based on the above study and findings, and provides:

[1] A pathogen-responsive promoter, comprising:

(a) a DNA comprising nucleotide sequence shown in SEQ ID NO:1;

(b) a DNA comprising nucleotide sequence shown in SEQ ID NO:1 with replacement, deletion, insertion or addition of one or more nucleotide(s) and functioning as pathogen-responsive promoter in plant cell; or (c) a DNA hybridizing to DNA of (a) or (b) under a stringent condition and functioning as pathogen-responsive promoter in plant cell.

[2] A pathogen-responsive promoter, comprising:
(A) a DNA comprising nucleotide sequence shown in SEQ ID NO:2;
(B) a DNA comprising nucleotide sequence shown in SEQ ID NO:2 with replacement, deletion, insertion or addition of one or more nucleotide(s) and functioning as pathogen-responsive promoter in plant cell; or
(C) a DNA hybridizing to the DNA of (A) or (B) under a stringent condition and functioning as pathogen-responsive promoter in plant cell.

[3] A pathogen-responsive promoter, comprising:
(1) a DNA comprising a continuous portion of nucleotide sequence shown in SEQ ID NO:1, and functioning as pathogen-responsive promoter in plant cell;
(2) a DNA according to (1) with replacement, deletion, insertion or addition of one or more nucleotide(s) and functioning as pathogen-responsive promoter in plant cells; or
(3) a DNA hybridizing to the DNA of (1) or (2) under a stringent condition and functioning as pathogen-responsive promoter in plant cell.

[4] A pathogen-responsive promoter, comprising:
(i) a DNA comprising nucleotide sequence shown in SEQ ID NO:22;
(ii) a DNA comprising nucleotide sequence shown in SEQ ID NO:22 with replacement, deletion, insertion or addition of one or more nucleotide(s) and functioning as pathogen-responsive promoter in plant cell; or
(iii) a DNA hybridizing to the DNA of (i) or (ii) under a stringent condition and functioning as pathogen-responsive promoter in plant cell.

[5] A pathogen-responsive promoter functioning as pathogen-responsive promoter in plant cell and comprising:
(I) a DNA comprising nucleotide sequence shown in SEQ ID NO:23;
(ii) a DNA comprising nucleotide sequence shown in SEQ ID NO:23 with replacement, deletion, insertion or addition of one or more nucleotide(s); or
(iii) a DNA hybridizing to the DNA of (i) or (ii) under a stringent condition.

[6] The pathogen-responsive promoter according to any one of [1] to [5], which is characterized by being responsive specifically to *Phytophthora* infection.

[7] A DNA comprising nucleotide sequence shown in SEQ ID NO:23.

[8] A DNA comprising 10 or more continuous nucleotides of nucleotide sequence shown in SEQ ID NO:23 and having pathogen-responsive promoter activity.

[9] A vector comprising the pathogen-responsive promoter according to any one of [1] to [6].

[10] A vector comprising the DNA according to [7] or [8].

[11] A DNA construct comprising the promoter according to any one of [1] to [6] and a gene linked under the control of the promoter and expressed in plant to activate protective response of the plant.

[12] A DNA construct comprising the DNA according to [7] or [8], a DNA cooperatively constituting with the DNA a pathogen-responsive promoter, and a gene linked under the control of the constituted pathogen-responsive promoter and expressed in plant to activate protective response of the plant.

[13] The DNA construct according to [11] or [12], wherein the expression product of the gene has the function to activate communication pathway controlling the protective response of the plant.

[14] The DNA construct according to [11] or [12], wherein the expression product of the gene has the function to activate SIPK or WIPK.

[15] The DNA construct according to [11] or [12], wherein the gene encodes a constantly active form of MEK.

[16] A transformant derived from host plant transformed by the DNA construct according to any one of [11] to [15].

[17] The transformant according to [16], wherein the host plant belongs to Solanaceae.

[18] The transformant according to [16], wherein the host plant belongs to *Solanum tuberosum*.

[19] A method for producing a transgenic plant, comprising the step of:
transforming a host plant with the DNA construct according to any one of [11] to [15].

[20] A method for affording pathogen resistance to a host plant, comprising the step of:
transforming the host plant with the DNA construct according to any one of [11] to [15].

[21] A plant into which a pathogen-responsive promoter according to any one of [1] to [6] has been exogenously introduced.

[22] A plant into which the DNA according to [7] or [8] has been exogenously introduced.

"Pathogen-responsive promoter" in the present invention means a promoter that is responsive to (induced by) pathogen infection. "Promoter" as used herein refers to a functional region under whose control the initiation of transcription of a gene is regulated.

"Exogenously introduced" as used herein means introduction from outside. Accordingly, "exogenously introduced promoter" means a promoter that is introduced from outside of the host cell. For example, even if the host cell natively possesses a promoter identical to that promoter which is introduced, only the latter is referred to as "exogenously introduced promoter" for discrimination purpose, regardless of whether they are identical in construction.

The phrase "comprising DNA" in the present invention is used to encompass "consisting of DNA". For example, "a promoter comprising a given DNA" is considered to include "a promoter consisting of a given DNA".

In the present specification, the abbreviations shall have the meanings as follows; ATP: adenosine 5'-triphosphate, BPB: bromophenol blue, BSA: bovine serum albumin, CBB: coomassie brilliant blue, CTP: cytidine 5'-triphosphate, DEPC: diethylpyrocarbonate, DTT: dithiothreitol, EDTA: ethylenediamine-N,N,N',N'-tetraacetic acid, EGTA: ethyleneglycol bis(β-amonoethylether) ethylenediamine-tetraacetic acid, FPP: farnesyl diphosphate, GAP: glyceraldehyde 3-phosphate, GTP: guanosine 5'-triphosphate, HMG-CoA: 3-hydroxy-3-methylglutaryl coenzyme A, HMGR: 3-hydroxy-3-methylglutaryl coenzyme A reductase, HWC: hyphal wall components, Ig: immunoglobulin, IPP: isopentenyl diphosphate, IPTG: isopropyl-1-thio-β-D-thiogalactoside, kD: kilodalton, MOPS: 3-(N-morpholino) propanesulfonic acid, PAGE: polyacrylamide gel electrophoresis, PBS: phosphate-buffered saline, PCR: polymerase chain reaction, PMSF: phenylmethylsulfonyl fluoride, PR: pathogenesis related, SDS: sodium dodesyl sulfate, SHAM: salycylhydroxamic acid, SSPE: sodium chloride-sodium phosphate, EDTA, TBE: trisborate, EDTA, TBS: tris-buffered saline, TE: tris-EDTA, Tris: 2-N-tris (hydroxymethyl) aminomethane, TTP: thiamine 5'-triphosphate, X-gal: 5-bromo-4-chloro-3-indolyl-β-D-galactoside.

Unless otherwise specified, the genetic engineering operations in the following description can be performed with reference to Molecular Cloning (Third Edition, Cold Spring Harbor Laboratory Press, New York) or Current protocols in molecular biology (edited by Frederick M. Ausubel et al., 1987).

The present invention provides a promoter that is induced by pathogen infection. Gene transfer using the present promoter allows creation of transgenic plant wherein a desired gene is expressed specifically on the occasion of pathogen infection. Accordingly, by transferring any gene involved in protective response, pathogen-resistant plant can be created which evokes a prompt protective response to pathogen infection.

BRIEF DESCRIPTION OF DRAWINGS

FIG. 6 shows deduced nucleotide sequence and deduced amino acid sequence of PVS3 genomic clone, with a portion of deduced promoter and coding regions shown. Amino acid sequences are indicated below the nucleotide sequences by which they are encoded. Non-coding regions are indicated by lower case letters. Stop codons are marked with asterisks. (nucleotide is disclosed as nucleotides 1-3420 of SEQ ID NO: 40; protein disclosed as residues 1-197 of SEQ ID NO: 41)

FIG. 7 shows deduced nucleotide sequence and deduced amino acid sequence of PVS3 genomic clone, with a portion of coding region and untranslated region shown. Amino acid sequences are indicated below the nucleotide sequences by which they are encoded. Non-coding regions are indicated by lower case letters. Stop codons are marked with asterisks. (nucleotide is disclosed as nucleotides 3421-5236 of SEQ ID NO: 40; protein disclosed as residues 198-551 of SEQ ID NO: 41)

FIG. 10 Luciferase activity by the treatment with hyphal wall components (HWC) elicitor or water in electroporated potato protoplasts. (A) Construct of Luc gene for transient assay using PVS3 promoter region. (SEQ ID NOS 42 & 43 disclosed respectively in order of appearance) In (B), 35S represents luciferase activity when CaMV 35S promoter region was used, HWC represents that activity when the deduced promoter region was used and HWC treatment was performed, and Water represents that activity when water treatment was performed instead of HWC treatment.

FIG. 13 Expression pattern of PVS3 promoter in response to inoculation with $P.$ infestans. Transgenic potato leaves (MayQueen) or potato leaves (Rishiri) were inoculated with race 0 (compatible for MayQueen and incompatible for Rishiri). GUS activity was detected by GUS staining solution 6, 12, 24, and 48 hr after inoculation. Transgenic potato leaves were observed under the microscope.

FIG. 16 Expression pattern of GUS driven by PVS3 promoter in response to $H_2O_2$. $H_2O_2$ (5 mM) was injected into transgenic potato leaves. GUS activity was detected using GUS staining solution 6, 12, 24, and 48 hr after injection.

FIG. 17 Expression pattern of GUS driven by PVS3 promoter in response to glucose/glucose-oxydase. Glucose (5 mM) and glucoseoxydase (0.5 U/ml) were injected into transgenic potato leaves. GUS activity was detected using GUS staining solution 6, 12, 24, and 48 hr after injection.

FIG. 18 Expression pattern of GUS driven by PVS3 promoter in response to salicylic acid (SA). SA (0.5 U/ml) was injected into transgenic potato leaves. GUS activity was detected using GUS staining solution 6, 12, 24, and 48 hr after injection.

FIG. 21 shows the sequence of coding region of MEK gene (MEK) (SEQ ID NO: 5) of potato plant and deduced amino acid sequence (SEQ ID NO: 6) encoded by the MEK gene.

FIG. 22 shows the sequence of coding region of constantly active form of MEK gene (SEQ ID NO: 7) (StMEK$^{DD}$) and deduced amino acid sequence (SEQ ID NO: 8) encoded by the MEK gene.

FIG. 23 shows the positions of primer sequences used in Examples. Numerals which are accompanied by arrows pointing at each primer position represent sequence identification numbers (For example, P9 represents a primer having the sequence of SEQ ID NO:9). In Example 2, P9, P10, P11, P14, P15, P16, P17, and P18 were used. On the other hand, in Example 4, P11, P12, P13, P14, P15, P16, P19, and P20 were used.

FIG. 24 shows primer sequences used in construction of deletion clones of pPVS3-1 through pPVS3-10. F denotes a forward primer, R denotes a reverse primer, and underlines indicate positions of restriction enzymes.

FIG. 29 shows the nucleotide sequence and deletion position from pPVS3-1 to pPVS3-10 of PVS3 promoter. Sequence between −1,337 and −1,287, where cis-sequence is expected to lie, is shown by bold letters, and deduced TATA box and CAAT box are enclosed in square. (nucleotide is disclosed as nucleotides 1-2700 of SEQ ID NO: 40; protein disclosed as residues 1-17 of SEQ ID NO: 41)

FIG. 32 shows the effect of WIPK and SIPK on PVS3 promoter activity and TEAS gene expression induced by StMEK1$^{DD}$ expression. Silencing of either WIPK or SIPK significantly suppressed the PVS3 promoter activity induced by StMEK1$^{DD}$ (A). Further, Northern analysis of the total RNA extracted demonstrated that the expression of sesquiterpene cyclase gene of Nicotiana benthamiana was suppressed only at the area where WIPK and SIPK were silenced (B).

BEST MODE FOR CARRYING OUT THE INVENTION

Promoter

Figure 1:
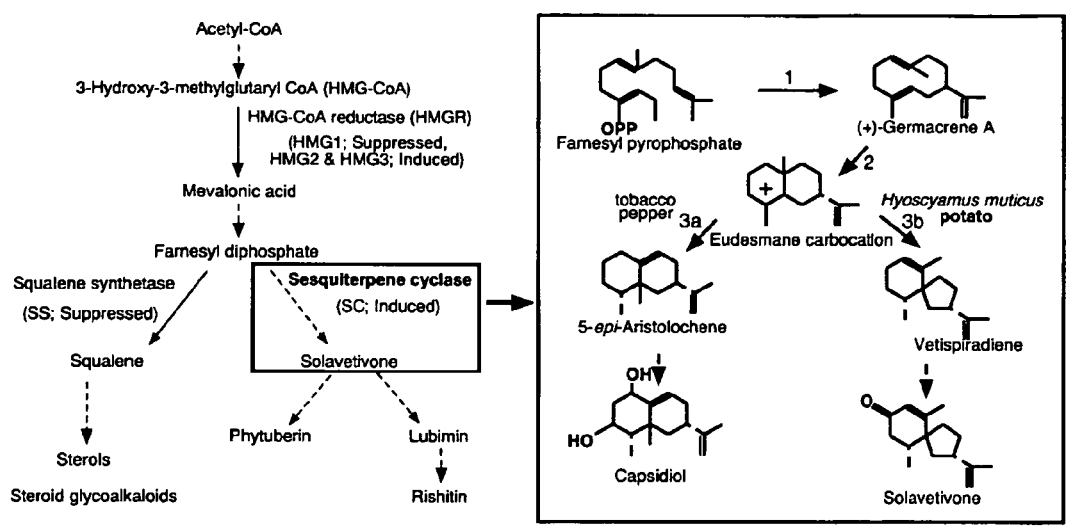
FIG. 1 A scheme of stimulus-responsive isoprenoid biosynthesis in potato tuber. Wound-induced sterol and steroid glycoalkaloid syntheses are suppressed in favor of sesquiterpenoid phytoalexin synthesis during expression of the hypersensitive response.

A first aspect of the present invention relates to a pathogen-responsive promoter, an embodiment of which comprises DNA including the nucleotide sequence shown in SEQ ID NO:1. The DNA has been identified as promoter of potato PVS3 gene, and has been recognized as being responsive specifically to Phytophthora infestans, a type of virulent pathogen. As a result of further examination, it was found that deletion of upstream region resulting in a fragment consisting of as few as about 1,300 bp (SEQ ID NO:22) retained the intended promoter activity. In view of these findings, a preferred embodiment of the present invention is a pathogen-specific promoter comprising DNA having the nucleotide sequence shown in SEQ ID NO: 22. On the other hand, deletion of a region of 50 bp (SEQ ID NO: 23) upstream the DNA sequence (SEQ ID NO:22) resulted in a dramatic decrease of the promoter activity. Thus, the deleted 50 bp (SEQ ID NO:23) is expected to comprise an extremely essential region for the promoter activity, i.e. cis-sequence of PVS3 gene promoter. Accordingly, the region (hereinafter referred also to as "first DNA sequence") is highly useful for construction of a pathogen-responsive promoter, and the use of the region allows flexible design and construction of DNA construct incorporating the pathogen-responsive promoter (for example, recombinant vector for use in imparting pathogen resistance to plant. See the section of "DNA construct" below.). Thus, another embodiment of the present invention provides DNA sequence useful for construction of a pathogen-responsive promoter. Since cis-sequences in general consist of ten and several nucleotides, a portion of the first DNA sequence is predicted to be a cis-sequence. This implies that DNA consisting only of a portion of first DNA sequence may be useful for construction of a pathogen-responsive promoter as long as it contains a cis-sequence. An exemplary DNA encompassed in such a DNA comprises continuous 10 or more nucleotides, preferably continuous 15 or more nucleotides, and more preferably continuous 20 or more nucleotides of the first DNA sequence.

When the first DNA sequence (or a continuous portion thereof, or those DNA (Modified DNA) obtained by modifying the first DNA sequence or a continuous portion thereof as specified below such that its function will be retained) is used, a pathogen-responsive promoter can be constructed by incorporating any other DNA sequences into the first DNA sequence. The other DNA sequences herein referred to are those which cooperate with the first DNA sequence (or its Modified sequence) to construct a pathogen-responsive promoter. Specifically, the sequence shown in SEQ ID NO:24, for example, may be used as the other DNA sequence. The DNA sequence is the DNA sequence of that region which is flanked by the first DNA sequence and the coding region of PVS3 gene (See FIG. 29). Since this flanked region includes CAAT box and TATA box, and a native PVS3 promoter region is constructed by using this flanked region, the pathogen-responsive promoter created in this embodiment will have a high promoter activity. In addition to this example, any other DNA sequence including CAAT box and TATA box is expected to provide a favorable promoter function through cooperation with these sequences involved in transcription initiation and transcription regulation. The other DNA sequence may be linked directly, or via any other sequence, with the first DNA sequence.

The term "pathogen" as used herein refers to any fungus that infects to and harms plants, including Phytophthora and other virulent filamentous fungi and virulent bacteria. "Phytophthora" as used herein refers to any fungi that belongs to the genera of Phytophthora, and is classified according to infected subject. Exemplary Phtophthora are: potato Phytophthora (Phytophthora infestans), tobacco Phytophthora (Phytophthora nicotianae), soybean pedicle Phytophthora (Phytophthora megasperma var. sojae), and apple Phytophthora (Phytophthora cactorum and Phytophthora cambivora). Exemplary virulent filamentous fungi are: potato Sclerotium (Sclerotinia sclerotiorum), Pyricularia oryzae (Magnaporthe grisea), and soybean rust (Phakopsora pachyrhizi). Exemplary virulent bacterium is fungi of bacterial disease of tomato (Ralstonia solanacearum, bacterium).

The promoter according to the present invention (comprising DNA useful for construction of a pathogen-responsive promoter. Unless otherwise indicated, this definition holds hereinafter) preferably is responsive specifically to pathogen infection. The term "specifically" means having a high specificity. Accordingly, the promoter according to the present invention preferably has a high specificity to pathogen infection, i.e. is responsive to pathogen infection as well as substantially lacks responsiveness to those disease other than pathogen infection.

(Method for Obtaining the Promoter)

The promoter according to the present invention can be prepared from potato plant such as Solanum tuberosum L. by extracting its genomic DNA using any standard technique, and then performing PCR or other gene amplification reaction using primers specific to the promoter of the present invention. Specifically, the promoter according to the present invention can be prepared in accordance with the following procedures. First, harvested and frozen potato leaves or tubers are ground in a mortar. Subsequently, an appropriate amount of extraction buffer (Tris-HCl buffer containing SDS, for example) is added to obtain extraction, followed by extraction and purification of genomic DNA by phenol extraction, ethanol precipitation or other means. The genomic DNA thus obtained is used as a template to perform PCR using primers specific to the promoter shown in SEQ ID NO:1 to obtain DNA (promoter) of interest as amplification product. Primers used may be, for example, a pair of primers having the following sequences:

Sense primer: TTGTCTGCTGCTGCTTGTGG (SEQ ID NO: 15)

Antisense primer: TCTCCATGAGTCCTTACATG (SEQ ID NO: 16)

Primers are designed to amplify specific DNA of interest. A set of primers for specifically amplifying DNA shown in SEQ ID NO:22 are:

Sense primer: CGGAATTCGTCCGCCCTTACTATTC-CCATC (SEQ ID NO:26)

Antisense primer: CCATCGATTCCTCTTCATTGT-TAAAGGGGA (SEQ ID NO:35)

Method for preparing the promoter according to the present invention is not limited to that described above. For example, commercially available potato genomic library (for example, genomic library of potato race Desiree (Clontech)) may be used for preparation. In order to isolate the promoter of interest from such a genomic library, plaque hybridization or colony hybridization, among others, may be used depending on the type of library (See Molecular Cloning, Third Edition, Cold Spring Harbor Laboratory Press, New York, for example). For example, in the case of library constructed using phage, plaque hybridization may be used. Selection of clone having the promoter region of interest may be achieved by using any probe having a sequence specific for the promoter of the present invention.

Once the clone of interest has been selected, the DNA contained in the clone may be used as template of PCR or other reaction using primers specific to the sequence shown in SEQ ID NO:1 to obtain the promoter of the present invention as amplification product.

The DNA contained in the clone obtained can be subcloned into any appropriate vector for further use. This allows construction of recombinant vector useful for transformation (See the second aspect of the present invention that will be described later) or construction of plasmid that is useful for sequencing of nucleotides.

Method for preparing the promoter according to the present invention is not limited to those described above, and any commercially available DNA synthesizer, for example, may be used for synthesis of the present promoter.

(Modified Promoter)

Since the sequence shown in SEQ ID NO:1 is about 2,600 bp long and relatively huge as promoter region, those nucleotides which are effectively involved in promoter activity is expected to be only a portion thereof. In view of this, even a partial continuous region of the sequence shown in SEQ ID NO:1 may constitute a pathogen-responsive promoter according to the present invention as long as it proves to function as a pathogen-responsive promoter. In addition, functional region of a promoter is usually located immediately before its structural gene. Therefore, in the case of sequence of PVS3 gene shown in FIGS. 6 and 7, the region consisting of −2,000 through −1 (SEQ ID NO:2), preferably the region consisting of −1,500 through −1 (SEQ ID NO:3), more preferably the region consisting of −1,000 through −1 (SEQ ID NO:4) may be promising candidates for functional region. As a matter of fact, as indicated in examples below, it has been demonstrated that the region which is about 1,300 bp in length immediately before the structural gene (SEQ ID NO:22) has a promoter activity. On the other hand, deletion of a region of 50 bp (SEQ ID NO:23) further upstream the approximately 1,300 bp region resulted in a dramatic decrease of promoter activity. Thus, it was found that at least one of functional regions of PVS3 promoter lies within this region of 50 bp. Based on this fact, the promoter according to the present invention preferably includes the sequence shown in SEQ ID NO:23. One example of such a promoter is DNA shown in SEQ ID NO:22 (−1,337 through −1 of PVS3 gene).

Meanwhile, DNA may occasionally retain its function even when partially modified. In view of this, any DNA having a partially modified nucleotide sequence (also referred to as "modified DNA") compared to the above described DNA (namely, DNA shown in SEQ ID NO:1, or DNA (for example, DNA shown in SEQ ID NO:22) including the above described functional region (SEQ ID NO:23)) constituting the promoter according to the present invention can constitute a pathogen-responsive promoter as long as it retains the function as pathogen-responsive promoter. In other words, partial modification of the sequence is permissible as long as its pathogen-responsive promoter function is retained. The term "partial modification" as used herein refers typically to replacement, deletion, insertion, or addition of one or more nucleotide(s) in the sequence shown in SEQ ID NO:1 (any one of SEQ ID Nos:2 through 4) or in the sequence shown in SEQ ID NO:22. Such modification can be made on a plurality of locations. The term "plurality" as used herein varies, depending on the site or type of modification made, for example between 2 and 100, preferably 2 and 50, more preferably 2 and 10. Such modified DNA can be achieved by inserting mutation by, for example, treatment by restriction enzyme, treatment by exonuclease, DNA ligase or other enzyme, site-directed mutagenesis (Molecular Cloning, Third Edition, Chapter 13, Cold Spring Harbor Laboratory Press, New York), and random mutagenesis (Molecular Cloning, Third Edition, Chapter 13, Cold Spring Harbor Laboratory Press, New York).

Any DNA which hybridizes under a stringent condition with DNA comprising the sequence of SEQ ID NO:1 (or any one of SEQ ID Nos:2 through 4), or with DNA comprising the sequence of SEQ ID NO:22 and also functions as pathogen-responsive promoter in plant cell can be used as DNA constituting the promoter according to the present invention. Further, any DNA which hybridizes under a stringent condition with DNA comprising the sequence with the above partial modification on the sequence of SEQ ID NO:1 (or the sequence with the above partial modification on the sequence of SEQ ID Nos:2 through 4), or with DNA comprising the sequence with the above partial modification on the SEQ ID NO: 22 and also functions as pathogen-responsive promoter in plant cell can be used. The term "stringent condition" as used herein refers to those conditions under which a so-called specific hybrid is formed, and non-specific hybrid not formed. Stringent conditions vary depending on the length of sequence and the type of constituent nucleotides. Exemplary condition is incubation in hybridization solution (50% formaldehyde, 10×SSC (0.15 M NaCl, 15 mM sodium citrate, pH 7.0), 5×Denhardt solution, 1% SDS, 10% dextran solution, 10 μg/ml of denatured salmon sperm DNA, 50 mM phosphate buffer (pH 7.5)) at 42° C., followed by washes in 0.1×SSC, 0.1% SDS at 68° C. An example of more preferable stringent conditions is such a condition using a solution of 50% formaldehyde, 5×SSC (0.15 M NaCl, 15 mM sodium citrate, pH 7.0), 1×Denhardt solution, 1% SDS, 10% dextran sulfate buffer, and 10 μg/ml of denatured salmon sperm DNA in 50 mM phosphate buffer (pH 7.5) as hybridization solution.

(DNA Construct)

By linking, under the control of the promoter of the present invention, any gene (transgene) which activates, upon expression, protective responsive of plant, DNA construct can be produced which is useful in imparting pathogen resistance to the plant. When producing a DNA construct for use in transformation, it is preferred that the promoter of the present invention and transgene of interest are incorporated into any appropriate vector (plasmid, bacteriophage, or virus, for example).

(Transgene)

Any transgene is used which activates protective response of the plant into which it has been introduced. For example, any gene that activates a communication pathway controlling protective response of the plant may be used as transgene. Exemplary genes of this type are MEK genes which activate SIPK (salicylic acid-induced protein kinase), a mitogen-activated protein (MAP) kinase, or WIPK (Wound-Induced Protein Kinase). An example of MEK genes is shown in FIG. 21 as the sequence of coding region of potato MEK gene (StMEK) (SEQ ID NO:5) and the amino acid sequence (SEQ ID NO: 6) encoded thereby.

It is especially preferable to use as transgene any gene encoding a constitutive active form of protein, because such a gene can produce an originally active form of protein that activates and effects protective response of the transformant in a prompt and assured manner. Genes encoding constitutive active form of proteins can be produced by partially modifying the nucleotide sequence of any gene encoding a wild type of protein such that the encoded amino acid sequence is partially mutated. For potato plant, a constitutive active form of protein MEK (StMEK$^{DD}$) having a modified MEK has been produced, and the corresponding gene encoding the StMEK$^{DD}$ may be used in the present invention as transgene. The nucleotide sequence of the coding region of StMEK$^{DD}$ gene (SEQ ID NO:7) and the encoded amino acid sequence (SEQ ID NO:8) are shown in FIG. 22.

The type of "protective response" in the above description is not limited in any way, and encompasses production of phytoalexin, expression of PR (Pathogenesis-Related) protein, production of reactive oxygen species, formation of papilla, and lignification.

(Vector)

Vectors for use in production of the above-described DNA construct are not limited, as long as they can introduce the promoter of the present invention and a transgene to be placed under control thereof into a target cell (host cell) and allow expression of the transgene within the target cell. Depending on the purpose, plasmid vector and λ phage vector, for example, are used. In constructing a vector for use in transformation using *Agrobacterium* as will be described later, Ti plasmid binary vector, Ti plasmid vector having T-DNA boundary sequence, for example, can be used. When the vector is used for any transformation without the need of *Agrobacterium* (for example, electroporation, and particle gun), a variety of pUC series plasmid vectors, a variety of λ phage vectors (ZAPII and others) may be used to construct a recombinant vector. A number of vectors are commercially available, an appropriate one among which may be selected, depending on the purpose, for use in the present invention.

A vector that contains the promoter of the present invention may first be constructed, and then a transgene be linked thereto. Namely, a universal vector that permits insertion of a desired transgene may first be constructed, and then be used for production of a recombinant vector for performing transformation.

The vector for performing transformation typically contains a transgene and any appropriate terminator in addition to the promoter of the present invention. The promoter, transgene and terminator are positioned in this order toward downstream such that transcription of the transgene by the promoter can be appropriately effected. The recombinant vector may further contain a selectable marker, a sequence having an enhancer function, and a sequence encoding any signal peptide.

(Terminator)

Terminator is a sequence that is recognized as signal to terminate synthesis of mRNA. Any terminator that functions correctly in plant cell is used. For example, Nos terminator is useful.

(Selectable Marker)

Selectable marker is used for recognizing or selecting those cell, tissue or callus that has underwent transformation. A variety of selectable marker are known, including, for example, npt gene (Herrera Estrella, EMBO J. 2(1983), 987-995) and nptll gene (Messing & Vierra. Gene 1 9:259-268 (1982)) for imparting resistance against kanamycin, hph gene (Blochinger & Diggl mann, Mol Cell Bio 4:2929-2931) for imparting resistance against hygromycin, dhfr gene (Bourouis et al., EMBO J. 2(7)) for imparting resistance against methotrexate, β-glucronidase (GUS) gene, GFP gene (Gerdes, FEBS Lett. 389 (1996), 44-47), luciferase (Giacomin, P1. Sci. 116 (1996), 59 to 72; Scikantha, J. Bact. 178 (1996), 121) and may be selected for use depending on the vector's host system and application.

The promoter and transgene may be inserted to the vectors by any standard technique, such as by using restriction enzyme DNA ligase (See Molecular Cloning, Third Edition, 1.84, Cold Spring Harbor Laboratory Press, New York, for example).

(Method for Transformation)

The DNA construct or recombinant vector according to the present invention can be used for transformation of plants. Transformation (gene transfer) can be achieved, for example, by means of *Agrobacterium tumefaciens* (*Agrobacterium* Method), polyethylene glycol (polyethylene glycol Method), and particle gun wherein metal particles with gene of interest bound thereto are shot into plant tissue (cell). Details of each of these methods are described in a variety of references and publications. For *Agrobacterium* Method, for example, see Proc. Natl. Acad. Sci. USA 86 (1989), 8467-8471 and Plant Mol. Biol. 20 (1992), 963-976.

Transformation of potato plant can be achieved by the method according to Jefferson (1987) (See Reference 19).

In the transformant obtained through the DNA construct containing the promoter of the present invention and any transgene, the introduced promoter can be induced in response to pathogen infection, and the transgene which is under the control thereof expressed. Accordingly, any transgene that is effective in providing protection against pathogen infection can be used to obtain a plant (transformant) which is resistant to pathogen. A plant cell obtained through the transformation can be used to regenerate a transgenic plant. Such regeneration can be achieved by any standard technique, depending on the type of plant.

(Target Plant)

The plant to be transformed by means of the DNA construct or recombinant vector according to the present invention (target plant) is not limited but may be any dicotyledon or monocotyledon. Dicotyledon includes, for example, Solanaceae (*Solanum tuberosum*, tobaccos, tomatoes), Osmandaceae (*Prunus mume, Prunus persica, Mulus pumila*), Leguminosae (for example, *Glycine max, Pisum sativum*), Brassicaceae (for example, *Raphanus sativus*), Pedaliaceae. Monocotyledon includes, for example, Gramineae (*Oryza sativa, Triticum, cereale, Hordeum vulgare, Coix lacrymajoli*, maize, Saccharum, for example), Liliaceae (*Allium fistulosum, Allium sativum*, for example).

The present invention will be described in greater detail with reference to the following Examples.

EXAMPLES

Biological materials, reagents, experimental procedures and other details employed in the Examples 1 through 8 below are as follows.

1. Tested Plants

Cultivar Danshaku (*Solanum tuberosum* L.) having no true resistance gene R1 and cultivar Rishiri (interspecies hybrid between *Solanum tuberosum* L. and wild species *S. demissum* L.) having a true resistance gene R1 were used as potato plant. Tubers of Danshaku cultured at the farm of Department of Agricultural Science, Nagoya University, and harvested in July, and tubers of the Rishiri cultured at the field of Hokkaido National Agricultural Experimental Station, the Ministry of Agriculture, Forestry and Fisheries and harvested in October were kept at 4° C. before testing. For producing a transgenic plant, MayQueen having no true resistance gene was used.

2. Tested Pathogen

Potato *Phytophthora*, [*Phytophthora infestans* (Mont.) de Bary] race 0 and races 1, 2, 3, and 4 stored in the Laboratory of Bioresource functions, Graduate School of Bioagricultural Sciences, Nagoya University were used. In addition, as a pathogen for use in preparing potato *Phytophthora* body wall component (HWC) elicitor, potato *Phytophthora* [*Phytophthora infestans* (Mont.) de Bary] races, 1, 2, 3 and 4 stored in the same laboratory was used.

3. Preparation of Pathogen Inoculum

Planospore suspension of potato *Phytophthora* was prepared as follows. Tubers of potato (*Solanum tuberosum* L.) that had been stored at 4° C. was washed extensively with tap water, and immersed in 1% sodium hypochlorite for about 10 minutes. The tubers were then sliced (into the thickness of about 10 mm), washed with water, had the planospore suspension that had been prepared in about $10^4$ zoospore/ml applied thereon for inoculation, and cultured for six days at 20° C. under a humidified darkness. Pathogens that grew out on the slice surface was stripped off with forceps, and suspended in cold distilled water (4° C.). The spore suspension was filtered through metal mesh (356 gauge) to remove fungal threads, and suctioned filtered using a paper filter (ADVANTEC No. 5B). The zoosporangia collected on paper filter was washed with cold distilled water, suspended again in cold distilled water, and left stood at 10° C. for two hours. The planospore suspension was explored for its absorbance using ultraviolet visible light spectroscopy analysis system (DU series 600, Beckman), and its concentration adjusted such that its absorbance at wavelength 500 nm becomes 0.068 ($10^5$ zoospores/ml) before use as inoculum.

4. Preparation of Body Component Elicitor

According to the method of Doke and Tomiyama, (1980) (See Reference 14), hyphal wall components (HWC) of *Phytophthora infestans* were prepared as follows. Mycelia of *Phytophthora* were placed in standing culture in 100 ml conical flask containing 30 ml of rye medium at 20° C. for two weeks. Mycelial mat collected was washed with tap water, had its humidity removed by suction filtration, and cryopreserved at −80° C. The frozen mycelia were milled in mortar, and suspended in 50 mM of acetate buffer (pH 4.5) of 5 times the weight of mycelia. The suspension was sonicated for five minutes using Sonicator (W-225R Heat System-Ultrasonics Inc.) at 45 W output, and centrifuged at 14,000×g for 30 minutes. The resultant precipitate was suspended in 50 mM acetate buffer (pH 4.5) of the weight equivalent to that in the previous step, and supersonication and centrifugation performed under conditions again similar to the previous step. The precipitate thus obtained was suspended in 0.1 M borate buffer (pH 8.8) of the weight equivalent to the original weight of mycelia, sonicated under the similar condition to the above, autoclaved at 120° C. for 20 minutes, and centrifuged at 14,000×g for 30 minutes to collect the supernatant. On the other hand, its precipitates was again suspended in 0.1 M borate buffer (pH 8.8), sonicated and autoclaved before centrifugation. Supernatant obtained by the centrifugation was combined with the previous supernatant, and dialyzed through dialysis tube (exclusion limit molecular weight; 12,000) against water at 4° C. for 24 hours. The solution after the dialysis was combined with an equivalent volume of diethylether using a separatory funnel, and left stood. Emulsion layer was collected, and its ether was vacuum desiccated using evaporator. The resultant concentrate was added an appropriate amount of water before lyophilization. The lyophilized preparation thus obtained was used as HWC in the following experiments. The HWC was sonicated using a sonicator at 45 W output for three minutes and suspended in water before use.

5. Preparation of Potato Tuber Disc

Potato tuber discs were prepared as follows. Potato tubers (Cultivar Rishiri) that had been stored at 4° C. were washed extensively with tap water, and immersed in 1% sodium hypochlorite for 10 minutes. The tubers were bored out with a cork borer (20 mm in diameter) in axial direction to produce columnar pieces of soft tissue. The columnar pieces were then sliced by microtome into discs of 2 mm thickness. The discs thus prepared were washed with cold distilled water (about 4° C.), aligned in a plastic chamber, left stood under humidified darkness, and aged for 21 hours. All of these procedures were conducted under darkness.

6. HWC Treatment and Pathogen Inoculation

The potato tuber discs prepared according to the method described in the above section 5 were pretreated with 100 μl each of distilled water, and left stood for three hours. The discs were then treated with 1 mg/ml HWC, or with 100 μl distilled water as control. When inoculating the discs with potato *Phytophthora*, 100 μl each of suspension ($10^5$ spores/ml) was inoculated while rotating in order to obtain a uniform density of planosphore. When inoculating potato leaves with the pathogen, each of the leaves was pretreated with 500 μl of distilled water, and left stood for three hours before 500 μl each of suspension was inoculated while rotating in order to obtain a uniform density of planosphore on each leaf tissue.

The discs and leaf tissues after the treatment and inoculation were left stood at 20° C. under humidified darkness for a selected time period. After this treatment, a set consisting of three pieces of the potato tuber discs and eight leaf tissues were wrapped in an aluminum foil, placed in liquid nitrogen for cryopexy, and stored at −80° C.

7. Extraction of Total RNA from Potato Leaves or Tubers

Extraction of total RNA was performed according to the method described in Yoshioka et al. (1996) (See Reference 52). 2 g each of potato leaves or tuber discs were milled while being added liquid nitrogen in mortar, put into a sterilized centrifuge tube that had been treated with DEPC and contained 5 ml of extraction buffer [100 mM Tris-HCl (pH 9.0), 100 mM NaCl, 1% SDS], 1 ml of 2-mercaptoethanol, 2.5 ml of 1 M Tris (pH 9.0) saturated phenol, 2.5 ml of chloroform isoamylalcohol (24:1; v/v), thoroughly suspended, and centrifuged (8,000 rpm, 15 minutes). To the collected supernatant, one twentieth amount of 5 M sodium chloride, 5 ml isopropanol were added, and the mixture left stood at −20° C. for one hour. Centrifugation (8,000 rpm, 15 minutes) of the mixture produced precipitates, to which 5 ml guanidium salts buffer [4 M guanidine thiothianate, 25 mM sodium acetate (pH 7.0), 0.5% N-lauroyl sarcosine, 20 mM 2-mercaptoethanol], 500 μl 2M sodium acetate (pH 4.0), 5 ml water-saturated phenol, 1 ml chloroform/isoamylalcohol (49:1, v/v) were added and thoroughly suspended, and the mixture centrifuged (8,000 rpm, 15 minutes). 5 ml isopropanol was added to the supernatant collected, and the mixture left stood at −20° C. for one hour. Precipitates produced by centrifugation (8,000 rpm, 15 minutes) of the mixture was suspended in 300 μl guanidium salts buffer, a equivalent amount of isopropanol added, and the mixture left stood at −20° C. for one hour. Centrifugation (12,000 rpm, 15 minutes) produced precipitates, which was washed with 500 μl 3M sodium acetate (pH 5.2) at room temperature, and centrifuged (12,000 rpm, 15 minutes). This washing step was repeated twice. Further, the mixture was washed with 500 μl of 70% ethanol, and centrifuged (15,000 rpm, 15 minutes). Precipitates thus obtained was dissolved in 100 μl of DEPC treated water to provide a total RNA sample.

8. Northern Analysis

The total RNA was fractionated by formaldehyde agarose gel electrophoresis (See Reference 37), and then transferred to and immobilized on Hybond-$N^+$ nylon membrane (Amersham) using alkaline blotting (See Reference 36). As a probe, leaf PVS1 cDNA was used.

Nylon membrane with RNAs adsorbed thereon was left stood in prehybridization solution [50% formamide, 5× Denhartz solution (See Reference 37), 5×SSPE (See Reference 37), 0.5% SDS, 100 μg/ml heat-denatured salmon sperm DNA (Pharmacia)] at 42° C. for over one hour. $^{32}P$ labeled DNA probe was added and hybridized at 42° C. for over 16 hours. The membrane was washed sequentially in 0.1% SDS-containing 4×SSPE at room temperature for 15 minutes (twice), in 0.1% SDS-containing 4×SSPE at 60° C. for 15 minutes, and then in 0.1% SDS-containing 2×SSPE at 60° C. for 15 minutes (once). Autoradiography was performed using X-rays film OMAT-AR (Kodak) and intensifying screen Lighting Plus (Dupont) at −80° C.

9. RT-PCR

RT-PCR was performed using RT-PCR high-Plus (TOYOBO). For cDNA synthesis, 1.0 μg of total RNA, 10 pmol/μl of antisense primers and 10 pmol/μl of antisense primers were used to perform 25 cycles of amplification reaction at 94° C. (one minute), 47° C. (one minute). The primers used were as follows, with the site for annealing onto corresponding cDNAs shown in FIG. 23.

```
                                         (SEQ ID NO:9)
PVS1:     5'-AGGAGATTGTTCGCCCCATA-3'
          and (SEQ ID NO:10)(469 bp)
          5'-TCTCCATGAGTCCTTACATG-3',
          or (SEQ ID NO:11)
          5'-CATCGATTGTTTTGTACATCTG-3'
          and (SEQ ID NO:12)(176 bp)
          5'-AATAATGATACAAAAAAAAATTAAGG-3'

(SEQ ID NO:13)
PVS2:     5'-TATCAATTCACCAAGGAACACT-3'
          and (SEQ ID NO:14)(132 bp)
          5'-GAAGTAATTAAATTTAAATATTATCAA-3'

(SEQ ID NO:15)
PVS3:     5'-TTGTCTGCTGCTGCTTGTGG-3'
          and
```

-continued

```
                                  (SEQ ID NO:16) (326 bp)
        5'-TCTCCATGAGTCCTTACATG-3'

(SEQ ID NO:17)
PVS4:   5'-AGGACATTGTTCGACCTGTT3'
        and (SEQ ID NO:18) (469 bp)
        5'-TCTCCATGAGTCCTTACATG-3',
        or (SEQ ID NO:19)
        5'-CATCCCTTAAAATTATAAGTATTC-3'
        and (SEQ ID NO:20) (131 bp)
        5'-AATAATGATACAAAATAAATTAAGG-3'
```

The cDNAs thus synthesized were fractionated by 2% agarose gel electrophoresis and stained with ethidium bromide to determine the presence or absence of bands (See Reference 37).

10. Preparation of Soluble Fractions from Potato Tuber

Soluble fractions were prepared from potato tuber discs according to the partially modified method of Dixon and Fuller, (1978) (See Reference 13).

A set of three pieces of potato tuber disc was wrapped in an aluminum foil, and stored at −80° C. in cryopexy in liquid nitrogen. The frozen potato tuber discs were milled with pestle while being added liquid nitrogen. To the potato tuber powder thus obtained, 2 g of polycra AT, a phenol absorbant, was added, and agitated with pestle. Subsequently, 7 ml of extraction buffer [0.1 M sodium borate (pH 8.8) 1 mM PMSF (phenylmethylsulfonyl fluoride), 10 mM 2-mercaptoethanol] was added to bring the mixture into suspension, and cool-centrifuged (14,000 rpm, 20 minutes, 4° C.). The resultant supernatant was stored at −80° C.

11. Expression of Fusion Protein in *E. coli* and its Extraction

In order to obtain antigen for use in antibody production, potato PVS was expressed in *E. coli*. Full length of translatable region of PVS1 cDNA was inserted into expression vector pET-32b(+)(Takara Shuzo) that had been cleaved with EcoRI and XhoI, and the resultant vector was introduced into *E. coli*. (BL21, Novagen). The *E. coli* was then plated on LB agar medium containing 50 μg/ml carvenicilin, and cultured at 37° C. overnight. 50 mL of LB liquid medium with 200 μg/ml carvenicilin was poured into four 500 ml flasks, into which single colonies were stripped off and suspended. The flasks were shake-cultured (140 rpm) at 37° C. until $A_{600}$=0.6. 250 μl of the sample in the flasks was used as pre-induction protein sample to confirm the expression of fusion proteins. Subsequently, IPTG was added to the final concentration of 1 mM to induce the expression of proteins, and shake-cultured at 37° C. (140 rpm) for three hours. After cooling on ice for 5 minutes, the medium was centrifuged (5,000 rpm, 10 minutes). Supernatant was removed, and precipitates was resuspended in 5 ml *E. coli* suspension [50 mM Tris-HCl (pH 8.0), 2 mM EDTA], and 100 μl of which was used as post-induction protein sample to confirm the induced expression of fusion proteins. The medium was again centrifuged (5,000 rpm, 10 minutes), supernatant removed, and precipitates of *E. coli* was used to confirm the solubility of fusion proteins.

Confirmation of induced expression of fusion proteins as well as confirmation of solubility was conducted as follows. The pre-induction and post-induction protein samples that have been sampled in the above manner were centrifuged (5,000 rpm, 30 seconds) to remove supernatant, and precipitates resuspended in 100 μl of *E. coli* suspension. 10 μl each of each suspension was sampled to perform SDS-PAGE and Western analysis. SDS-PAGE and Western analysis were performed according to the section 14. "SDS-PAGE and Western analysis". After confirming the induced expression, *E. coli* precipitates having the expression of fusion proteins induced was suspended thoroughly in ice-cooled 5 ml Binding Buffer [5 mM imidazole, 0.5 M sodium chloride, 20 mM Tris-HCl (pH 7.9)]. The suspension was transferred into transparent centrifuge tubes, which were ice-cooled while the *E. coli* inside was being broken by ultrasonicator. The suspension was centrifuged (12,000 rpm, 10 minutes), and supernatant provided as soluble fraction. To the precipitates, 5 ml urea containing Binding Buffer (6 M urea plus Binding Buffer) was added, resuspended, the suspension centrifuged (12,000 rpm, 10 minutes), and supernatant obtained as urea fraction. After 10 μl each of soluble fraction and urea fraction were sampled, SDS-PAGE and Western analysis were performed. The SDS-PAGE and Western analysis were performed according to the section 14. "SDS-PAGE and Western analysis".

Since the fusion proteins were found in the urea fraction, the urea was gradually removed to regenerate the structure of produced protein. Production of proteins was conducted as follows. The urea fraction was transferred into dialysis tubes, and dialyzed against 200 ml of 4 M urea dialysate [4 M urea, 10 mM Tris-HCl (pH 7.0), 5 mM DTT] at 4° C. for one hour. The dialysate was exchanged to 200 ml of 2 M urea dialysate (4 M urea dialysate with its urea concentration changed to 2 M), and dialyzed at 4° C. for one hour. The dialysate was further exchanged to 200 ml of urea-free dialysate (4 M urea dialysate with its urea removed) and dialyzed at 4° C. for one hour. The dialysate was again exchanged to 200 ml of urea-free dialysate (4 M urea dialysate with its urea removed), and dialyzed at 4° C. overnight. The dialysed solution was transferred into Eppendorf tubes, and centrifuged (15,000 rpm, 10 minutes), and supernatant transferred into new tubes. This fraction served as regenerated fraction, and was used as antigen for production of antibody. As a result of such procedures, 4 ml of 8 mg/ml fusion proteins was obtained.

12. Production of Anti-PVS Antibody

Mouse (BALB/c, female, 4-week-old) was bred for five days, and injected peritoneally with 100 μl of emulsion containing 100 μg solution of fusion protein expressed in *E. coli* admixed with an equivalent amount of Complete Freund Adjuvant (DIFCO). One week later, 100 μl of emulsion containing the 100 μg fusion protein admixed with an equivalent amount of Incomplete Freund Adjuvant (DIFCO) was peritoneally injected. 10 days later, the mouse was bled at their tail, and explored by Western Analysis for production of antibody against HMGR. Since an antigen-antibody reaction was revealed, 100 μl of emulsion containing 100 μg fusion protein admixed with an equivalent amount of Incomplete Freund Adjuvant (DIFCO) was again peritoneally injected. One week later, blood was collected and left stood at 4° C. overnight to have blood clot precipitated. The blood was centrifuged (10,000 rpm, 15 minutes), small amount of supernatant aliquoted as antisera into Eppendorf tubes, and stored at −80° C.

13. Quantification of Protein

Concentration of proteins in samples were quantified according to the method of Bradford (1976) using protein quantification kit (BIO-RAD). Calibration curves were generated using BSA.

14. SDS-PAGE and Western Analysis

SDS-PAGE on protein samples were performed according to the method described in Laemmli (1970). 10 μl of sample was mixed with 10 μl of sample buffer [50 mM Tris-HCl (pH 8.5) containing 2% SDS, 10% mercaptoethanol, 0.002% BPB, 20% glycerol], boiled for five minutes, ice-cooled, and run on 10% polyacrylamide gel for electrophoresis.

Western analysis was performed according to the method described in Towbin et al. (1979)(See Reference 55). Gel after SDS-PAGE, paper filter, and nitrocellulose membrane (PRO-TPRAN, Schleicher and Schuell) were immersed in transfer buffer (0.1 M Tris, 0.192 M glycine, 20% methanol, 0.1% SDS), respectively, for 30 minutes, placed on a stage of semi-dry blotter (ATTO) and driven with 2 mA/cm$^2$ of constant current for 60 minutes to transfer the protein in the gel onto nitrocellulose membranes. The nitrocellulose membranes were shaken in TBS-T [50 mM Tris-HCl buffer (pH 7.6) containing 137 mM sodium, 0.1% Tween 20] containing 5% skimmed milk overnight, for blocking. The membranes were then washed in TBS-T for 15 minutes once, and for 5 minutes twice, and shaken in TBS-T containing as primary antibody anti-potato PVS antibody (2,000 times dilution) for one hour. The membranes were again washed in TBS-T, and shaked in TBS-T containing anti-mouse-Ig antibody (Amersham) as secondary antibody for 30 minutes. The membranes were washed in TBS-T, and then signals detected using ECL detection kit (Amersham) on Hyper Film (Amersham).

15. Production of Probes

Using plasmids containing introduced potato PVS1 to 4 cDNA as templates, the primers shown in FIG. 23 were used to amplify them by PCR that occurs specifically for nucleotide sequence of each of the genes. The reaction was performed by using 2 ng plasmids having TaKaRa Taq™ (Takara Shuzo) and insert DNA integrated, on DNA thermal cycler PJ2000 (Perkin Elmer Cetus) in 25 cycles of at 94° C. for one minute (heat denaturation), at 53° C. for 45 minutes (annealing), and at 72° C. for two minutes (DNA elongation). The sizes of DNA fragments amplified were examined on 0.8% agarose gel electrophoresis. The DNA fragments were purified from the gel using QIAquick Gel Extraction Kit (QIAGEN).

16. Screening of Potato Genomic Library

As genomic library, commercially available potato genomic library (potato cv. Desiree, Clontech) was used.

Phage clones were selected using plaque hybridization (See Reference 37). Phage solution that had been adjusted to contain 30,000 plaques per plate was mixed with 200 μl of host *E. coli* XL1-Blue MRA (P2) strain 10 mM magnesium sulfate, $A_{600}$=2), left stood at 37° C. for 20 minutes, mixed with 3 ml NZYM top-agarose (1% NZ amine, 0.5% yeast extract, 10 mM magnesium sulfate, 0.5% sodium chloride, 0.6% agarose), and superposedly inoculated on NZYM agar medium (1% NZ amine, 0.5% yeast extract, 10 mM magnesium sulfate, 0.5% sodium chloride, 1.5% agar powder). After culturing at 37° C. until the diameter of plaques reached to about 0.5 mm, the plates were left stood at 4° C. for over one hour. The plaques on the plates were adsorbed on Hybond-N$^+$ nylon membrane (Amersham), treated with denaturation solution (1.5 M NaCl, 0.5 M NaOH) for 7 minutes and with neutralization solution [1.5 M sodium chloride, 0.5 M Tris-HCl (pH 7.2), 1 mM EDTA] for 3 minutes, and washed with 2×SSPE. Subsequently, the DNAs were immobilized on the membranes using 0.4 M sodium hydroxide, and washed with 5×SSPE (twice). Clones of interest were selected from 6.0×10$^5$ clones in total.

After the primary screening, PVS1, PVS3 and PVS4 were selected the bands of which were of the sizes as predicted by PCR using primers specific for each of the PVS1 to 4 members, and used in secondary and tertiary screening.

Production of probes, hybridization, washes, and autoradiography were conducted similarly as described in the section 18. "Southern Hybridization."

17. Isolation and Purification of Phage DNA

Isolation and purification of phage DNA were performed according to the method of liquid culture (See Reference 23) and polyethylene glycol (PEG) precipitation (See Reference 37) as follows. Plaques of interest were harvested from agar, transferred to 1.5 ml tubes containing 100 μl of SM solution [50 mM Tris-HCl (pH7.5), 0.1 M sodium chloride, 7 mM magnesium sulfate, 0.01% gelatin] and 1 μl of chloroform, left stood at 4° C. overnight, and thoroughly suspended. Using 200 ml flask, host *E. coli* [XL1-Blue MRA (P2) strain] was shake-cultured in 80 ml NZYM (1% NZ amine, 0.5% yeast extract, 10 mM magnesium sulfate, 0.5% sodium chloride) at 30° C. overnight. Host *E. coli* that had precipitated upon centrifugation (8,000 rpm, 3 minutes, 4° C.) was collected and suspended in 10 mM magnesium sulfate to $A_{600}$=2. 500 μl of host *E. coli* suspension thus prepared and 50 μl of phage suspension were mixed, left stood at 37° C. for 20 minutes, and shake-cultured using 50 ml NZYM at 37° C. to ensure bacteriolysis. 2.9 g sodium chloride and 0.4 ml chloroform were added, and the mixture shaked for further 10 minutes. Supernatant produced by centrifugation (10,000 rpm, 10 minutes, 4° C.) was collected, one fifth as much of which supernatant of 50% PEG 6000 was mixed, and the mixture left stood in ice for one hour. Precipitate produced by its centrifugation (12,000 rpm, 20 minutes, 4° C.) was collected and suspended in 400 μl Tris-Mg-NaCl [10 mM Tris-HCl (pH7.5), 49.6 mM sodium chloride, 4.9 mM magnesium chloride]. To the solution, 4 μl of 10 mg/ml RNase A (Sigma) and 4 μl of 10 mg/ml DNase I (Sigma) were added, the mixture treated at 37° C. for one hour, and chloroform extraction performed three times. 2×STE [80 mM Tris-HCl (pH7.5), 2% SDS, 0.5 M EDTA] in an amount equivalent to the upper layer collected, and one fifth as much of 10 mg/ml proteinase K were added, the mixture treated at 65° C. for 10 minutes and extracted in a time course by the same volume of Tris saturated phenol, phenol:chloroform:isoamylalcohol (25:24:1, v/v/v), chloroform:isoamylalcohol (24:1, v/v). To collected upper layer, twice as much of cold ethanol was added and the mixture left stood at −20° C. for 30 minutes, and centrifuged (12,000 rpm, 10 minutes, 4° C.) to collect precipitates. The precipitates was washed with 70% ethanol, vacuum dried and dissolved in 100 μl of $H_2O$.

18. Southern Analysis

Total DNAs of clones of interest were digested with selected restriction enzymes (Takara Shuzo), and fractionated by 0.8% agarose gel electrophoresis (See Reference 37). Fractionated DNA fragments were transferred onto Hybond-N$^+$ nylon membranes (Amersham) by alkaline blotting (See Reference 36).

$^{32}$P labelled DNA probes were prepared, by random priming (Feinberg and Vogelstein, 1983) using [α-$^{32}$P] dCTP (ICN Biochemicals) and Megaprime DNA Labelling systems (Amersham).

The nylon membranes with DNA adsorbed thereon were left stood in prehybridization solution [5×Denhardt Solution (See Reference 37), 5×SSPE (See Reference 37), 0.5% SDS, 100 μg/ml heat-denatured salmon sperm DNA (Pharmacia)] at 42° C. for over one hour, added $^{32}$P labelled DNA probes, and hybridized at 42° C. for over 16 hours. The membranes were then sequentially washed in 0.1% SDS-containing 2×SSPE for 10 minutes (twice), and in 0.1% SDS-containing 1×SSPE for 10 minutes (once). All of these washes were done at room temperature. Autoradiography was performed using X-rays film OMAT-AR (Kodak) and intensifying screen Lighting Plus (Dupont) at −80° C.

19. Preparation of Plasmid

Subcloning of the subject DNA fragments for sequencing was performed using pBluescript KS+ (Stratagene).

Total DNAs of the subject clones were digested with selected restriction enzymes (Takara Shuzo) and fractionated by 0.8% agarose gel electrophoresis (See Reference 37). The DNA fragments of interest were purified using QIAquick Gel Extraction Kit (Qiagen). Vectors that have been digested with restriction enzymes were dephosphorylated by treatment with Alkaline phosphatase E. coli C75 (Takara Shuzo) (37° C., one hour) and extracted in a time course with phenol:chloroform:isoamylalcohol (25:24:1, v/v/v), chloroform:isoamylalcohol (24:1, v/v). To collected upper layer, twice as much of cold ethanol and one twentieth as much of 3 M NaCl were added, and the mixture left stood at −20° C. for 30 minutes and centrifuged (12,000 rpm, 10 minutes, 4° C.) to collect precipitates. The precipitates were washed with 70% ethanol, vacuum dried, and dissolved in 20 μl TE[10 mM Tris-HCl (pH 8.0), 1 mM EDTA]. The vector and inserts prepared in the above manner were adjusted to become in molar ratio 1:1 of vector: insert, and ligated with DNA Ligation Kit ver. 2 (Takara Shuzo). E. coli JM109 Compatible Cell (Takara Shuzo) was transformed with plasmid DNA that had been ligated, inoculated on LB/Amp/X-gal/IPTG agar medium (1% Bacto Tripton, 0.5% yeast extract, 1% sodium chloride, 0.1 mg/ml ampicillin solution, 0.004% X-gal solution, 0.5 mM IPTG solution, 1.5% agar powder), and left stood at 37° C. overnight. Single colonies that were obtained bay blue-white selection were cultured in LB/Amp liquid medium (2 ml LB, 0.1 mg/ml ampicillin) overnight, and their plasmid DNA isolated. Extraction and purification of plasmid DNA were performed using FlexiPrep Kit (Amersham Pharmacia Biotech).

20. DNA Sequencing and Database Analysis

Sequencing of nucleotides was performed using PRISM Dye Deoxy Termination Cycle Sequencing Ready Reaction Kit (Applied Biosystems) based on deoxy-termination method (See Reference 38). Determination of mobility of the reactant in modified polyacrylamide gel and sequencing were performed using ABI 373S DNA sequencer•DNA sequence automatic analyzer (Applied Biosystems). Binding between nucleotides, amino acid sequence in reading frame and any homology to known genes were analyzed using BLAST program (See Reference 1) on the super computers of National Institute of Genetics, DNA Data Bank of Japan (DDBJ). Alignments of amino acid sequences were performed using CLUSTAL w program (See Reference 43).

21. Transient Assay Using Potato Tuber Protoplasts

A transient assay using potato tuber protoplasts were performed as follows according to the method described in Hashimoto et al. (1992) (See Reference 18). 25 μg of transgenes were added to 800 μl of solution (0.5 M mannitol, 0.1 mM $MgSO_4$, pH 7.0) containing 1×10⁶ protoplasts derived from potato cultured cells, gently mixed by pipetting, and left stood on ice for 10 minutes. The solution was tranferred into cuvettes that had been cooled, and electroporated with gene transfer apparatus CUY21 (Tokiwa Science) at constant current (60 v, 50 pon, 75 poff, 4 times). The solution was transferred into centrifuge tubes, left stood on ice for 10 minutes, had its supernatant removed, added 900 μl of culture medium, transferred to 12-well culture plates, and left stood at 20° C. in darkness for one hour. Those protoplasts into which vectors containing a deduced promoter region for PVS3 had been electroporated were added 100 μl of sterilized water or 100 μl of 1 mg/ml HWC, and left stood for 12 hours. Those protoplasts as positive control into which vectors containing a promoter region for CaMV 35S had been electroporated were left stood for 12 hours. After removing supernatant, the protoplasts were washed with 1×PBS, and luciferase activity was measured using Dual-Luciferase Reporter Assay System (Promega).

22. Production of Transgenic Plant and its GUS Staining

Figure 11:
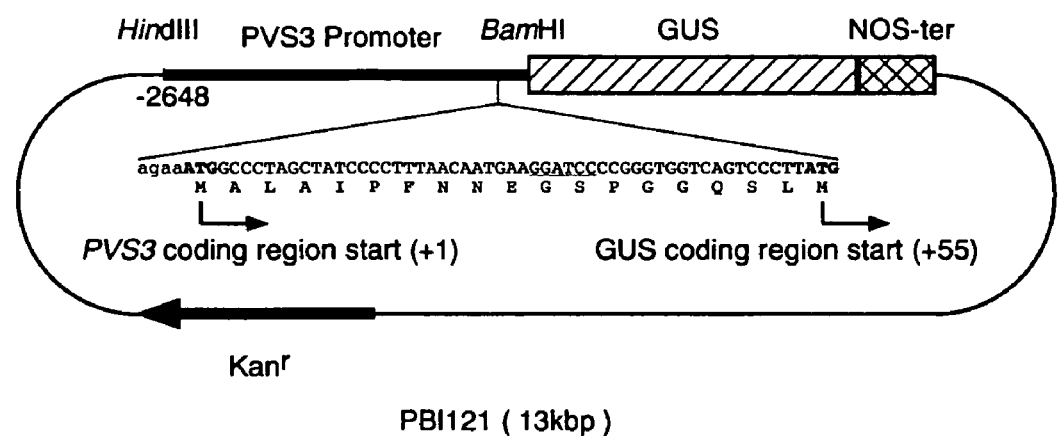
FIG. 11 Schematic representation of the construct of PVS3 promoter. GUS reporter gene. (SEQ ID NOS 44 & 45 disclosed respectively in order of appearance)

Production of transgenic plant and its GUS staining were performed according to the method of Jefferson (1987) (See Reference 19). For production of transgenic plant, pedicles of aseptically cultured MayQueen were used. CaMV35S promoter of transforming vector pBI121 (Clonetech) was deleted, deduced PVS3 promoter region 2,648 bp upstream of its translation start codon was linked upstream of GUS gene via BamHI such that GUS will be translated in-frame (FIG. 11). The vector was introduced into Agrobacterium tumefaciens LBA4404 (Clonetech) by electroporation. Ablated pedicles were immersed in culture solution of A. tumefaciens for 2 minutes for infection, and left stood on 3C5Zr medium [Sucrose 30 g, GellanGum 2 g, MS mineral (10×) 100 ml, Fe-EDTA 5 ml, Myo-inositol 100 ml, 3C5ZR vitamin (Thiamin HCl 1 mg/ml 1 ml, Nicotinic acid 1 mg/ml 0.5 ml, Pyridoxine HCl 1 mg/ml 0.5 ml, Asparatic acid 1 mg/ml 0.4 ml) 2.4 ml, IAA (0.1 mg/ml) 5.3 ml, Zeatin riboside (0.1 mg/ml) 17.5 ml, pH 5.9, per 1,000 ml] in dishes at 23° C. for three days. The pedicles were then transferred to 3C5Zr medium containing kanamycin (100 μg/ml) and Cefotaxime (300 μg/ml). This step was repeated every week, until shoots bud out at which time point the pedicles were transferred into S1 regeneration medium (Sucrose 15 g, GellanGum 3 g, S1 mineral (10×) 100 ml, Fe-EDTA 5 ml, V2 vitamin 2.0 ml, pH 5.7, per 1,000 ml) to confirm regeneration of roots.

For GUS staining, plant tissues were vacuum penetrated with GUS stain solution [X-Gluc (50 mg/ml in DMF) 100 μl, 500 mM Phosphate buffer (pH 7.0) 1 ml, 100% Methanol 2 ml, 0.5% Triton X-100 7.9 ml, per 10 ml] and stained at 37° C. in darkness overnight. The stained tissues were then boiling-decolored in acetate:ethanol:glycerol (1:3:1) decoloring solution, and visualized. For microscopic study of the inoculated potato Phytophthora, the tissues stained were boiled in lactophenol solution (lactic acid 10 ml, phenol 10 g, glycerol 10 ml water 10 ml, 40 ml ethanol), and this step was repeated. Subsequently, the tissues were placed on paper filters soaked in chloral hydrate (2.5 g/ml) for two days at 4° C. in darkness to destain and visualized (See Reference 49).

23. Transient Assay Via Agrobacterium tumefaciens in Potato Leaf Tissue

Transient assay via A. tumefaciens was performed according to the method of Chang et al. (2002) (See Reference 7). Rifampicin (50 μg/ml) and selected antibiotics were added to A. tumefaciens LBA4404 into which binary vectors containing Cf-9/Avr9 or StMEK$^{DD}$ (SEQ ID NO:7) had been electroporated, and the mixture cultured. The A. tumefaciens were collected by centrifugation (3,000 rpm, 15 minutes), suspended in introduction buffer (1/10× Murashige-Skoog salts, 1/10× B5 vitamins, 2% sucrose, 1% glucose, 150 μM acetosyringone, 20 mM MES pH 5.4), and its concentration adjusted to $OD_{600}$=0.1. 1 ml sylinge was used to inject the suspension from the back of the leaf, and GUS staining was performed two days later.

Example 1

Expression Profile of PVS Gene in Potato Tuber Tissue Inoculated with *P. infestans*

Figure 2:
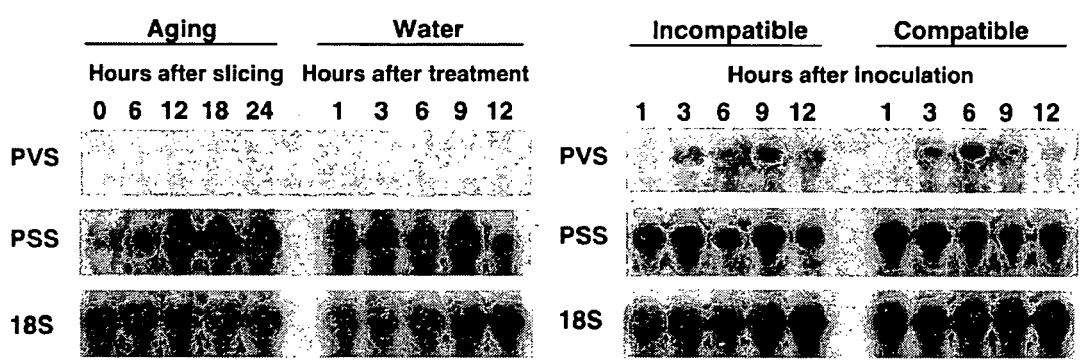
FIG. 2 Expression of PVS (potato vetispiradiene synthase) and PSS (potato squalene synthase) genes in aged potato discs after inoculation with $P.$ infestans. Potato discs were aged for 24 hr prior to inoculation with $10^4$ zoospores per discs of race 0 (incompatible) or of race 1, 2, 3, 4 (compatible), or treatment with water.

Potato tuber tissues were inoculated with compatible and incompatible races, water-treated, and had their total RNA extracted from three tuber discs to perform Northern analysis using PVS1 cDNA. The results of the analysis are shown in FIG. 2. Accumulation of PVS mRNA was found in both compatible and incompatible interactions.

Example 2

Each PVS1 to 4 Member Specific RT-PCR in Potato Tuber Tissue Inoculated with *P. infestans*.

Figure 3:
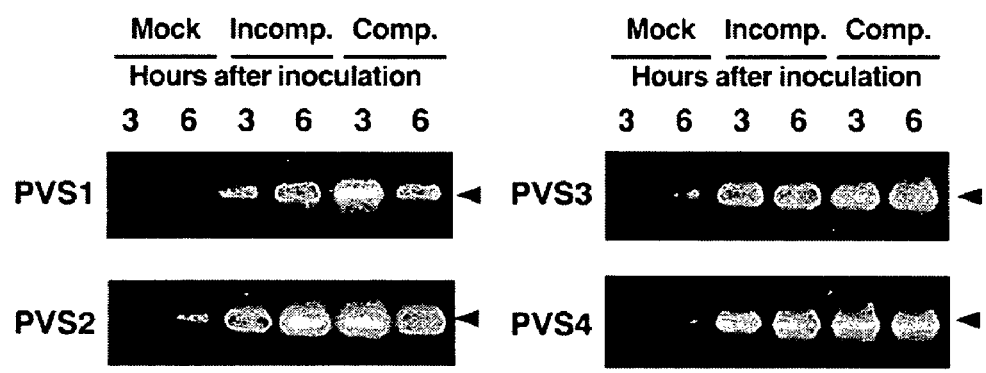
FIG. 3 RT-PCR using the total RNA from aged potato discs after inoculation with incompatible (Incomp.) or compatible (Comp.) race of $P.$ infestans or, treatment with water (Mock). Clone specific-primers of PVS1, PVS2, PVS3, and PVS4 were used for PCR and will generate products of 469, 132, 326, and 469 bp, respectively.

In order to determine which of the PVS1 to 4 members were expressed in potato tuber tissues, total RNA was extracted from three discs of potato tuber that had been inoculated with compatible and incompatible races, water-treated and frozen three or 6 hours later to perform RT-PCR using primers (SEQ ID NO: 9, 10, 13, 14, 15, 16, 17, and 18) specific for each of the PVS1 to 4 members. Bands having predicted sizes of 469 bp, 132 bp, 326 bp and 469 bp were detected for PVS1 to 4, respectively in both compatible and incompatible interactions. (FIG. 3).

Example 3

Western Analysis of PVS Proteins in Potato Tuber Tissue Inoculated with Incompatible Race and Compatible Race In order to determine if the accumulation pattern of PVS mRNA was reflected upon actual protein synthesis, anti-potato PVS antibody was produced to perform Western analysis. In order to obtain antigen for use in antibody production, expression in *E. coli* was effected based on deduced amino acid sequence. PVS1 cDNA translated region prepared by PCR was inserted into an expression vector, and expressed in *E. coli* as fusion protein with thioredoxin. SDS-PAGE was performed on total *E. coli* proteins before and after induction of expression, and the gels stained with CBB solution. As a band of approximately 83 kD in size was detected in the urea fraction, the fraction was used as antigen for antibody production after removal of urea by dialysis.

Figure 4:
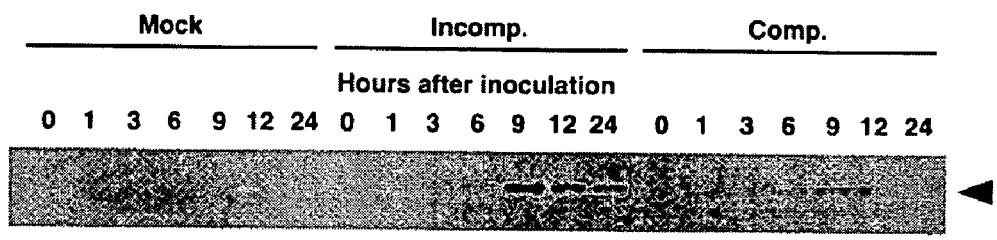
FIG. 4 Western blot analysis using total proteins from aged potato discs after inoculation with the incompatible (Incomp.) or compatible (Comp.) rave of $P.$ infestans, or treatment with water (Mock). Each 10 μg total proteins were separated by SDS-polyacrylamide gel electrophoresis and immunoblotted using antiserum against PVS. The detection was carried our using HRP-linked anti-mouse Ig and ECL detection kit.

The titer of resulted antibody was determined to detect 10 ng of antigen when used in 1,000-fold dilution. Since the antibody was thus determined to have enough titer for further use in Western analysis, soluble fractions were prepared from potato tuber discs that had been aged for 24 hours, at different time points up to 24 hours post water-treatment or inoculation with incompatible race or with compatible race, to perform Western analysis using anti-potato PVS antibody (FIG. 4). In 6 hours, accumulation of PVS proteins was found in both compatible and incompatible interactions. On the other hand, no accumulation of PVS proteins was found in water treatment area. These results may support the results of FIG. 2 that accumulation of PVS mRNA peaks 6-9 hours after pathogen inoculation.

Example 4

RT-PCR Specific to Each PVS1 to 4 Member in Potato Leaf Inoculated with *P. infestans*

Figure 5:
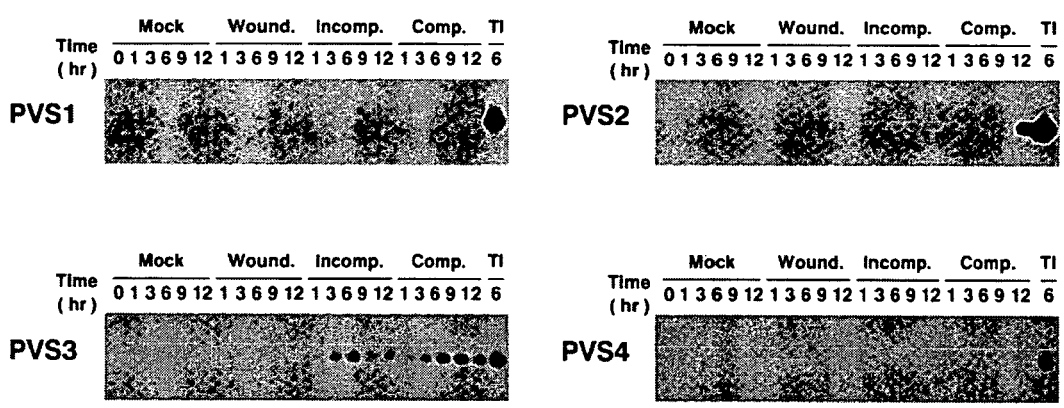
FIG. 5 RT-PCR using total RNA from potato leaves treated with water (Mock) or after wounding (Wound.), or inoculation with the incompatible (Incomp.) or compatible (Comp.) race of $P.$ infestans. Lane TI; RT-PCR products from potato tuber 6 hr after inoculation with the incompatible race of $P.$ infestans were loaded as a positive control. Member specific-primers of PVS1, PVS2, PVS3, and PVS4 were used for PCR and will generate products of 176, 132, 326, and 131, respectively. RT-PCR products were separated by agarose gel electrophoresis and blotted onto nylon membranes. Membranes were hybridized with each $^{32}P$ labeled PCR product.

In order to determine which of the PVS1 to 4 members were expressed in potato leaf tissues, total RNA was extracted from three potato leaves at different sequential time points up to 12 hours post inoculation with compatible and incompatible races, water treatment and wound treatment, to perform RT-PCR using primers (SEQ ID NO: 11, 12, 13, 14, 15, 16, 19, and 20) specific to each of the PVS1 to 4 members. Subsequently, Southern analysis was performed using cDNA probes specific to each of the PVS1 to 4 members. Only one band indicative of significant accumulation of mRNA corresponding to a predicted size of 326 bp representing PVS3 was detected in both compatible and incompatible interactions (FIG. 5). In addition, when RNA derived from tuber tissue used as positive control was used, bands of predicted sizes 176 bp, 132 bp, 326 bp and 131 bp representing PVS1-4, respectively, were detected (FIG. 5).

Example 5

Screening of Potato Genomic Library

In view of the fact that genomic size of potato is 1.6 to $1.8 \times 10^9$ bp per haploid (See Arumuganathan and Earle, 1991), that average size of potato genomic library is $1.5 \times 10^4$ bp per plaque, and that potato is quadloid, in order to screen all of the potato chromosomes, at least $5.2 \times 10^5$ plaques must be screened. Thus, using full length PVS1 cDNA was used as probe to screen $6.0 \times 10^5$ plaques. As a result of primary screening, 87 clones were found. In order to distinguish PVS1 to 4 among the clones and obtain their deduced promoter regions, primers specific for each member of PVS1 to 4 were constructed to obtain distinct PCR products for electrophoresis. 3 clones were selected for each of PVS1, PVS3 and PVS4 and used in further secondary and tertiary screening.

Clones obtained by the screening were separately digested with EcoRI, HindIII or XhoI, and subjected to Southern hybridization using as probes the PCR products that had been obtained with the primers used in the screening. As a result, bands that hybridized with these probes were detected. Since it was found that clones of interest were obtained, the hybridized DNA fragments obtained by EcoRI and HindIII digestion were subcloned into pBluescript KS+ vector and sequenced.

Example 6

Determination of DNA Sequence and Database Analysis

Figure 8:
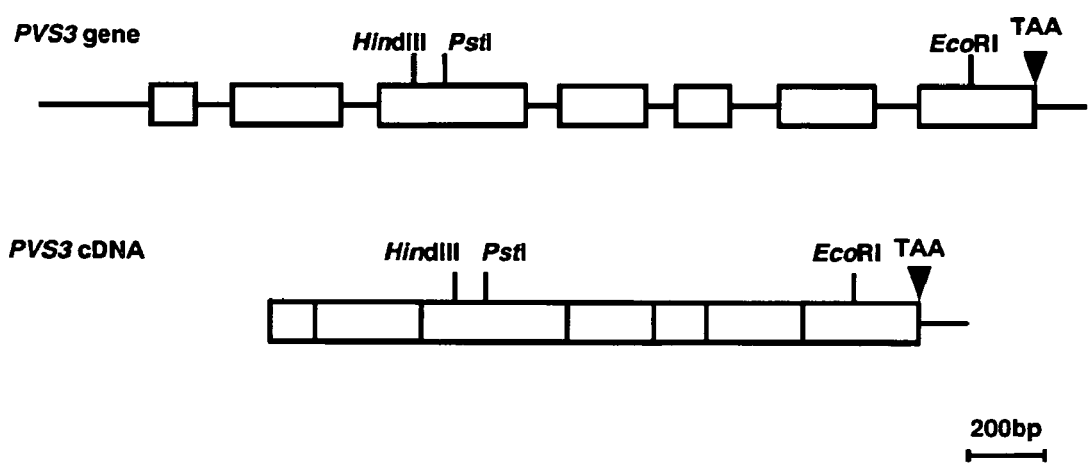
FIG. 8 Restriction and structural maps for PVS3 genomic clone and cDNA clones. Coding regions are represented by open boxes with introns shown as thick lines. Vertical bars correspond to intron positions.
Figure 9:
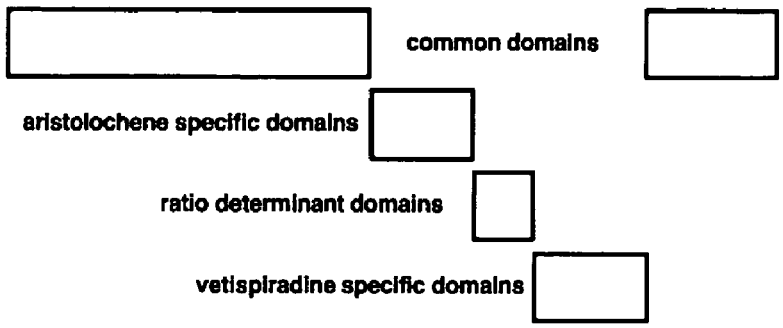
FIG. 9 A schematic representation of an amino acid sequence alignment between $N.$ tabacum (TEAS) $S.$ tuberosum (PVS) $H.$ muticus (HVS) $C.$ annum (PEAS). Sequence alignments used deduced amino acid sequence corresponding to exons. Solid vertical bars correspond to intron positions within the $N.$ tabacum, $S.$ tuberosum, $H.$ muticus and $C.$ annum genes. Numbers within the boxes indicate the number of amino acids encorded by exon. Percentages refer to identity scores between the indicated domains, and H, C, and DDXXD (or DDXX) refere to conserved histidine-, cysteine-, and aspartate-rich (and known as the substrate binding site) residues.

The DNA fragments of PVS1, PVS3 and PVS4 subcloned were sequenced entirely (FIGS. 6, 7, 8 and 9). In FIGS. 6 and 7, promoter region (SEQ ID NO:1) and coding region (SEQ ID NO:21) were shown. In order to examine PVS3 cDNA and genomic structure of PVS3, PVS3 cDNA that had been already isolated (See Reference 53) was compared with PVS3 genomic DNA sequence obtained in the present Example. In PVS3, it was found that all of the nucleotide sequences and deduced amino acid sequences, except for 3'-untranslated region, coincide with each other, with 6 introns intervening (FIG. 8). On the other hand, both of the PVS1 and PVS4 are intervened by 5 introns, unlike PVS3 (FIG. 9). It is known that cultivars of potato plants are quadloid, with their genome having a plurality of isogenes (Reference 56). Since the PVS3 genomic clone obtained in the present Example differs from PVS3 cDNA only in 3'-untranslation region, it may encode one of PVS3 subfamilies.

Back and Chappel (1996) reported functional differentiation of sesquiterpene cyclase (See Reference 4). Deduced amino acid sequences of 5-epi-aristolochin synthase which is sesquiterpene cyclase for tobacco (TEAS), and *capsicum* (PEAS), and vetispiradiene synthase for henbane (HVS) and potato (PVS) were compared. Between HVS and PVS3 or PVS4, among the same VSs, identity over 90% was found in the vetipiradine specific domain (FIG. 9). On the other hand, the identity between PVS3 and PEAS was below 80%. Further, in aristolochene specific domain where substrate binding site lies, the identity between PVS and TEAS, or between PVS and PEAS were 78% to 89%, whereas the identity between PVS and HVS was found to be as high as over 98%. In addition, it was found that those sesquiterpene cyclase which are expressed in leaf tissue consist of 7 exons intervened by 6 introns, whereas those PVS1 and PVS4 which are expressed in potato tuber tissue consist of 6 exons with 5 introns intervening (FIG. 9).

Example 7

HWC Responsiveness of PVS3 Promoters by Transient Assay Using Protoplast pGL3 vector constructed with deduced PVS3 promoter region linked upstream luciferase was electroporated into protoplasts to examine HWC responsiveness (FIG. 10). Compared to water-treatment area, HWC treatment area had a significantly high luciferase activity, thus demonstrating that the 2,648 bp region upstream the translation start codon used in the present experiment is responsive to elicitors.

Example 8

Expression Behavior of PVS3 Gene in Transgenic Plant

Figure 12:
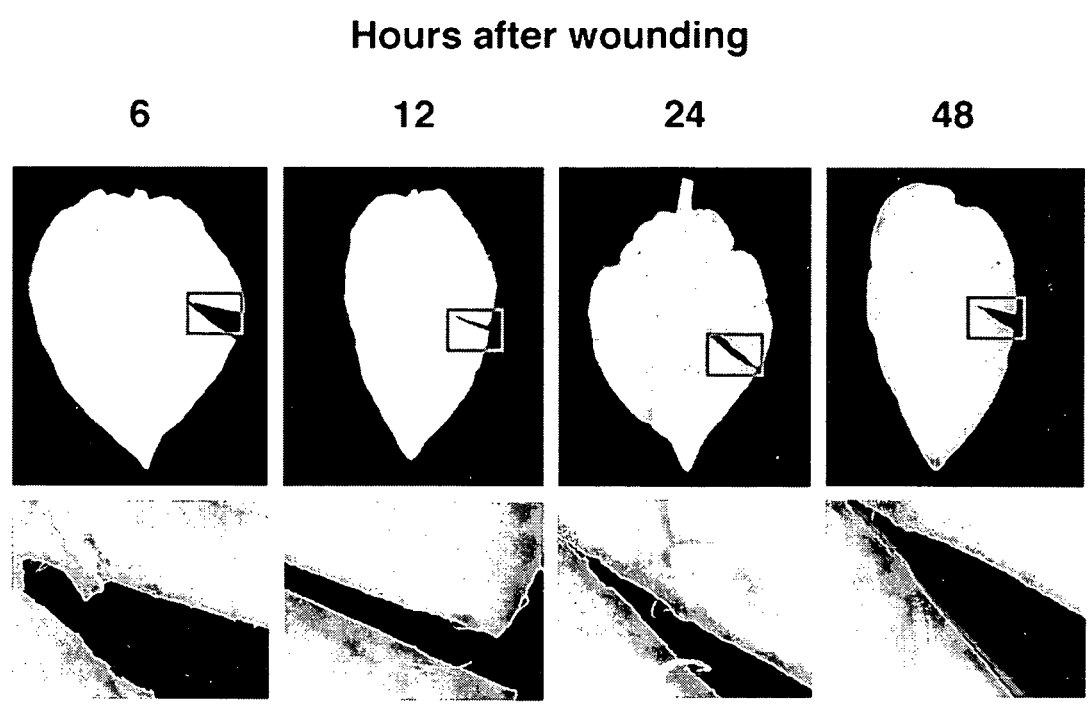
FIG. 12 Expression pattern of GUS driven by PVS3 promoter in response to wounding. Transgenic potato leaves carrying PVS3 promoter were used.
Figure 1:
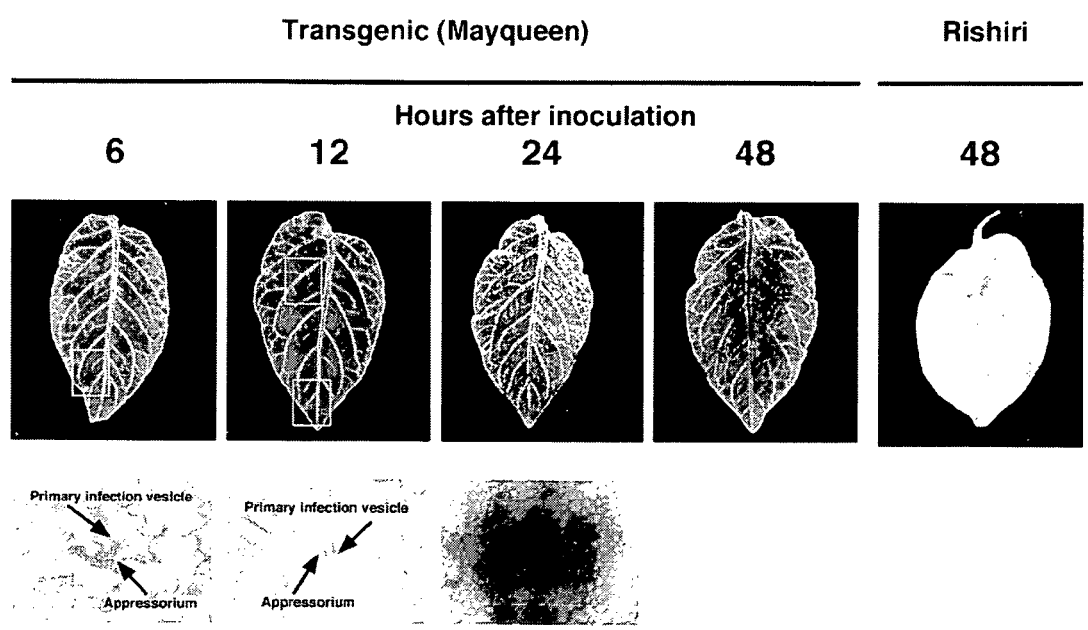

In order to closely examine any expression behavior of PVS3, binary vectors (FIG. 11) constructed with deduced PVS3 promoter region linked upstream GUS gene were transduced into MayQueen having no true resistance gene against potato *Phytophthora* to produce transformants. In order to examine the responsive ness of PVS3 gene to wound, a portion of the transgenic potato leaf tissue was resected and stained with GUS sequentially in a time course (FIG. 12). As a result, no GUS staining was detected at resected site even after 48 hours, thus demonstrating that the promoter of interest lacks responsiveness to wound.

In order to examine any response to *P. infestans*, compatible race was inoculated and microscopic observation was performed. GUS staining was observed in invaded cells within 6 hours (FIG. 13). Further, 48 hours after inoculation, an intense expression was observed on the entire leaves inoculated. These indicate that the promoter of interest is responsive to infection with compatible race of *P. infestans*.

Figure 14:
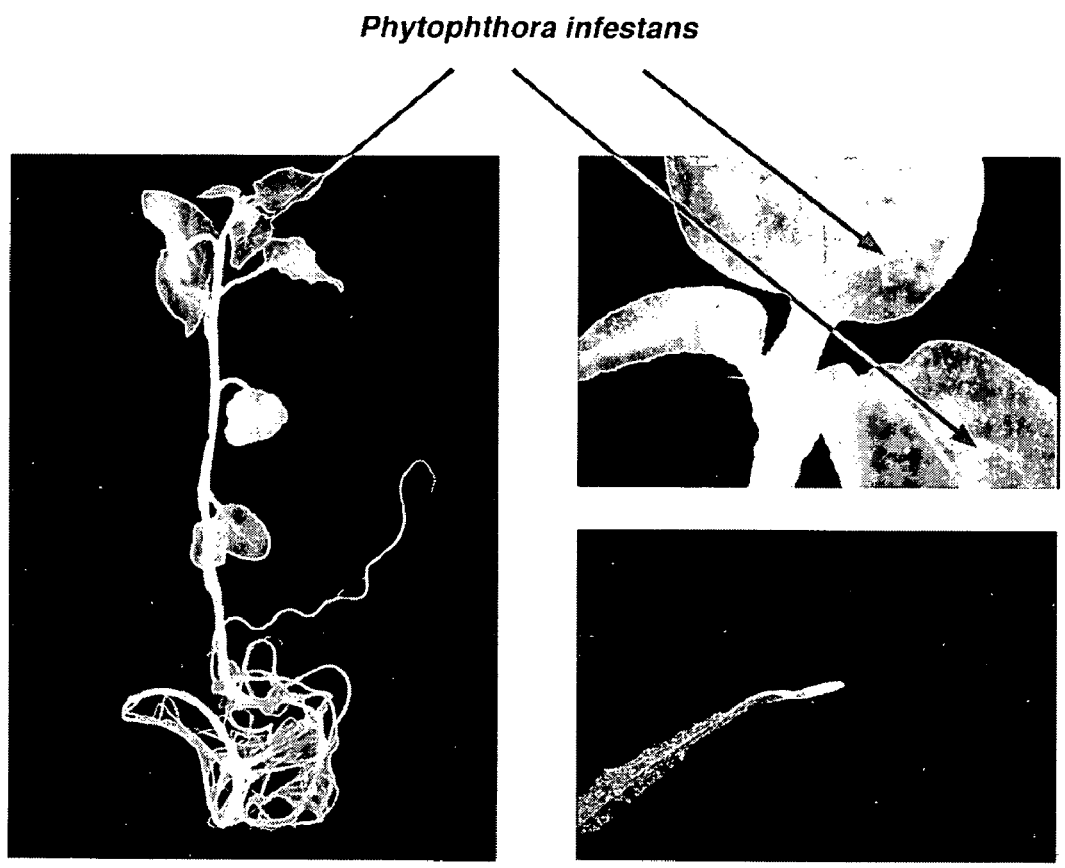
FIG. 14 Expression pattern of GUS driven by PVS3 promoter in transgenic potato plants. GUS activity of transgecin potato plants was detected by GUS staining solution solution. Arrows indicate $P.$ infestans inoculation areas as GUS staining control.

In order to examine the existence of any organ constantly expressing the present promoter, an entire transgenic potato plant was GUS stained (FIG. 14). Except for *Phytophthora* inoculated leaf tissue used as positive control of GUS staining (FIG. 14), no staining was observed at any location such as growing points and roots. This result indicates that the present promoter is pathogen-responsive specifically.

Figure 15:
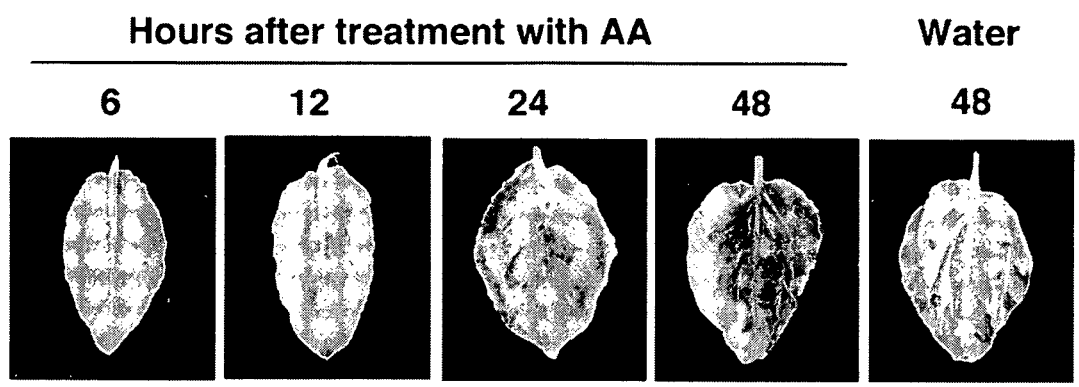
FIG. 15 Expression pattern of GUS driven by PVS3 promoter in response to arachidonic acid (AA). AA (5 mM) or water was injected into transgenic potato leaves. GUS activity was detected using GUS staining solution 6, 12, and 24 hr after injection.

In order to examine to which of disease signals the present promoter is responsive, leaf tissue was treated with a variety of elicitors and stained with GUS (FIGS. 15, 16, 17 and 18). It was found that when treated with arachidonic acid which is a constituent fatty acid of *P. infestans*, the tissue was GUS-stained in 24 hours (FIG. 15). On the other hand, when treated with hydrogen oxide which is one of reactive oxygen species, or with glucose/glucose oxidase which produces hydrogen peroxide, or with salicylic acid which is involved in systemic acquired resistance, the tissue was not GUS-stained (FIGS. 16, 17 and 18).

Figure 19:
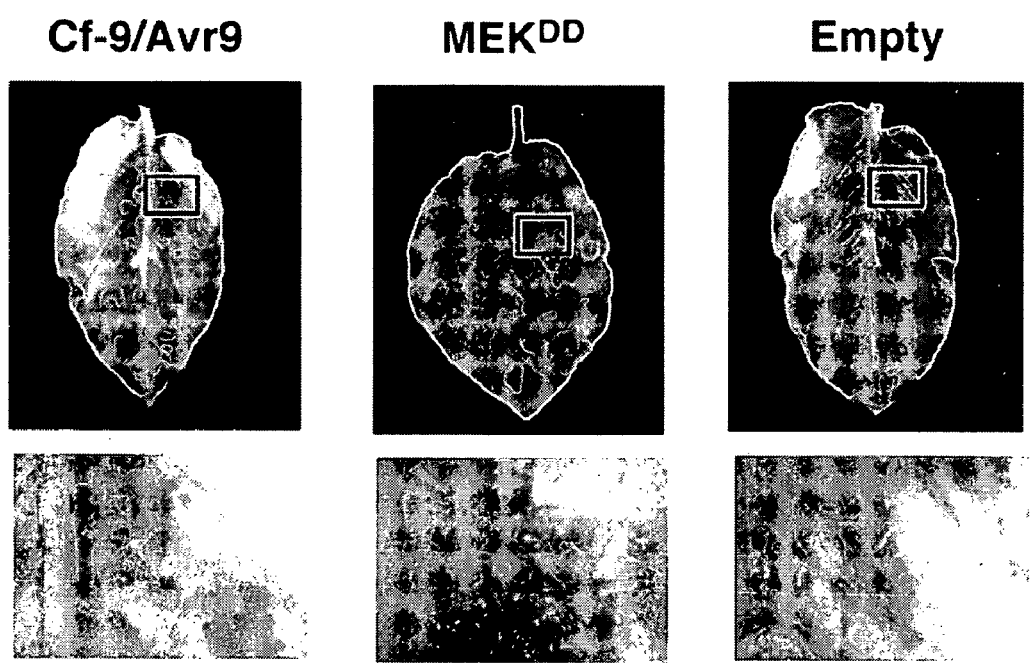
FIG. 19 Expression pattern of GUS driven by PVS3 promoter in response to Cf-9/Avr9 interaction or StMEK$^{DD}$. Agrobacterium carrying 35S:Cf-9/Avr9, StMEK$^{DD}$ or empty vector (control) was infiltrated into transgenic potato leaves. GUS activity was detected using GUS staining solution 2 days after Agrobacterium infiltration.

It is well known that when resistance gene product Cf-9 of a tomato form responds to corresponding Avr9 which is a specific elicitor of tomato leaf fungus *Cladosporium fulvum*, communication mechanism is triggered, thereby inducing hypersensitive reaction (See Reference 41). When Cf-9/Avr9 was transiently expressed via *Agrobacteria* in leaf tissue, GUS staining resulted (FIG. 19). Further, when constitutive active mutant enzyme StMEK$^{DD}$ (SEQ ID NO:7, 8) which phosphorylates and activates salicylic acid-induced protein kinase (SIPK) and wound-induced protein kinase (WIPK) known to be downstream of these resistance genes and control a variety of protective responses was expressed, GUS staining similarly resulted (FIG. 19). On the other hand, in leaf tissue inoculated with *Agrobacteria* containing the binary vector as control without any insert, no GUS staining was found.

HMG-CoA reductase (HMGR) genes that play an important role in rishitin synthesis constitute a multigene family (FIG. 1). HMG1 contributes to steroid glycoalkaloid synthesis in response to wound, whereas HMG2 and HMG3 are known to be induced by pathogen signal and contribute to rishitin synthesis (See Reference 9). It is reported that PVS genes in potato plants also constitute a multigene family, and that there are PVS1 to 4 members (See Reference 53). In the present study, in order to examine expression pattern of PVS 1 to 4 members in potato tuber tissue and leaf tissue, RT-PCR was performed using primers specific for each of these members. Total RNA extracted from potato tuber discs that had been inoculated with compatible and incompatible races of *P. infestans* was used as template in performing the RT-PCR (FIG. 3). Regardless of which race had been inoculated, bands were detected which correspond to predicted sizes of all of PVS1 to 4 members. These results may indicate that, at least in tuber tissue, the PVS members may not have distinctive roles for metabolic fluctuation in response to stimuli.

In order to examine whether the accumulation pattern of PVS mRNA is reflected upon PVS protein synthesis in potato tuber tissue, anti-potato PVS antibody was produced to perform Western analysis (FIG. 4). Accumulation of PVS proteins was found 6 to 24 hours after inoculation with incompatible race and compatible race. It has been reported, as a result of Northern analysis using total RNA extracted from potato tuber tissue, there was a transient accumulation of PVS mRNA that peaked 6 to 9 hours after inoculation in areas where incompatible and compatible races had been inoculated (FIG. 2, Reference 53). In view of the accumulation profile of PVS mRNA, the half-life of PVS proteins is expected to be long. Further, it has been reported that PVS enzyme activity increases in soluble fraction prepared from potato tuber tissue inoculated with either of incompatible race and compatible race (See Reference 54). This report contradicts another report that accumulation of phytoalexin is induced only by inoculation with incompatible race (See Reference 40). For phytoalexin biosynthesis in potato, HMGR enzyme, which biosynthesizes mevalonic acid from 3-Hydroxy-3-methylglutaryl CoA (HMG-CoA), and PVS enzyme, which biosynthesizes vetispiradiene from farnesyl diphosphate, are thought to be two major factors (See References 29, 54, and 9) (FIG. 1). It is reported that HMGR activity is significantly increased only in incompatible interaction, whereas it is decreased with time in compatible interaction (See Reference 52). In view of the activity profile of HMGR, the specific phytoalexin synthesis control between potato cultivars and physiological races of *P. infestans* is determined by supply of mevalonic acid. In order to confirm this scenario, it may be necessary to examine whether or not those phytoalexins in the forms of lubimin and rishitin are accumulated by externally supplying tuber tissues that had been inoculated with compatible race with farnesyl diphosphate, which is substrate of PVS.

The first actual tissue infected with *P. infestans* is leaf tissue. In the present study, in order to examine which of PVS1 to 4 members are expressed by attack of *P. infestans*, total RNA extracted from leaf tissue in a time course after inoculation with compatible and incompatible races and treatment with water was used as template to perform RT-PCR (FIG. 5). In both compatible race and incompatible race interactions, it was found that only PVS3 was significantly induced. It is known in general that rishitin does not accumulate in potato leaf tissues (See Reference 34). However, an observation has been reported that rishitin is synthesized transiently also in leaf tissues (See Reference 26). Although the role of rishitin in leaf tissues in protective response is not yet known, the fact that PVS3 is induced by inoculation of compatible race allows construction of disease by resistance plant utilizing the present promoter. Thus, in order to obtain PVS3 promoter, genomic clone was isolated. As a result of screening, PVS1, PVS3 and PVS4 were obtained (FIGS. 6, 7, 8, 9). Comparison between the PVS3 genomic clone isolated this time and PVS3 cDNA that has been already isolated revealed a coincidence across all of the deduced amino acid sequences. Restriction enzyme sites in exon regions agreed with each other in a corresponding manner (FIG. 8).

Capsidiol, which is a phytoalexin for tobacco and *capsicum*, and rishitin produced by henbane and potato are synthesized by similar biosynthesis pathways (See Reference 4 and 29) (FIG. 1). Sesquiterpene cyclase involved in the former is 5-epi-aristolochin synthase (EAS), and EAS for tobacco (TEAS) and *capsicum* (PEAS) are extremely similar in amino acid level (See Reference 53). Back and Chappell constructed various chimeric genes using TEAS and HVS cDNA for henbane, and synthesized proteins from chimeric genes in *E. coli* (See Reference 4). By adding farnesyl diphosphate, which is a substrate for EAS and VS, to soluble fraction of the recombinant proteins, and by quantifying production ratio of 5-epi-aristolochin or vetispiradiene, any region controlling the activity of both enzymes was predicted. Comparison of deduced amino acid sequences defined by each exon according to their report revealed, in vetipiradiene specific domain, over 90% identity between HVS of henbane and PVS4 or PVS3. In aristolochene specific domain where substrate bringing site lies, identity of 78% to 89% was found between PVS and TEAS or PEAS, whereas identity of over 98% was found between PVS and HVS (FIG. 9). This result supports the theory asserted by Back and Chappell (See Reference 4). It was further found that PVS1 and PVS4 consist of 6 exons intervened by 5 introns, whereas PVS3 and other sesquiterpene cyclase that are expressed in leaf tissue consist of 7 exons intervened by 6 introns (FIG. 9). Miyata (1984) assumed that those introns in mitochondria genome that lacked any function to facilitate an efficient replication are deleted, thereby shortening DNA in the process of evolution. Based on his theory, it may be envisioned that the fifth intron of PVS1 and PVS4 expressed in tuber is a product of deleted intron and shortening in the process of evolution.

For creation of disease resistant plant utilizing a promoter, it may be necessary to analyze and identify PVS3 promoter region. In the present Example, GUS gene was linked downstream of deduced promoter of PVS3 to produce transgenic potato plant and closely examine the responsiveness of the present promoter. Interestingly, the present promoter was not only unresponsive to wound (FIG. 12), but it also caused no staining either at any growth point or root (FIG. 14). There is a report of construction of transgenic tobacco plant carrying GUS gene similarly linked downstream of TEAS, sesquiterpene cyclase of tobacco plant, and of its expression pattern (See Reference 51). The researchers reported, even at a low level, responsiveness to wound, and GUS activity in roots and pedicles. According to this report, PVS3 promoter in potato leaf tissue and TEAS promoter in tobacco leaf tissue may have distinct manner of response. In tobacco leaf, capsidiol, a type of phytoalexin, is accumulated to a high concentration in response to pathogen attack and elicitor treatment. In contrast, there is no rishitin accumulation found in potato leaf tissue, and PVS3 mRNA accumulation is at so low a level as to be detected by RT-PCR (FIG. 5). Based on these facts, the specific responsiveness of PVS3 promoter may attribute to the low level of expression.

Figure 20:
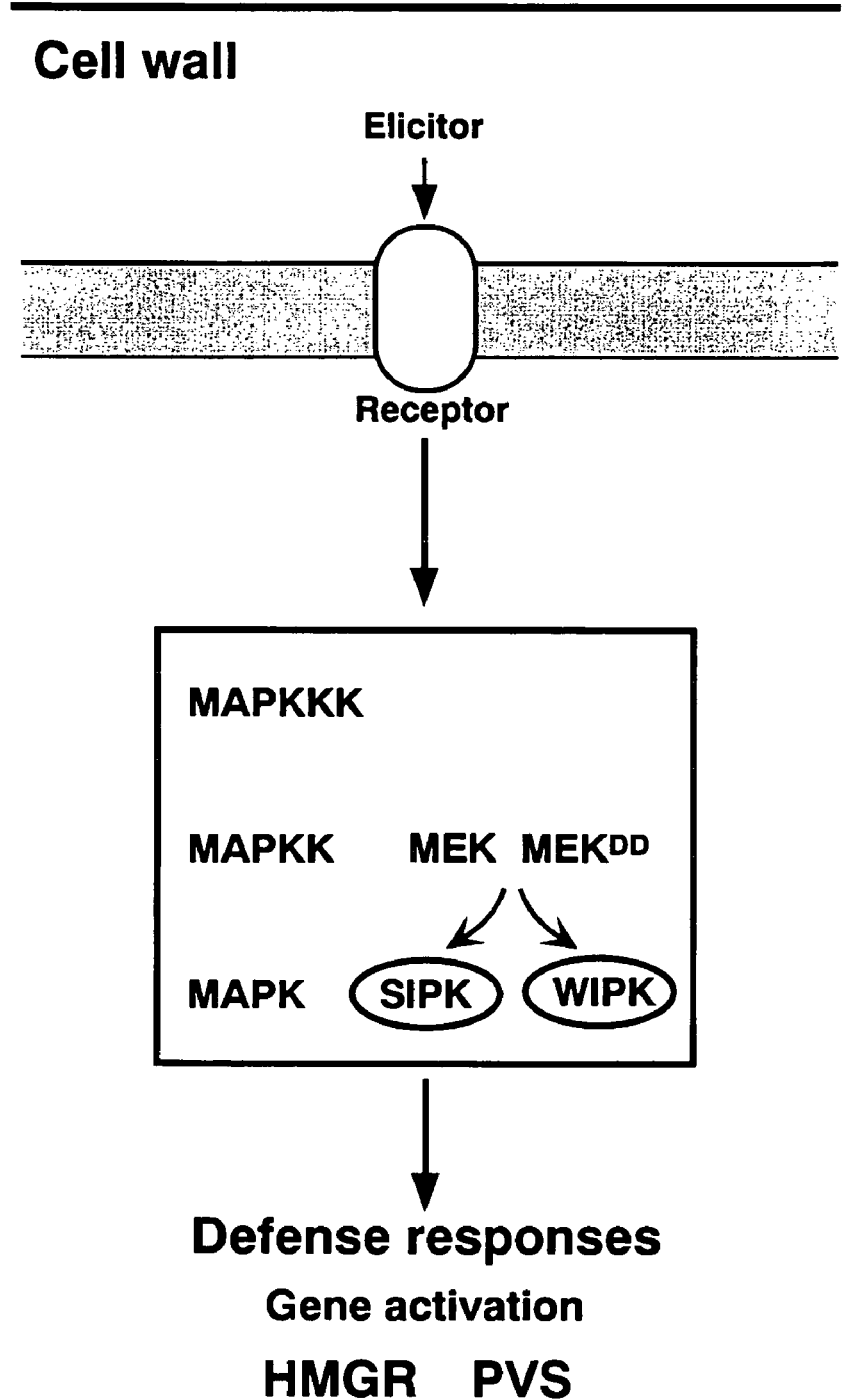
FIG. 20 Schematic representation of elicitor-Induced signal transduction. MAPKKK; mitogen-activated protein kinase kinase kinase, MAPKK; mitogen-activated protein kinase kinase, MAPK; mitogen-activated protein kinase, SIPK; salicylic acid-induced protein kinase, WIPK; wound-induced protein kinase, HMGR; 3-hydroxy-3-methyglutaryl CoA reductase, PVS; potato vetispiradiene synthase.
Figure 2:
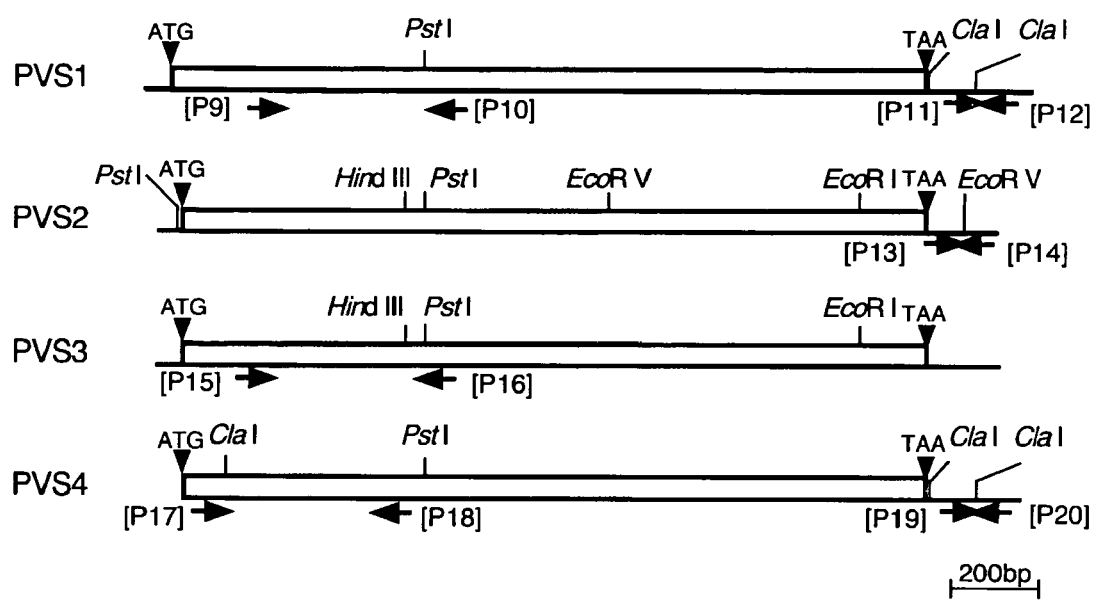

Recently, it has been reported that HMGR gene expression is controlled by SIPK, a type of mitogen-activated protein (MAP) kinase (See Reference 33). Also in the present study, when constitutive active mutant enzyme StMEK1$^{DD}$ (See Reference 50) was expressed which phosphorylates and activates SIPK and WIPK, GUS activity was found (FIG. 19). Further, when Avr9, which is a specific elicitor by tomato leaf fungal disease fungus *Cladosporium fulvum*, and Cf-9, which is a resistance gene product of tomato cultivar, were transiently expressed in leaf tissue via *Agrobacteria*, GUS staining resulted (FIG. 19). Romeis et al. reported that when those tobacco plant and cultured cell which have transformed Cf-9 were treated with Avr9, SIPK and WIPK were activated (See Reference 35). Based on these findings, PVS3 promoter may be controlled by SIPK, similarly to HMGR gene. This inference may be supported by the fact that treating potato tuber tissue with HWC or arachidonic acid activates MAP kinase corresponding to SIPK (See Reference 20). A predicted communication pathway behind these events is shown in FIG. 20.

MAPK cascade is one of the most important factors of signal transduction pathway in plants and has drawn an intense focus in recent years (Reference 65). SIPK and WIPK, among others, have been implicated in expression of disease resistance in plants (Reference 57). MAPKKK located upstream of MAPK cascade is known to phosphorylate and activate MAPKK, which in turn phosphorylates MAPK, thereby triggering a variety of protective responses. It has been recently shown that when Benthamiana (*Nicotiana benthamiana*), a type of tobacco, was caused to overexpress a constitutive active mutant enzyme StMEK1$^{DD}$ for StMEK1, a MAPKK, SIPK and WIPK were activated to induce 5-epi-aristolochin synthase (TEAS), a sesquiterpene cyclase of tobacco plant (Reference 64). It is readily expected that MAPK cascade is involved also in potato PVS gene regulation, similarly to tobacco plant. In the following Example, virus-induced gene silencing (VIGS) was used to explore this possibility. VIGS has come into focus in recent years as effective gene knock down method useful in analyzing function of plant genes (Reference 59). VIGS is one of biophylaxis against viruses wherein transcription product of any host gene that has a high homology with viral gene is specifically degraded. Since those mRNA which are 80% or more homologous with any plant gene fragment introduced into virus is degraded, in general, this method is useful for knocking down not only one sole gene but also its multi-gene family. This method can also be readily and quickly performed, compared to production of transformant or mutant. Above all, numerous studies have been reported concerning potato X virus (PVX) and Benthamiana system as method for retrospective genetic functional analysis (References 67 and 70). Hence, SIPK and WIPK were knocked down by VIGS, and the above described PVS3:GUS transiently introduced into leaf tissue via Agrobacteria to examine PVS3 promoter activity.

In the following Examples 9 through 12, biological materials, reagents, experimental procedures and other details are as follows. Unless otherwise specified, materials and other items are similar to those used in the above Examples.

1. Tested Plant

As tested plant, Benthamiana (*Nicotiana benthamiana*) provided by Leaf Tobacco Research Center, Japan Tobacco, Inc., was used. Benthamiana was seeded on Kureha soil (Kureha Chemicals) contained in polyethylene pots, which were then placed in an incubato at 25° C. to develop the plant under light for 24 hours. For transient assay using *Agrobacterium* (*Agrobacterim tumefaciens*), 6 through 8 leaves from plants 30 through 35 days post seeding were used.

2. Preparation of INF1

As Infestin with which to treat Benthamiana leaf, a fusion protein expressed in *E. coli* (*Escheruchia coli* strain pBF53) having FLAG-ATS vector comprising inf1 gene introduced was used (Reference 62). The fusion protein was prepared as follows.

Each *E. coli* was shake-cultured (140 rpm) overnight in LB liquid medium containing 50 µg/ml ampicillin at 37° C. The *E. coli* culture medium was added to LB liquid medium containing 100-fold amount, i.e. 50 ppm, of ampicillin, and shake-cultured (140 rpm) at 37° C. further to the optical density of $OD_{600}$=0.6. IPTG was added to the final concentration of 1 mM to induce expression of protein, shake-cultured (140 rpm) for three hours at 37° C., and then centrifuge the culture medium (5,000×g, 10 minutes). Supernatant was filtrated, transferred to dialysis tubes (exclusion limit molecular weight 3,500), and dialyzed against sterile distilled water at 4° C. for 24 hours. Fraction thus obtained was adjusted to the protein concentration of 10 mg/ml, to provide FLAG-INF1 solution. For use in treating plant, the INF1 solution was diluted 3-fold with distilled water.

3. Construction of Binary Vector Harbouring Inserted PVS3 Promoter with GUS Gene Linked.

Figure 25:
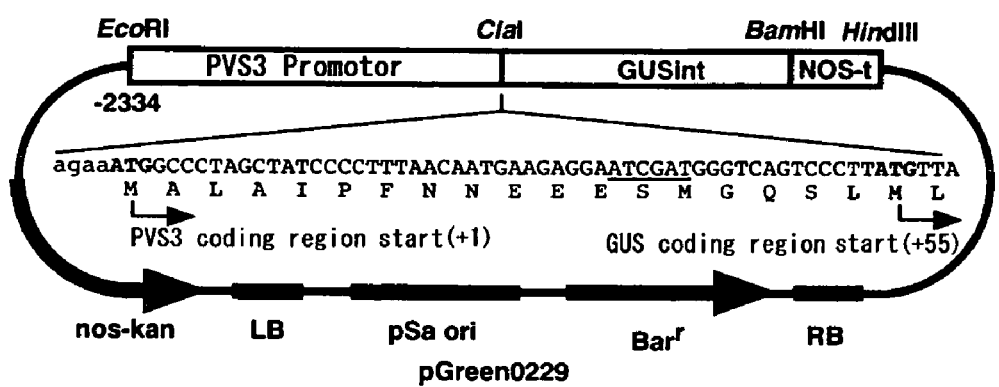
FIG. 25 shows the construction of a binary vector including PVS promoter region used in the transient assay. GUS gene includes introns. (SEQ ID NOS 46 & 47 disclosed respectively in order of appearance)

Expression vector for use in MUG assay was constructed as follows. Using PVS3 genomic clone as template, primers with restriction enzyme sites (EcoRI or ClaI) added were used (FIG. 24) to amplify nucleotide sequence comprising deduced promoter region and PVS3 gene coding region start site by PCR. The PCR reaction was performed using KOD -Plus- DNA Polymerase (Toyobo), with annealing temperature of 55° C., according to an attached protocol. The PCR product was digested with EcoRI and ClaI, fractionated by electrophoresis on 1% agarose gel, and DNA fragments of interest purified with QIAquick Gel Extraction Kit (Qiagen) and used as insert. As vector, pGreen 0229 (See Hellens et al. 2000) including GUS gene comprising introns was used, digested with EcoRI and ClaI, and fractionated by eletrophoresis on 1% agarose gel, similarly to the insert. DNA fragments of interest were purified using QIAquick Gel Extraction Kit and used as vector. The vector and insert thus prepared were adjusted to 1:3 in vector:insert in molar ratio, and ligated with DNA Ligation Kit ver. 2 (Takara). *E. coli* JM109 Compatible Cell (Takara) was transformed with ligated plasmid DNA, inoculated on LB agar medium [1% tryptone peptone, 0.5% yeast extract powder, 1% NaCl, 50 µg/ml kanamycin, 1% agarose], and cultured at 37° C. overnight. Single colonies were cultured on 2 ml LB liquid medium [1% tryptone peptone, 0.5% yeast extract powder, 1% NaCl, 1% agarose] containing kanamycin solution (50 µg/ml) at 37° C. overnight, and plasmid DNA recovered. Map of binary vector with PVS3 promoter inserted is shown in FIG. 25.

4. Construction of Deletion Clone for Use in Transient Assay in Benthamiana Leaf Using as template the GUS expression vector constructed in the section 3 above, primers with added restriction enzyme sites (EcoRI or ClaI) starting with deletion points of interest (FIG. 24) were used to amplify nucleotide sequence comprising deduced promoter region and PVS3 gene encoding region starting site by PCR. This PCR was performed using KOD -Plus- DNA Polymerase (Toyobo), with annealing temperature of 55° C., according to the attached protocol. Binary vector was prepared according to the procedure described above in the section 3, and introduced into *Agrobacteria* according to the method described in the section 6. Deletion clones obtained were confirmed to be free of error in nucleotide sequence.

5. Construction of StMEK1$^{DD}$ Expression Vector

Expression vector for use in MUG assay in Benthamiana was constructed as follows. Nucleotide sequence of StMEK1$^{DD}$ (See Reference 64) comprising 5' untranslated region was amplified by PCR using primers (5'-TT<u>GGGCCC</u>ATGCGACCTCTTCAACCACC-3': SEQ ID NO: 36, 5'-G<u>ACTAGT</u>ACAAAAGAGTGTGGAATTAC-3': SEQ ID NO:37) with restriction enzyme site (ApaI or SpeI) added. This PCR was performed using KOD -Plus- DNA Polymerase (Toyobo), with annealing temperature of 55° C., according to the attached protocol. The PCR products were digested with ApaI and SpeI and fractionated by electrophoresis on 1% agarose gel, DNA fragments of interest purified using QIAquick Gel Extraction Kit (Qiagen), and used as insert. As vector, pER8 (Reference 74) wherein transgene is induced by β-estradiol to express was used, digested with ApaI and Spe, and fractionated by electrophoresis on 1% agarose gel, similarly to the insert. DNA fragments of interest were purified using QIAquick Gel Extraction Kit and used as vector. Following procedures were performed according to the ligation step in the section 3 above.

6. Transformation of *Agrobacterium*

Vector for introduction was adjusted with TE to 10 ng/µl and used for transformation of *Agrobacterium*. Binary vector was constructed as follows. Compatible cells of 80 µl *Agrobacterium* GV3101 strain were fused on ice, to which 2 µl vector solution was added, mixed by pipetting, and left stood on ice for 30 minutes. This solution was transferred to cuvette, and electroporated (V=1.44 kV, T=2.5 kV/resistance, C=all out, R=R5 129) with Micro Pulser™ (Bio-Rad) to transform. The solution was then transferred into 1.5 ml Eppendorf tube, added to 1 ml of SOC medium [2% tryptone peptone, 0.5% yeast extract powder, 0.05% NaCl, 10 mM $MgCl_2$, 10 mM $MgSO_4$] and left stood at room temperature for one hour. The resultant solution was inoculated on LB agar medium [1% tryptone peptone, 0.5% yeast extract powder, 1% NaCl, 50 µg/ml kanamycin, 50 µg/ml rifampicin, 1% agarose], and cultured at 28° C. for two days. Single colonies were recovered and used for Agroinfiltration Experiment in the section 7 below.

7. Gene Transfer by Agroinfiltration Using Benthamiana Leaf

According to the method described by Thomas et al. (2000) (See Reference 41), Agroinfiltration was performed as follows. *Agrobacteria* harbouring binary vectors introduced were shake-cultured in LB liquid medium containing a selected antibiotic at 28° C. for two days. 2 ml of the culture solution was suspended in 8 ml LB liquid medium containing an antibiotic, and shake-cultured at 28° C. for further 3 hours. Density of *Agrobacteria* in the suspension was measured using a ultraviolet visible spectroscopic analysis system (DU series 600, Beckman) and calibrated by absorbance at wavelength 600 nm. The suspension was centrifuged (3,000×g, 15 minutes) at room temperature, and precipitates resuspended in 10 mM MES (pH 5.6) containing 150 µM acetonitocilingon, 10 mM $MgCl_2$ to $OD_{600}$=0.5.

Figure 26:
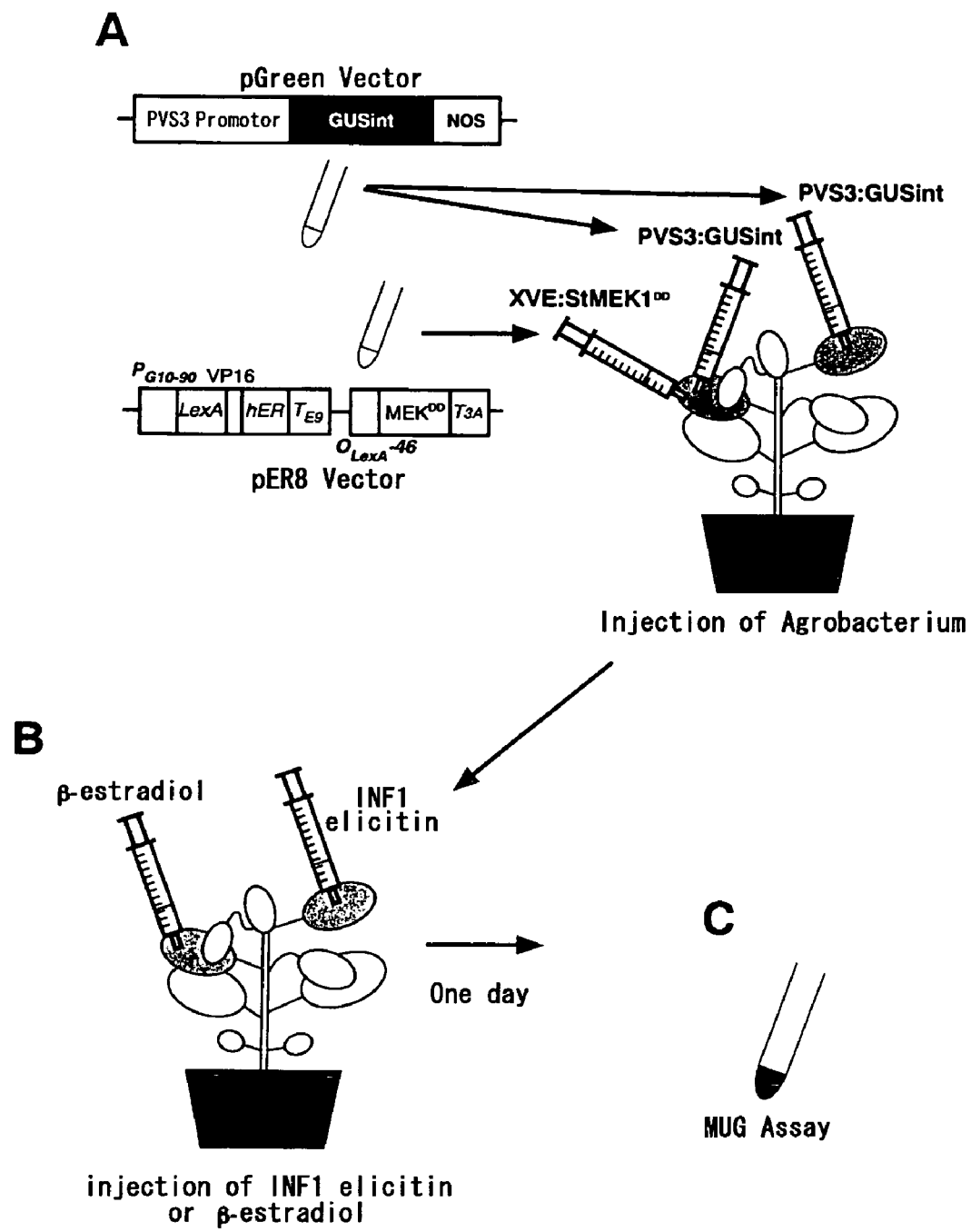
FIG. 26 shows the method for examining the PVS3 promoter activity for INF1 treatment or StMEK1$^{DD}$ expression. For INF1 treatment, Agrobacteria containing PVS3:GUSint was injected to leaves. For StMEK1$^{DD}$ expression, a mixture of Agrobacteria containing PVS3:GUSint and XVE:StMEK1$^{DD}$ was injected into leaves. The leaves were left stood for one day (A). Subsequently, for INF1 treatment, INF1 solution was injected into leaves. For StMEK1$^{DD}$ expression, β-estradiol was injected (B) before the leaves were left stood for one day to bring about StMEK1$^{DD}$ expression, and GUS activity determined (C).

For Agroinfiltration of *Agrobacteria* retaining PVS:GUSint only, suspension of $OD_{600}$=0.5 was injected into leaves, and 10 µg/ml INF1 solution was injected one day later to induce PVS3 promoter (FIG. 26). On the other hand, for Agroinfiltration of *Agrobacterium* retaining XVE: StMEK1$^{DD}$ or PVS:GUSint using pER8 vector, each of their solution were diluted to $OD_{600}$=0.005 and $OD_{600}$=0.25, respectively, XVE (LexA, VP16, estrogen receptor) system having 20 µM β-estradiol linked downstream of G10-90 promoter was induced to express StMEK1$^{DD}$ (Reference 74). As control area, pER8 vector, intead of XVE:StMEK1$^{DD}$, was used to inject 20 µM β-estradiol (FIG. 26).

The suspension was left stood at room temperature for one hour, and then injected into intercellular spaces of Benthamiana leaves using needless syringe. The plant after injection was left stood at 25° C. for 24 hours, and used for MUG (4-methylumbelliferyl β-D-glucuronide) assay described in the section 9 below.

8. Virus-Induced Gene Silencing in Benthamiana

Figure 27:
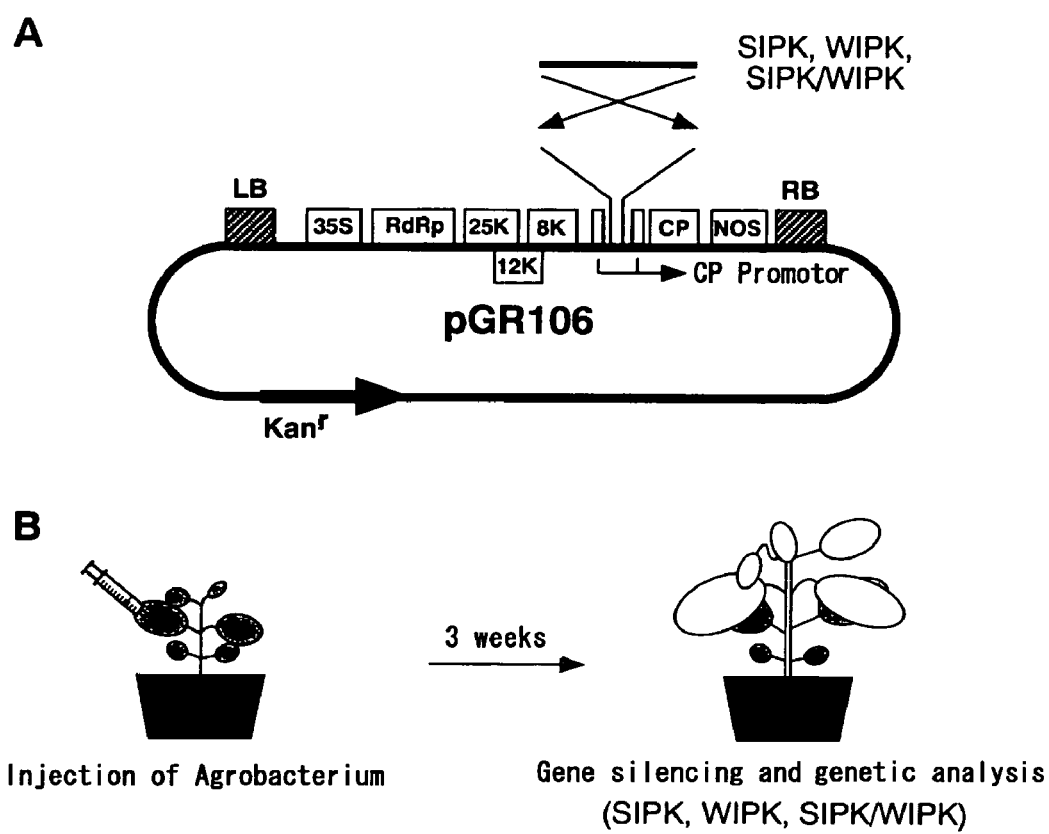
FIG. 27 shows a procedure for virus-inducible gene silencing. (A) shows the construction of silencing vector pGR106. Gene fragments to be silenced, cDNA fragments of SIPK and WIPK in this case, are inserted to pGR106. (B) schematically shows the virus infection caused by inoculation with Agrobacterium containing a vector.

It is known that when any nucleotide sequence within the virus with which plant infected contains any sequence homologous with any gene of the plant, virus-induced gene silencing results (Reference 67). In the present Example, PVX and Benthamiana systems having a stable incidence of gene silencing were used. To pGR106 which is a binary vector having PVX, any one of cDNA fragment of 230 bp from translation starting codon of SIPK, cDNA fragment of 178 bp from translation starting codon of WIPK, or cDNA coding SIPK and WIPK linked in tandem, was inserted to obtain gene silencing vector, which was then introduced into *Agrobacterium*. The *Agrobacterium* was cultured according to the method described in the section 7 above, and injected into Benthamiana leaves that have grown 3 weeks after seeding. The Benthamiana was allowed to grow one month and then had their upper leaves used for experiment (FIG. 27).

9. MUG Assay

MUG (4-methylumbelliferyl β-D-glucuronide) assay was performed according to the method of Gallagher (1992) (See Reference 60) in order to quantify GUS expression. 1 $cm^2$ pieces of three Benthamiana leaves that had been injected with *Agrobacterium* were ground in liquid nitrogen, and 200 µl extraction buffer [50 mM $NaHPO_4$ (pH 7.0), 10 mM β-mercaptoethanol, 10 mM EDTA, 0.1% sodium lauroyl sarcosine, 0.1% TritonX-100] added. The resultant solution was centrifuged (12,000 rpm, 4° C., 5 minutes) and supernatant recovered. Protein concentration of the recovered extraction was measured according to the protein quantification method described in the section 13 above, and 10 µl extraction was added to 90 µl fluoro metric buffer [extraction buffer, 2 mM MUG] at 37° C. to produce 100 µl reaction solution, which was left stood at 37° C. for one hour. The reaction solution was added to 900 µl quenching solution (0.2 M $Na_2CO_3$) for use in measurement. Using fluorospectrophotometer RF-5300PC (Shimadzu), emission spectrum at 455 nm was measured with excitation set at 365 nm. Calibration curve was generated using 4-MU (7-hydroxy-4-methylcoumarin), and measurement scaled at 4-MU nM/min·mg protein. In order to exclude any endogenous GUS activity from measurement, samples having its endogenous enzyme heat-denatured were prepared, and the balance between calibrated values were determined to calculate GUS activity derived from expression vector.

10. Extraction of Total RNA from Benthamiana Leaf

Total RNA was extracted from Benthamiana leaf based on SDS/phenol method according to the following procedure. 1 g of Benthamiana leaf was ground in mortal under added liquid nitrogen, added to 50 ml volume sterile centrifuge tubes containing extraction buffer (EB)[50 mM Tris-HCl (pH 7.5), 150 mM sodium chloride, 5 mM EDTA, 5% SDS] 5 ml, PCI [phenol/chloroform/isoamylalcohol (50:49:1, v/v/v)] 0.4 ml, 10 µl of mercaptoethanol 10 µl, vigorously mixed for one minute, to which PCI 4.8 ml was added followed by gentle agitation. This solution was ground with polytron type homogenizer (HG30, Hitachi) for two minutes, and centrifuged (1,300×g, 15 minutes). Aqueous phase (upper phase) was transferred into new 50 ml volume centrifuge tubes, to which PCI 6 ml added, agitated two minutes, and again centrifuged (1,300×g, 15 min.) at ordinary temperature. To aqueous phase (upper phase) 1/40 amount of 4 M sodium chloride and 2-fold amount of ethanol was added and mixed, the resultant mixture left stood at –20° C. for over 2 hours, and centrifuged (1,300×g, 15 minutes). To precipitates obtained, 2 ml of resuspension buffer (RB)[50 mM Tris-HCl (pH 7.5), 5 mM EDTA, 0.5% SDS] was added, and the mixture gently shaken for 15 minutes to achieve suspension. To this suspension, 0.2 ml 4 M sodium chloride and 4 ml ethanol was added, and the suspension left stood at –20° C. for over two hours, and centrifuged (1,300×g, 15 minutes). Resultant precipitates were washed with cold 1 ml 70% ethanol, suspended in 1 ml TE buffer [10 mM Tris-HCl (pH 7.5), 1 mM EDTA], transferred into Eppendorf tubes, to which 250 µl of 10 M lithium chloride was added, and left stood on ice for one hour. The suspension was centrifuged (22,000×g, 15 minutes) at 4° C., and RNA recovered as precipitates. This lithium precipitation procedure was repeated twice, resultant precipitates suspended in 300 µl TE buffer, to which 100 µl chloroform/isoamylalcohol (24:1, v/v) was added, vigorously agitated, and centrifuged (22,000×g, 15 minutes) at 4° C. To aqueous phase (upper phase), 1/10 amount of 3 M sodium acetate (pH 5.2) and 2-fold amount of ethanol were added, resultant mixture left stood at –20° C. for over 2 hours, and centrifuged (22,000×g, 5 minutes). Resultant precipitates was washed in cold 70% ethanol, air-dried for 10 minutes, suspended in 40 µl TE buffer to obtain total RNA, which was then stored at –80° C. as RNA sample.

11. Northern Analysis

The total RNA was fractionated by formaldehyde agarose gel eletrophoresis (Reference 37), and transferred and to immobilized on Hybond-N$^+$ nylon membrane (Amersham) by alkaline blotting (Reference 68).

The nylon membrane with RNA adsorbed thereon was placed in prehybridization solution [50% formamide, 5×Denhardt solution (Reference 37), 5×SSPE (Reference 37), 0.5%

SDS, 100 µg/ml heat-denatured salmon sperm DNA (Pharmacia)] at 42° C. for over one hour, to which $^{32}$P-labelled DNA probe was added, and allowed hybridization at 42° C. for over 16 hours. The membrane was sequentially washed in 0.1% SDS-containing 4×SSPE at room temperature for 15 minutes (twice), 0.1% SDS-containing 4×SSPE at 60° C. for 15 minutes, and 0.1% SDS-containing 2×SSPE at 60° C. for 15 minutes (once). Autoradiography was performed using X-ray film OMAT-AR (Kodak) and intensifying screen Lighting Plus (Dupont) at −80° C.

12. Production of Probes

Using plasmid pTEAS (Facchini and Chappel, 1992) having tobacco TEAS cDNA incorporated as temperate, TEAS cDNA fragments were amplified by PCR using primers (5'-GTCGACGACACAGCCACGTACGAGGT-3': SEQ ID NO: 38, 5'-ATCGATAGACTTTCTCCGGATGAGTG-3': SEQ ID NO: 39). Reaction was performed using 2 ng plasmid having TaKaRa Taq™(Takara Shuzo) and an insert DNA incorporated, on DNA thermal cycler (PJ2000, Perkin Elmer Cetus) at 94° C. for one minute (heat-denaturation), at 53° C. for 45 seconds (annealing), at 72° C. for 2 minutes (DNA elongation), in 25 cycles. The size of DNA fragments amplified by 0.8% agarose electrophoresis was determined. The DNA fragments were purified from the gel using QIAquick Gel Extraction Kit (Qiagen). $^{32}$P-labeled DNA probes were produced using Random Priming method (Reference 17) using [α-$^{32}$P] dCTP (111 TBq/mmol, ICN Biochemicals) and Megaprime DNA labelling system (Amersham).

Example 9

Response to INF1 by PVS3 Promoter Deletion Clone Introduced by Agroinfiltration

Figure 28:
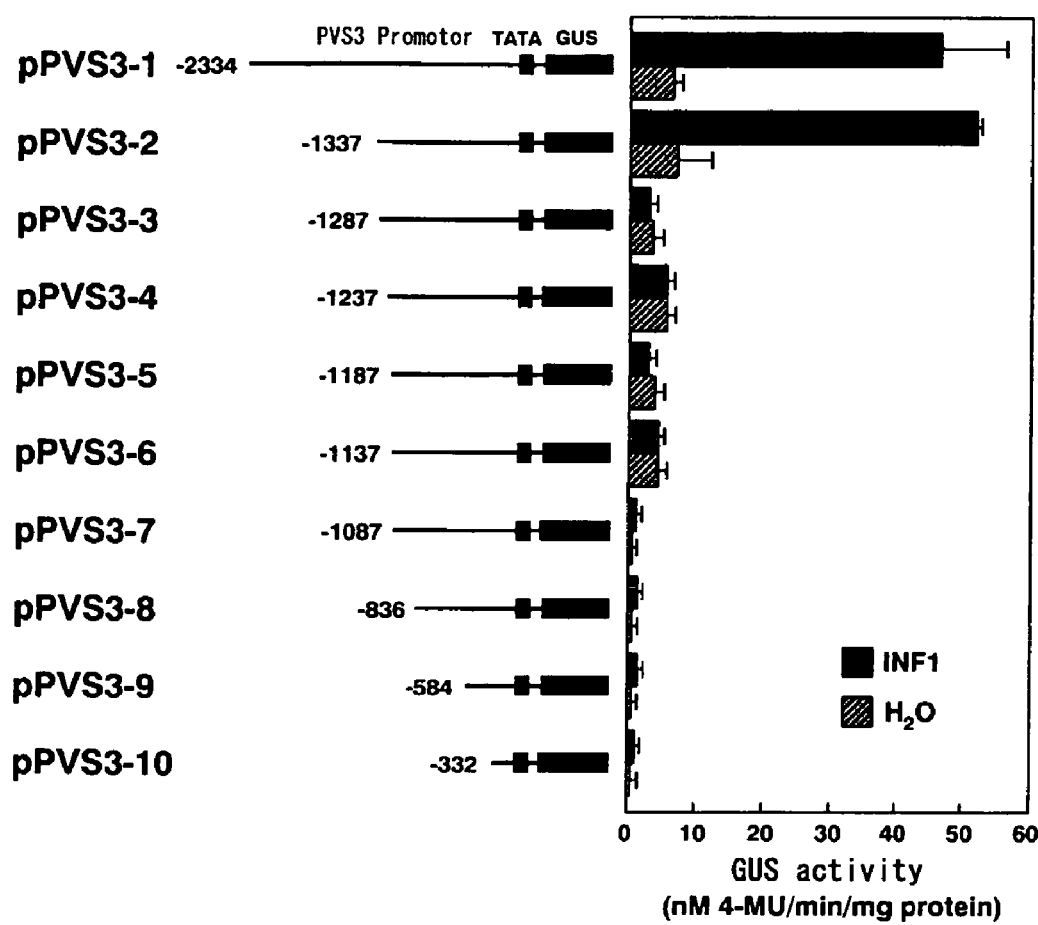
FIG. 28 shows PVS3 promoter activity responsive to INF1 treatment. In −1337 (pPVS3-2), GUS activity was induced by injecting INF1, in contrast to control area. On the other hand, deletion of PVS3 promoter up to −1,287 (pPVS3-3) significantly reduced GUS activity induced by INF1 treatment.

INF1, *P. infestans*-derived elicitor protein, is an effective elicitor for Benthamiana (Reference 63). Binary vectors containing GUS gene including introns linked in-frame downstream of PVS3 promoter were introduced by Agroinfiltration into Benthamiana leaves to examine INF1-induced GUS activity (FIG. 27). When binary vectors pPVS3-1 containing full length PVS3 promoter inserted were introduced, a significant increase of GUS activity was observed compared to water treatment (FIG. 28). In order to examine cis-sequence of PVS3 promoter response to INF1, deletion clones were produced to construct binary vectors and examine GUS activity. As a result, deletion up to −1,337 (pPVS3-2: SEQ ID NO: 22) retained INF1 responsiveness, whereas deletion up to −1,287 (pPVS3-3) greatly reduced GUS activity induced by INF1. This result indicates that cis-sequence of PVS3 promoter is involved in 50 bp (SEQ ID NO: 23) between pPVS3-2 and pPVS3-3 (FIG. 29).

Example 10

Induction of PVS3 Promoter by StMEK1$^{DD}$

Figure 30:
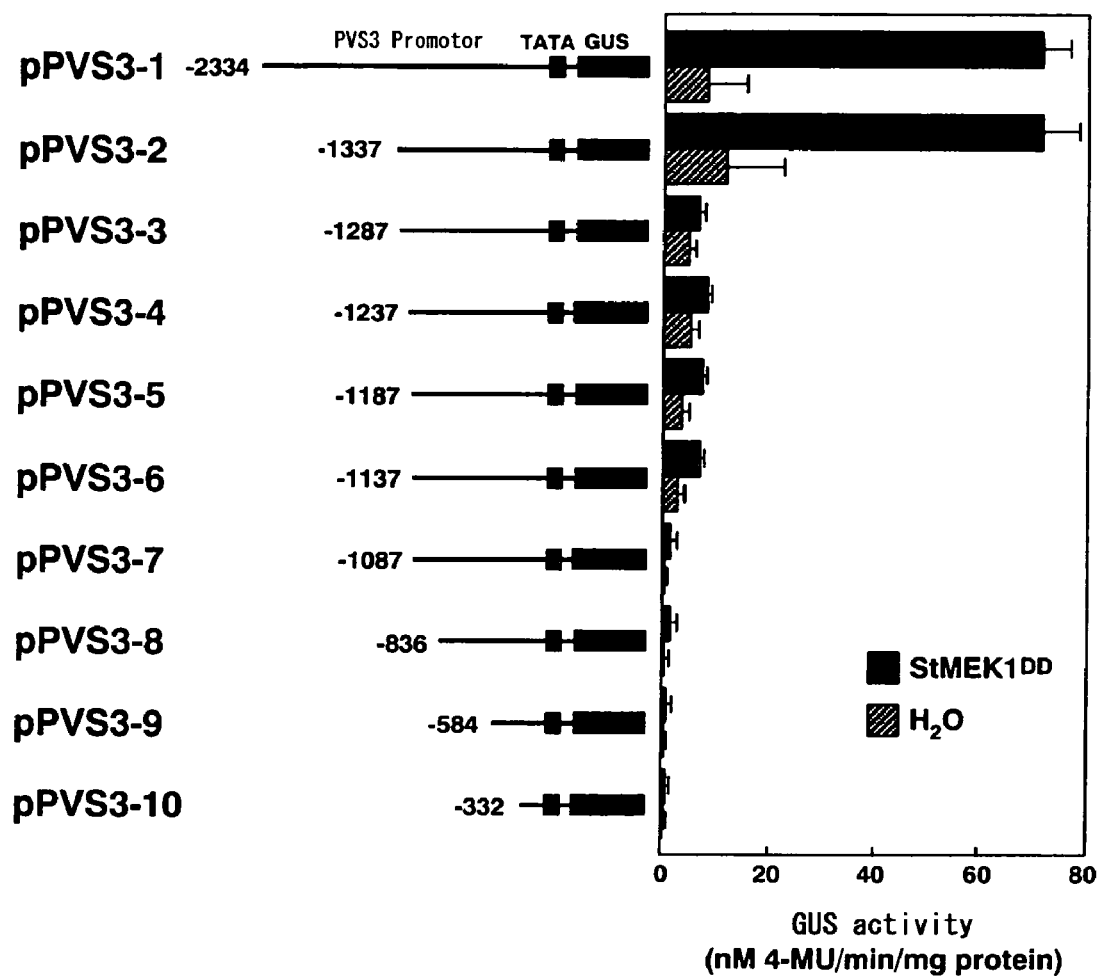
FIG. 30 shows the PVS3 promoter activity in response to StMEK1$^{DD}$. In −1,337 (pPVS3-2), higher GUS activity compared to control area was induced by injecting β-estradiol. On the other hand, deletion of PVS3 promoter up to −1,287 (pPVS3-3) significantly reduced GUS activity induced by β-estradiol.

StMEK1$^{DD}$ is a constitutive active mutant produced by amino acid substitution of MAPKK, and found to induce SIPK and WIPK when introduced by Agroinfiltration into Benthamiana leaf (Reference 64). In order to determine whether or not the region of PVS3 promoter region that is responsive to INF1 treatment is similarly responsive to StMEK1$^{DD}$, binary vectors containing GUS gene including introns linked to PVS3 promoter were introduced by Agroinfiltration into Benthamiana. At the same time, the leaves were co-infected with *Agrobacteria* transformed with binary vectors which have StMEK1$^{DD}$ linked downstream of XVE induced by β-estradiol, and β-estradiol injected. The leaves were then left stood for one day to allow expression of StMEK1$^{DD}$ to examine GUS activity (FIG. 27). As a result, deletion up to −1,337 (pPVS3-2: SEQ ID NO:22) produced an induction of greater GUS activity by injection of β-estradiol compared to control area (FIG. 30). On the other hand, deletion of PVS3 promoter up to −1,287 (pPVS3-3) resulted a significant decrease of GUS activity induced by β-estradiol treatment. This result indicates that the 50 bp (SEQ ID NO:23) between pPVS3-2 and pPVS3-3 is involved in cis-sequence responsive to StMEK1$^{DD}$, and that it is similar to that cis-sequence for INF1 (FIG. 29).

Example 11

Figure 31:
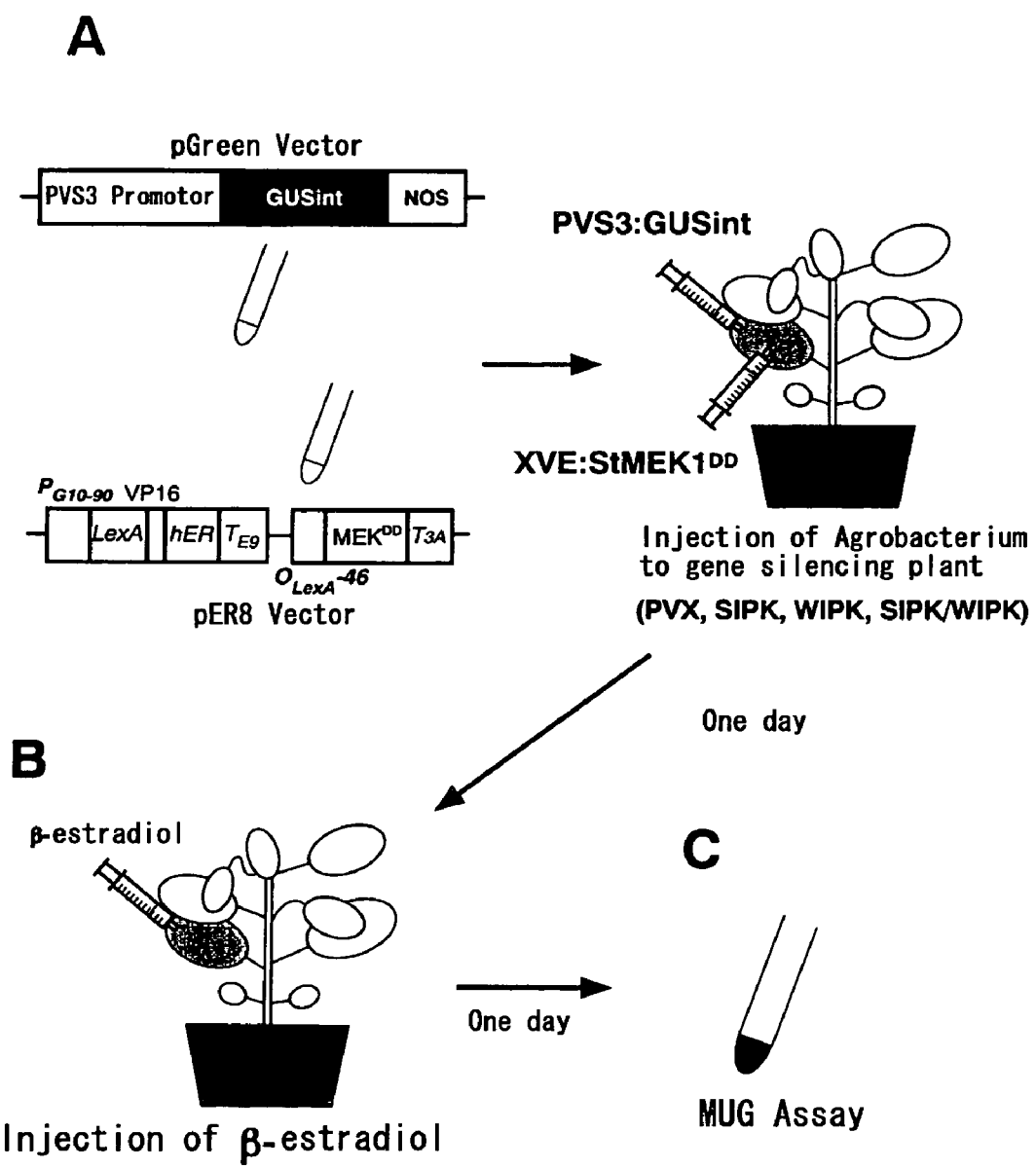
FIG. 31 shows the method for examining effect of WIPK or SIPK on PVS3 promoter activity induced by StMEK1$^{DD}$ expression. A mixture of Agrobacteria containing PVS3:GUSint and XVE:StMEK1$^{DD}$ was injected into silencing leaves and left stood for one day (A). β-estradiol was then injected (B) and the leaves left stood again for another one day to allow StMEK1$^{DD}$ expression. The resultant GUS activity was examined (C).

Effect of SIPK and WIPK Silencing on PVS3 Promoter Activity Induced by StMEK1$^{DD}$ pPVS3-1 was introduced by Agroinfiltration into Benthamiana silenced either SIPK or WIPK alone, or both of SIPK and WIPK, to examine GUS activity. The Benthamiana was co-infected by Agroinfiltration with StMEK1$^{DD}$ that is linked downstream of XVE. One day after the infection, β-estradiol was injected, the leaves left stood for one day to allow expression of StMEK1$^{DD}$ (FIG. 31). Compared to control plant infected with an empty PVX vector, the SIPK or WIPK silenced plant showed no significant reduction of GUS activity (FIG. 32). On the other hand, VIGS of both SIPK and WIPK showed a significant reduction of GUS activity.

Example 12

Effect of SIPK and WIPK Silencing on TEAS Expression Induced by StMEK1$^{DD}$

In order to examine the control mechanism of TEAS which is tobacco sesquiterpene cyclase, expression vectors containing StMEK1$^{DD}$ gene linked to 35S promoter were introduced by Agroinfiltration into SIPK and/or WIPK silenced Benthamiana, and total RNA extracted in a time course. Northern analysis using TEAS cDNA as a probe revealed that VIGS of both SIPK and WIPK resulted in a significantly lesser accumulation of TEAS mRNA (FIG. 32). This result indicates that SIPK and WIPK have similar roles for PVS3 promoter activity.

As shown in the above Examples, in order to explore any promoter region that is important for PVS3 gene expression, PVS3 promoter was linked upstream GUS gene to construct a deletion clone, which was then treated with INF1 to measure GUS activity (FIG. 28). Deletion pPVS3-2 (SEQ ID NO: 22) showed a significant increase in activity provided by INF1 treatment, whereas deletion pPVS3-3 showed no increase in activity (FIG. 28). Gene transcription is known to be induced when transcription factor protein produced by stimuli is bound to cis-sequence within promoter region. Therefore, cis-sequence that is bound by transcription factor is thought to lie between deletion pPVS3-2 and pPVS3-3. Presently, any known control motif has not been found in this 50 bp region (SEQ ID NO:23) (FIG. 29).

It has been shown that SIPK, which is MAPK for tobacco, controls expression of 3-hydroxy-3-methylglutaryl CoA reductase (HMGR) which plays an important role in sesquiterpenoid phytoalexin synthesis (Reference 73). It is known that MAPK cascade plays an important role in controlling signal transduction in plant, and activates a variety of protective responses located downstream (Reference 71). More-over, it has been recently shown that when expression vector carrying StMEK1$^{DD}$ gene linked downstream of 35S promoter is introduced by Agroinfiltration into Benthamiana, TEAS is induced at the transcriptional level (Reference 64). In order to determine whether or not the region of PVS3 promoter that is responsive to INF1 treatment is similarly responsive to StMEK1$^{DD}$, deletion clone and StMEK1$^{DD}$ were co-expressed by Agroinfiltration in Benthamiana leaf to examine GUS activity. Similarly to INF1, deletion pPVS3-2 showed a significant increase in activity provided by StMEK$^{DD}$, whereas deletion pPVS3-3 showed no significant increase in activity (FIG. 30). Zhang et al. (1998) reported that treatment of cultured cells of tobacco with cryptogein elicitin produced by *Phytophthora* cryptogea or with parasiticein produced by *P. parasitica* results in activation of SIPK and WIPK (Reference 72). Taking the result of the present experiment into consideration, it may be demonstrated that MAPK cascade may be involved in the induction process of PVS3 via signal transduction by INF1 elicitin produced by *P. infestans*. In order to investigate this possibility, binary vector containing PVS3 promoter was introduced into SIPK or WIPK alone, or both SIPK and WIPK genes silenced Benthamiana leaves by Agroinfiltration, followed by INF1 elicitor treatment to examine GUS activity (FIG. 32). Compared to PVX inoculated control plant, WIPK or SIPK silenced plant showed a little reduction in GUS activity. On the other hand, both SIPK and WIPK silenced plant showed a significant reduction in GUS activity. These results suggest that TEAS, which is an endogenous sesquiterupene cyclase, is also controlled by SIPK and WIPK. In fact, when StMEK1$^{DD}$ gene was expressed in SIPK and/or WIPK silenced Benthamiana, TEAS mRNA accumulation was significantly suppressed only in the area where both SIPK and WIPK were silenced (FIG. 32).

Samuel and Ellis (2002) reported that exposure of tobacco plant to a high concentration of ozone activates SIPK and WIPK, thereby inducing cell death accompanied by production of reactive oxygen species (Reference 69). They found that exposure of transgenic plant showing SIPK silencing by RNAi (RNA interference) to ozone causes a significant increase in WIPK activity, resulting in induction of cell death. In view of this report, SIPK and WIPK may compensate each other to control the expression of downstream PVS3 gene.

This invention is not limited in any way by the embodiments nor Examples described above, but encompasses any modification thereto a skilled person would think of without departing the scope of the present invention as claimed.

INDUSTRIAL APPLICABILITY

Pathogen-responsive promoter according to the present invention is applicable to expression of any desired gene specifically at the time of pathogen infection in plant cells. Accordingly, by employing any gene involved in protective response, for instance, it allows creation of pathogen-resistant plant which has a prompt protective response to pathogen infection.

I claim:

1. An isolated pathogen-responsive promoter, comprising the nucleotide sequence shown in SEQ ID NO: 1, wherein the promoter functions in plant cells.

2. An isolated pathogen-responsive promoter, comprising the nucleotide sequence shown in SEQ ID NO: 2, wherein the promoter functions in plant cells.

3. An isolated pathogen-responsive promoter, comprising the nucleotide sequence shown in SEQ ID NO: 22, wherein the promoter functions in plant cells.

4. A pathogen-responsive promoter comprising the nucleotide sequence shown in SEQ ID NO:23; wherein the promoter functions in plant cells.

5. The pathogen-responsive promoter according to claim 4, wherein the promoter is responsive to *Phytophthora* infection.

6. A vector comprising the pathogen-responsive promoter according to claim 4.

7. A DNA construct comprising the pathogen responsive promoter according to claim 4 and a gene operably linked under the control of the promoter and expressed in plant to activate the defense response of the plant.

8. The DNA construct according to claim 7, wherein the expression product of the gene has the function to activate a signaling pathway controlling the defense response of the plant.

9. The DNA construct according to claim 7, wherein the expression product of the gene has the function to activate salicylic acid-induced protein kinase or Wound-Induced Protein Kinase.

10. The DNA construct according to claim 7, wherein the gene encodes a constantly active form of MEK.

11. A plant transformed with the DNA construct according to claim 7.

12. The plant according to claim 11, wherein the plant belongs to Solanaceae.

13. The plant according to claim 11, wherein the host plant belongs to *Solanum tuberosum*.

14. A method for producing a transgenic plant, comprising the step of: transforming a plant with the DNA construct of claim 7.

15. A method for inducing pathogen resistance to a plant, comprising the step of: transforming the plant with the DNA construct according to claim 7.

16. A pathogen resistant plant produced by the method of claim 15.

17. A transgenic plant produced by the method of claim 14.

18. An isolated pathogen-responsive promoter consisting of SEQ ID NO: 1, wherein the promoter functions in plant cells.

19. An isolated pathogen-responsive promoter consisting of SEQ ID NO: 2, wherein the promoter functions in plant cells.

20. An isolated pathogen-responsive promoter consisting of SEQ ID NO: 22, wherein the promoter functions in plant cells.

* * * * *